United States Patent
Chimmanamada et al.

(10) Patent No.: US 10,117,944 B2
(45) Date of Patent: Nov. 6, 2018

(54) TARGETED THERAPEUTICS

(71) Applicant: Madrigal Pharmaceuticals, Inc., West Conshohocken, PA (US)

(72) Inventors: Dinesh U. Chimmanamada, Arlington, MA (US); Weiwen Ying, Lexington, MA (US)

(73) Assignee: MADRIGAL PHARMACEUTICALS, INC., West Conshohocken, PA (US)

( * ) Notice: Subject to any disclaimer, the term of this patent is extended or adjusted under 35 U.S.C. 154(b) by 0 days.

(21) Appl. No.: 15/222,145

(22) Filed: Jul. 28, 2016

(65) Prior Publication Data
US 2017/0014519 A1 Jan. 19, 2017

Related U.S. Application Data

(63) Continuation of application No. PCT/US2015/013440, filed on Jan. 29, 2015.

(60) Provisional application No. 61/933,224, filed on Jan. 29, 2014.

(51) Int. Cl.
| | |
|---|---|
| *A61K 31/69* | (2006.01) |
| *A61K 47/48* | (2006.01) |
| *A61K 31/365* | (2006.01) |
| *A61K 31/395* | (2006.01) |
| *A61K 31/56* | (2006.01) |
| *A61K 47/55* | (2017.01) |
| *A61K 31/436* | (2006.01) |

(52) U.S. Cl.
CPC .......... *A61K 47/481* (2013.01); *A61K 31/365* (2013.01); *A61K 31/395* (2013.01); *A61K 31/56* (2013.01); *A61K 31/69* (2013.01); *A61K 47/55* (2017.08); *A61K 31/436* (2013.01)

(58) Field of Classification Search
CPC ....... A61K 47/48; A61K 31/436; A61K 31/69
USPC ........................................................ 514/64
See application file for complete search history.

(56) References Cited

U.S. PATENT DOCUMENTS

| | | | |
|---|---|---|---|
| 6,214,345 B1 | 4/2001 | Firestone et al. |
| 6,372,712 B1 | 4/2002 | Briesewitz et al. |
| 7,344,699 B2 | 3/2008 | Lappin et al. |
| 7,671,010 B2 | 3/2010 | Arap et al. |
| 7,769,423 B2 | 8/2010 | Viglianti et al. |
| 7,834,181 B2 | 11/2010 | Chiosis et al. |
| 2007/0134154 A1 | 6/2007 | Chang et al. |
| 2007/0297980 A1 | 12/2007 | Xie et al. |
| 2009/0226431 A1 | 9/2009 | Habib |
| 2009/0298857 A1 | 12/2009 | Chiosis et al. |
| 2011/0064751 A1 | 3/2011 | Mossner et al. |
| 2011/0217241 A1 | 9/2011 | Yu et al. |
| 2012/0003160 A1 | 1/2012 | Wolf et al. |
| 2012/0064107 A1 | 3/2012 | Eliasof |
| 2012/0213854 A1 | 8/2012 | Fetzer |
| 2013/0317208 A1 | 11/2013 | Ramstack et al. |
| 2015/0104407 A1 | 4/2015 | Yurkovetskiy et al. |
| 2015/0105539 A1 | 4/2015 | Miao et al. |
| 2015/0105540 A1 | 4/2015 | Miao et al. |
| 2015/0250896 A1 | 9/2015 | Zhao |

FOREIGN PATENT DOCUMENTS

| | | |
|---|---|---|
| EP | 2133094 A1 | 12/2009 |
| JP | 2005-520795 | 7/2005 |
| JP | 2012-502921 | 2/2012 |
| WO | 2000/61578 A1 | 10/2000 |
| WO | 2002/036171 A1 | 5/2002 |
| WO | 2003/050295 A2 | 6/2003 |
| WO | 2004/054624 A1 | 7/2004 |
| WO | 2007/053792 A1 | 5/2007 |
| WO | 2007/077209 A1 | 7/2007 |
| WO | 2008/044029 A1 | 4/2008 |
| WO | 2009/036092 A2 | 3/2009 |
| WO | 2010/028389 A1 | 3/2010 |
| WO | 2010/033733 A1 | 3/2010 |
| WO | 2011/116181 A1 | 9/2011 |
| WO | 2011/133879 A2 | 10/2011 |
| WO | 2012/052843 A1 | 4/2012 |
| WO | 2012/096919 A1 | 7/2012 |
| WO | 2013/158644 A2 | 10/2013 |
| WO | 2015/038649 A1 | 3/2015 |
| WO | 2015/066053 A2 | 5/2015 |
| WO | 2015/095829 A1 | 6/2015 |

OTHER PUBLICATIONS

Jaracz, S. et al., "Recent advances in tumor-targeting anticancer drug conjugates" (2005) Bioorganic & Medicinal Chemistry 13:5043-5054.

Anonymous, "Synta Announces Publication of First Patent Application Covering it Hsp90-inhibitor Drug Conjugate (HDC) Platform", Oct. 31, 2013 Internet: http://www.evaluategroup.com/Universal/View.aspx?type=Story&id=466037.

Extended European Search Report dated May 19, 2017 in Application No. 15742953.1, entitled: Targeted Therapeutics.

Marketwatch., Synta Announces Launch of Proprietary Small Molecule Hsp90-Inhibitor Drug Conjugate Platform (Sep. 10, 2013) Internet <http://www.marketwatch.com/story/synta-announces-launch-of-proprietary-small-molecule-hsp90-inhibitor-drug-conjugate-platform-2013-09-10>.

(Continued)

*Primary Examiner* — Kevin E Weddington
(74) *Attorney, Agent, or Firm* — DT Ward, PC; Donna T. Ward; Heng Zhu

(57) ABSTRACT

The present invention provides pharmacological compounds including an effector moiety conjugated to a binding moiety that directs the effector moiety to a biological target of interest. Likewise, the present invention provides compositions, kits, and methods (e.g., therapeutic, diagnostic, and imaging) including the compounds. The compounds can be described as a protein interacting binding moiety-drug conjugate (SDC-TRAP) compounds, which include a protein interacting binding moiety and an effector moiety. For example, in certain embodiments directed to treating cancer, the SDC-TRAP can include an Hsp90 inhibitor conjugated to a cytotoxic agent as the effector moiety.

12 Claims, 3 Drawing Sheets

(56) References Cited

OTHER PUBLICATIONS

International Search Report and Written Opinion dated Jun. 29, 2015 in Application No. PCT/US2015/013440, entitled: Targeted Therapeutics.
Arap, W. et al., "Cancer Treatment by Targeted Drug Delivery to Tumor Vasculature in a Mouse Model" (1998) Science 279:377-380.
Bader, R.A., "The Development of Targeted Drug Delivery Systems for Rheumatoid Arthritis Treatment" (2012) Book edited by Andrew B. Lemmey, ISBN 978-953-307-850-2, http://www.intechopen.com/books/rheumatoid-arthritis-treatment.
Baker, J.R., Jr., "Dendrimer-based nanoparticles for cancer therapy" (2009) Hematology pp. 708-719.
Borgman, S., "Biodistribution of HPMA Copolymer-Aminohexylgeldanamycin-RGDfK Conjugates for Prostate Cancer Drug Delivery" (2009) Molecular Pharmaceuticals 6(6):1836-1847.
Borman, S. "Multivalency: Strength in Numbers" (2000) C&EN pp. 48-53.
Chen, C. Y.-C., "Bioinformatics, chemoinformatics, and pharmainformatics analysis of HER2/HSP90 dual-targeted inhibitors" (2010) J. Taiwan Chem. Eng. 41:143-149.
Dharap, S.S. et al., "Tumor-specific targeting of an anticancer drug delivery system by LHRH peptide" (2005) PNAS 102(36):12962-12967.
Du, Y. et al., "High-Throughput Screening Fluorescence Polarization Assay for Tumor Specific Hsp90" (2007) J. Biomolecular Screening 12(7):915-924.
Ducry, L. and B. Stump, "Antibody-Drug Conjugates: Linking Cytotoxic Payloads to Monoclonal Antibodies" (2010) Bioconjugate Chem. 21(1):5-13.
Gerber, D.E., "Targeted Therapies: A New Generation of Cancer Treatments" (2008) American Family Physician 77(3):311-319.
Graham, B. et al., "The heat shock protein 90 inhibitor, AT13387, displays a long duration of action in vitro and in vivo in non-small cell lung cancer" (2012) Cancer Science 103(3):522-527.
Hatakeyama, S. et al., "Targeted drug delivery to tumor vasculature by a carbohydrate mimetic peptide" (2011) PNAS 108(49):19587-19592.
Inoue, T. et al., "An inducible translocation strategy to rapidly activate and inhibit small GTPase signaling pathways" (2005) Nature Methods 2(2):415-418.
Janáky, T. et al., "Analogues of luteinizing hormone-releasing hormone containing cytotoxic groups" (1992) Proc. Natl. Acad. Sci. 89:972-976.
Jhaveri, K. et al., "Ganetespib:research and clinical development" (2015) Onco Targets and Therapy 8:1849-1858.
Kim, Y.-S. et al., "Effects of Targeting Moiety, Linker, Bifunctional Chelator, and Molecular Charge on Biological Properties of 64Cu-Labeled Triphenylphosphonium Cations" (2008) J. Med. Chem. 51:2971-2984.
Koga, F. et al., "Inhibition of Cancer Invasion and Metastasis by Targeting the Molecular Chaperone Heat-shock Protein 90" (2009) Anticancer Research 29:797-808.

Kuduk, S.D., et al., "Synthesis and Evaluation of Geldanamycin-Testosterone Hybrids" (2000) Bioorg. Med. Chem. Letters 10:1303-1306.
Leamon, C.P. and J.A. Reddy, "Folate-targeted chemotherapy" (2004) Advanced Drug Delivery Reviews 56:1127-1141.
Mandler, R. e tal., "Synthesis and Evaluation of Antiproliferative Activity of a Geldanamycin-HerceptinTM Immunoconjugate" (2000) Bioorg. & Med. Chem. Letters 10:1025-1028.
Nagy, A. et al., "Selective coupling of methotrexate to peptide hormone carriers through a γ-carboxamide linkage of its glutamic acid moiety: Benzotriazol-1-yloxytris(dimethylamino)phosphonium hexafluorophosphate activation in salt coupling" (1993) Proc. Natl. Acad. Sci. 90(13):6373-6376.
Norez, C. et al., "Chemical conjugation of F508-CFTR corrector deoxyspergualin to transporter human serum albumin enhances its ability to rescue C1-channel functions" (2008) Am. J. Physiol. Lung Cell Mol. Physiol 295:L336-L347.
Park, D. et al., "Noninvasive Imaging of Cell Death Using an Hsp90 Ligand" (2011) J. Am. Chem. Soc. 133(9):2832-2835.
Rigaudy, P. et al., "Attempts to Target Antitumor Drugs toward Opioid Receptor-rich Mouse Tumor Cells with Enkephalin-Ellipticinium Conjugates" (1989) Cancer Research 49(7):1836-1842.
Scarano, W. et al., "Folate Conjugation to Polymeric Micelles via Boronic Acid Ester to Deliver Platinum Drugs to Ovarian Cancer Cell Lines" (2013) Biomacromolecules 14:962-975.
Sidera, K. and E. Patsavoudi, "Extracellular HSP92" (2008) Cell Cycle 7(10):1564-1568.
Sinha, R., "Nanotechnology in cancer therapeutics: bioconjugated nanoparticles for drug delivery" (2006) Mol. Cancer Ther. 5(8):1909-1917.
Sprancmanis, L.A., et al., "Determination of the anticancer drug, 15-deoxyspergualin, in plasma ultrafiltrate by liquid chromatography and precolumn derivatization with naphthalene-2,3-dicarboxaldehyde/cyanide*" (1990) J. Pharma. & Biomed. Analysis 8(2):165-175.
Stangl, S. et al., "In vivo imaging of CT26 mouse tumours by using cmHsp70.1 monoclonal antibody" (2011) 15(4):874-887.
Tse, A.N. et al., "90-kDa Heat Shock Protein Inhibition Abrogates the Topoisomerase I Poison-Induced G2/M Checkpoint in p53-Null Tumor cells by depleting Chk1 and Wee1" (2009) Molecular pharmacology 75(1):124-133.
Wang, Y. et al., "STA-9090, a small-molecule Hsp90 inhibitor for the potential treatment of cancer" (2010) Current Opinion in Investigational Drugs 11(12):1466-1476.
Webb, S. "Back on target" (2013) Nature Biotechnology 31(3):191-193.
Wick, M.C. et al., "In vivo imaging of the effect of LPS on arterial endothelial cells:molecular imaging of heat shock protein 60 expression" (2008) Cell Stress and Chaperones 13:275-285.
Communication pursuant to Article 94(3) EPC dated Jun. 29, 2018 in co-pending European Application No. 15 742 953.1, entitled, "Targeted Therapeutics".

TARGETED THERAPEUTICS

CROSS-REFERENCE TO RELATED APPLICATIONS

This application is a continuation of International Application No. PCT/US2015/013440, filed on Jan. 19, 2015, which claims the benefit of priority to U.S. Provisional Patent Application No. 61/933,224, filed on Jan. 29, 2014, the entire contents of which are hereby incorporated herein by reference.

FIELD OF THE INVENTION

The present invention relates to pharmacological compounds including an effector moiety conjugated to a binding moiety that directs the effector moiety to a biological target of interest. The compounds have broad pharmacological applications, including therapeutics, diagnostics, and imaging. For example, the compounds can specifically direct therapeutic effector moieties to target cells or tissue of interest, for targeted chemotherapeutic treatment of conditions such as cancer.

BACKGROUND OF THE INVENTION

Although tremendous advances have been made in chemotherapy, currently available therapeutics and therapies remain unsatisfactory and the prognosis for the majority of patients diagnosed with chemotherapeutically treated diseases (e.g., cancer) remains poor. Often, the applicability and/or effectiveness of chemotherapy, as well as other therapies and diagnostics employing potentially toxic moieties, is limited by undesired side effects.

Many disease and disorders are characterized by the presence of high levels of certain proteins in specific types of cells. In some cases, the presence of these high levels of protein is caused by overexpression. Historically, some of these proteins have been useful targets for therapeutic molecules or used as biomarkers for the detection of disease. One class of overexpressed intracellular protein that has been recognized as a useful therapeutic target is known as the heat shock proteins.

Heat shock proteins (HSPs) are a class of proteins that are up-regulated in response to elevated temperature and other environmental stresses, such as ultraviolet light, nutrient deprivation, and oxygen deprivation. HSPs have many known functions, including acting as chaperones to other cellular proteins (called client proteins) to facilitate their proper folding and repair, and to aid in the refolding of misfolded client proteins. There are several known families of HSPs, each having its own set of client proteins. Hsp90 is one of the most abundant HSP families, accounting for about 1-2% of proteins in a cell that is not under stress and increasing to about 4-6% in a cell under stress.

Inhibition of Hsp90 results in degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer. Hsp90 has been shown by mutational analysis to be necessary for the survival of normal eukaryotic cells. However, Hsp90 is overexpressed in many tumor types, indicating that it may play a significant role in the survival of cancer cells and that cancer cells may be more sensitive to inhibition of Hsp90 than normal cells. For example, cancer cells typically have a large number of mutated and overexpressed oncoproteins that are dependent on Hsp90 for folding. In addition, because the environment of a tumor is typically hostile due to hypoxia, nutrient deprivation, acidosis, etc., tumor cells may be especially dependent on Hsp90 for survival. Moreover, inhibition of Hsp90 causes simultaneous inhibition of a number of oncoproteins, as well as hormone receptors and transcription factors, making it an attractive target for an anti-cancer agent. In view of the above, Hsp90 has been an attractive target of drug development, including such Hsp90 inhibitor (Hsp90i) compounds as ganetespib, AUY-922, and IPI-504. At the same time, the advancement of certain of these compounds which showed early promise, e.g., geldanamycin, has been slowed by those compounds' toxicity profile. Hsp90i compounds developed to date are believed to show great promise as cancer drugs, but other ways the ubiquity of Hsp90 in cancer cells might be leveraged have heretofore remained unexplored until now. Accordingly, the need exists for therapeutic molecules that selectively target proteins, such as Hsp90, that are overexpressed in cells associated with particular diseases or disorders.

SUMMARY OF THE INVENTION

The present invention provides pharmacological molecules ("SDC-TRAPs") including an effector moiety conjugated to a binding moiety, which directs the effector moiety into a target cell of interest in a manner that traps the molecule in the target cell. In a specific embodiment, the effector moiety is conjugated via a cleavable bond or linker to the binding moiety, such that the cleavable bond or linker is preferentially cleaved after the SDC-TRAP enters the target cell. The inventors of the instant application have discovered that the SDC-TRAP molecules of the invention can be used to selectively deliver an effector moiety to a specific type of cell in order to increase the intracellular level of the effector moiety in the target cell as compared to other cells. The inventors have demonstrated that certain SDC-TRAP molecules of the invention enter target cells by passive diffusion and are selectively retained in the target cells. Specifically, the inventors have shown that certain SDC-TRAP molecules of the invention are selectively retained only in cells that overexpress or otherwise have a high intracellular level of the protein to which the binding moiety binds. There are numerous advantages to these SDC-TRAP molecules and to methods of using these molecules that are described herein.

Specifically, the invention provides SDC-TRAP molecules that are targeted to cells of interest and trapped intracellularly for a sufficient period of time such that the effector moiety has the desired biological effect. In one embodiment, these SDC-TRAPs allow for the targeting of an effector moiety to a particular type of cell based on the overexpression of an intracellular protein that is characteristic of a particular disease or disorder. Accordingly, the present invention provides compositions, kits, and methods (e.g., therapeutic, diagnostic, and imaging) including the compounds.

In a specific embodiment, the application exemplifies the use of Hsp90 interacting moieties, e.g., inhibitors, as the binding moiety in the SDC-TRAPs. However, the invention is intended to include other binding moieties, including those that are contemplated, listed and exemplified herein. Accordingly, in certain embodiments directed to treating cancer or inflammation, the SDC-TRAP includes an Hsp90 inhibitor moiety conjugated to an effector moiety. In certain embodiments, the effector moiety is a cytotoxic effector moiety.

In another embodiment, the SDC-TRAP includes an effector moiety that is effective while still linked to the binding moiety. In such embodiment, cleavage of the bond or linker in the target cell is not a necessary feature of the invention. In other cases, such as cytotoxic effector moieties, the effector moiety should only be effective after the linker or bond is cleaved and the effector moiety is released from the SDC-TRAP molecule inside the target cell. In either case, SDC-TRAPs that do not enter into the target cell should be rapidly cleared (e.g., from the plasma or other non-target cells or tissues).

In another embodiment, the binding moiety of the SDC-TRAP binds a protein within the target cell, which may itself produce a desired biological effect (e.g., such as inhibiting Hsp90 within the target cell). In one embodiment, the binding moiety can contribute to the overall efficacy of the SDC-TRAP by not only binding an intracellular protein present in the target cell but by also conveying a particular desired biological effect. For example, if the binding moiety is an Hsp90 inhibitor and the target cell is a cancer cell, than the overall activity of the SDC-TRAP may not only result from the effector moiety, but also from the biological activity of the Hsp90 inhibitor.

Alternatively, interaction of the binding moiety with its protein target may not impart a biological effect, but rather only serve to attract and retain the SDC-TRAP within the target cell. In this embodiment, the binding moiety may reversibly bind to the intracellular target protein and create an intracellular equilibrium between free and bound SDC-TRAP molecules. This equilibrium may allow for cleavage of the SDC-TRAP and more effective delivery of the effector moiety, e.g., release of the effector moiety from the binding moiety by, for example, enzymatic cleavage, hydrolysis or degradation. In some cases, the effector moiety may be inactive until such release occurs.

In various aspects and embodiments, the present invention provides numerous advantages. For example, the SDC-TRAP can provide for targeted therapy, maximizing efficacy and/or minimizing undesired side effects. The SDC-TRAP can provide for targeted use of an effector moiety that would otherwise be unsuitable for administration alone due to toxicity and/or undesired systemic effects. The SDC-TRAP can facilitate targeting such effector moieties to intracellular targets—that is, due to its size and chemical properties, the SDC-TRAP can passively diffuse (or in some cases be actively transported) into a cell having an intracellular target of interest. Alternatively, the SDC-TRAP can deliver in a selective manner a cytotoxic molecule to destroy a target cell, such as a cancer or inflammatory cell.

In various aspects and embodiments, the SDC-TRAP can exhibit decreased and/or minimized toxicity concurrently with increased efficacy (e.g., as compared to that of the effector moiety when used alone). Decreasing and/or minimizing toxicity can encompass reducing toxicity to a predetermined level (e.g., a regulatory guideline or suggested level, for example promulgated by the US Food and Drug Administration "FDA"). Increasing efficacy can encompass increasing efficacy to a predetermined level (e.g., a regulatory guideline or suggested level, for example promulgated by the US FDA). Similarly, decreasing and/or minimizing toxicity concurrently with increasing efficacy can encompass achieving a predetermined therapeutic ratio (e.g., a regulatory guideline or suggested value, for example promulgated by the US FDA).

Decreasing and/or minimizing toxicity can encompass, for example, reducing toxicity by 5, 10, 15, 20, 25, 30, 35, 40, 45, 50, 55, 60, 65, 70, 75, 80, 85, 90, 95%, or more. Increasing efficacy can encompass, for example, increasing efficacy by 5, 10, 15, 20, 25, 30, 35, 40, 45, 50, 55, 60, 65, 70, 75, 80, 85, 90, 95, 100, 125, 150, 175, 200, 250, 300, 400, 500%, or more. Decreasing and/or minimizing toxicity concurrently with increasing efficacy can encompass, for example: essentially the same efficacy with decreased toxicity; essentially the same toxicity with increased efficacy; or decreased toxicity and increased efficacy. Similarly, decreasing and/or minimizing toxicity concurrently with increasing efficacy can encompass, for example, scenarios such as: increased efficacy enabling a lower dose (e.g., lower dose of effector moiety with a correspondingly lower net toxicity) and decreased toxicity enabling a higher dose (e.g., higher dose of effector moiety without a correspondingly higher net toxicity).

Additional advantages are discussed in detail below.

These and other advantages of the present invention are of particular interest, for example, in chemotherapy where despite tremendous recent advances, currently available therapeutics and therapies remains unsatisfactory and the prognosis for the majority of patients diagnosed with diseases such as cancer remains poor. However, while many of the illustrative embodiments and examples are presented in the context of cancer, a person of ordinary skill in the art would understand that the present invention has applications across therapeutic, diagnostic, and imaging applications that require, or would benefit from, targeting of an effector moiety.

In various aspects, the invention provides an SDC-TRAP comprising a binding moiety and an effector moiety.

In various aspects, the invention provides an SDC-TRAP comprising a binding moiety and an effector moiety, wherein the SDC-TRAP is able to enter a cell by active transport.

In various aspects, the invention provides an SDC-TRAP comprising a binding moiety and an effector moiety, wherein the SDC-TRAP has a molecular weight of less than about 1600 Daltons.

In various aspects, the invention provides an SDC-TRAP comprising a binding moiety and an effector moiety, wherein the binding moiety has a molecular weight of less than about 800 Daltons.

In various aspects, the invention provides an SDC-TRAP comprising a binding moiety and an effector moiety, wherein the effector moiety has a molecular weight of less than 800 Daltons.

In various aspects, the invention provides an SDC-TRAP comprising a binding moiety and an effector moiety, wherein the binding moiety and the effector moiety are approximately equal in size.

In various aspects, the invention provides an SDC-TRAP comprising an Hsp90 binding moiety and an effector moiety, wherein the Hsp90 binding moiety interacts with the N-terminal domain of Hsp90.

In various aspects, the invention provides an SDC-TRAP comprising an Hsp90 binding moiety and an effector moiety, wherein the Hsp90 binding moiety interacts with the C-terminal domain of Hsp90.

In various aspects, the invention provides an SDC-TRAP comprising an Hsp90 binding moiety and an effector moiety, wherein the Hsp90 binding moiety interacts with the middle domain of Hsp90.

In various aspects, the invention provides an SDC-TRAP comprising a binding moiety and an effector moiety, wherein the binding moiety interacts with a predetermined domain of a multidomain target protein molecule.

In various aspects, the invention provides an SDC-TRAP comprising a binding moiety (e.g., an Hsp90 binding moiety) and an effector moiety, wherein the binding moiety (e.g., Hsp90 binding moiety) has a $K_d$ of 100 nM or higher (e.g., for a predetermined target molecule, for example, Hsp90).

In various aspects, the invention provides an SDC-TRAP comprising a binding moiety (e.g., Hsp90 binding moiety) and an effector moiety, wherein when administered to a subject, the SDC-TRAP is present at a ratio of 2:1 in target (e.g., tumor) cells compared to plasma. In another embodiment, the invention provides an SDC-TRAP comprising a binding moiety (e.g., Hsp90 binding moiety) and an effector moiety, wherein when administered to a subject the SDC-TRAP present at a ratio of 2:1 in target (e.g., tumor) cells compared to normal cells.

In various aspects, the invention provides an SDC-TRAP comprising a binding moiety (e.g., Hsp90 binding moiety) and an effector moiety, wherein the SDC-TRAP is present in target (e.g., cancer) cells for at least 24 hours.

In various aspects, the invention provides an SDC-TRAP comprising a binding moiety (e.g., Hsp90 binding moiety) and an effector moiety, wherein the effector moiety is released for a period of at least 6 hours (e.g., within a target cell and/or tissue).

In various aspects, the invention provides an SDC-TRAP comprising a binding moiety (e.g., Hsp90 binding moiety) and an effector moiety, wherein the effector moiety is selectively released inside a target (e.g., cancer) cell.

In various aspects, the invention provides an SDC-TRAP comprising a binding moiety (e.g., Hsp90 binding moiety) and an effector moiety, wherein the SDC-TRAP allows for the use of an effector moiety that is toxic or otherwise unfit for administration to a subject.

In various aspects, the invention provides an SDC-TRAP comprising a binding moiety (e.g., Hsp90 binding moiety) and an effector moiety, wherein the Hsp90 is an inhibitor (e.g., Hsp90 inhibitor) that is ineffective as a therapeutic agent when administered alone.

In various aspects, the invention provides an SDC-TRAP comprising an Hsp90 binding moiety and an effector moiety.

In various aspects, the invention provides pharmaceutical compositions comprising a therapeutically effective amount of at least one SDC-TRAP, and at least one pharmaceutical excipient.

In various aspects, the invention provides methods for treating a subject in need thereof comprising administering a therapeutically effective amount of at least one SDC-TRAP to the subject, thereby treating the subject.

In various aspects, the invention provides methods for imaging, diagnosing, and/or selecting a subject comprising administering an effective amount of at least one SDC-TRAP to the subject, thereby imaging, diagnosing, and/or selecting the subject.

In various aspects, the invention provides kits for treating a subject in need thereof comprising at least one SDC-TRAP and instruction for administering a therapeutically effective amount of the at least one SDC-TRAP to the subject, thereby treating the subject.

In various aspects, the invention provides kits for imaging, diagnosing, and/or selecting a subject comprising at least one SDC-TRAP and instruction for administering an effective amount of at least one SDC-TRAP to the subject, thereby imaging, diagnosing, and/or selecting the subject.

In various embodiments, the invention can include any one or more of the aspects disclosed herein having any one or more of the features disclosed herein.

In various embodiments, the binding moiety interacts with a protein that is overexpressed in cancerous cells compared to normal cells.

In various embodiments, the protein is a chaperonin protein. The chaperonin can be, for example, Hsp90.

In various embodiments, the chaperonin is an Hsp90 binding moiety.

In various embodiments, the binding moiety is an Hsp90 ligand or a prodrug thereof. The Hsp90 ligand can be, for example, an Hsp90 inhibitor. An Hsp90 inhibitor can be selected from the group consisting of geldanamycins, macbecins, tripterins, tanespimycins, and radicicols.

In various embodiments, the binding moiety can be an Hsp90-targeting moiety, for example a triazole/resorcinol-based compound that binds Hsp90, or a resorcinol amide-based compound that binds Hsp90, e.g., ganetespib, AUY-922, or AT-13387.

In various embodiments, the binding moiety can be an Hsp90-binding compound of formula (I):

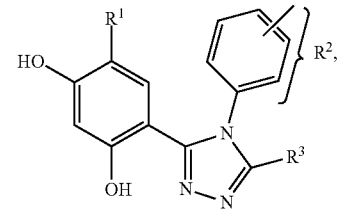

wherein
$R^1$ may be alkyl, aryl, halide, carboxamide or sulfonamide; $R^2$ may be alkyl, cycloalkyl, aryl or heteroaryl, wherein when $R^2$ is a six-membered aryl or heteroaryl, $R^2$ is substituted at the 3- and 4-positions relative to the connection point on the triazole ring, through which a linker L is attached; and $R^3$ may be SH, OH, —CONHR$^4$, aryl or heteroaryl, wherein when $R^3$ is a six-membered aryl or heteroaryl, $R^3$ is substituted at the 3 or 4 position.

In various embodiments, the binding moiety can be an Hsp90-binding compound of formula (II):

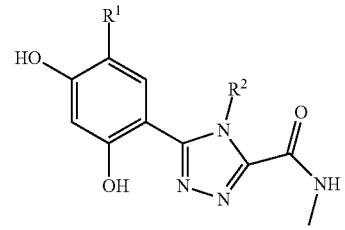

wherein
$R^1$ may be alkyl, aryl, halo, carboxamido, sulfonamido; and $R^2$ may be optionally substituted alkyl, cycloalkyl, aryl or heteroaryl. Examples of such compounds include 5-(2,4-dihydroxy-5-isopropylphenyl)-N-(2-morpholinoethyl)-4-(4-(morpholinomethyl)phenyl)-4H-1,2,4-triazole-3-carboxamide and 5-(2,4-dihydroxy-5-isopropylphenyl)-N-(4-(4-methylpiperazin-1-yl)phenyl)-N-(2,2,2-trifluoroethyl)-4H-1,2,4-triazole-3-carboxamide.

In various embodiments, the binding moiety can be an Hsp90-binding compound of formula (III):

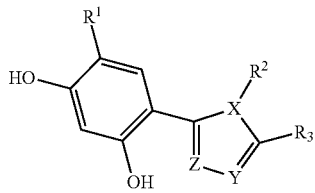

wherein
X, Y, and Z may independently be CH, N, O or S (with appropriate substitutions and satisfying the valency of the corresponding atoms and aromaticity of the ring); $R^1$ may be alkyl, aryl, halide, carboxamido or sulfonamido; $R^2$ may be substituted alkyl, cycloalkyl, aryl or heteroaryl, where a linker L is connected directly or to the extended substitutions on these rings; $R^3$ may be SH, OH, $NR^4R^5$ AND —$CONHR^6$, to which an effector moiety may be connected; $R^4$ and $R^5$ may independently be H, alkyl, aryl, or heteroaryl; and $R^6$ may be alkyl, aryl, or heteroaryl, having a minimum of one functional group to which an effector moiety may be connected.

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. The term "$(C_1-C_6)$alkyl" means a saturated straight chain or branched non-cyclic hydrocarbon having from 1 to 6 carbon atoms. Representative $(C_1-C_6)$alkyl groups are those shown above having from 1 to 6 carbon atoms. Alkyl groups included in compounds of this invention may be optionally substituted with one or more substituents.

As used herein, the term "alkenyl" means a saturated straight chain or branched non-cyclic hydrocarbon having from 2 to 10 carbon atoms and having at least one carbon-carbon double bond. Representative straight chain and branched $(C_2-C_{10})$alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

As used herein, the term "alkynyl" means a saturated straight chain or branched non-cyclic hydrocarbon having from 2 to 10 carbon atoms and having at least one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, the term "cycloalkyl" means a saturated, mono- or polycyclic alkyl radical having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, -cyclodecyl, octahydro-pentalenyl, and the like. Cycloalkyl groups may be optionally substituted with one or more substituents.

As used herein, the term "cycloalkenyl" means a mono- or poly-cyclic non-aromatic alkyl radical having at least one carbon-carbon double bond in the cyclic system and from 3 to 20 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl and the like. Cycloalkenyl groups may be optionally substituted with one or more substituents.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker.

As used herein, an "haloalkoxy" is an haloalkyl group which is attached to another moiety via an oxygen linker.

As used herein, the term an "aromatic ring" or "aryl" means a hydrocarbon monocyclic or polycyclic radical in which at least one ring is aromatic. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Aryl groups may be optionally substituted with one or more substituents. In one embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1-C_6)$alkylene group. Representative aralkyl groups include benzyl, 2-phenylethyl, naphth-3-yl-methyl and the like. Aralkyl groups may be optionally substituted with one or more substituents.

As used herein, the term "alkylene" refers to an alkyl group that has two points of attachment. The term "$(C_1-C_6)$alkylene" refers to an alkylene group that has from one to six carbon atoms. Straight chain $(C_1-C_6)$alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be optionally substituted with one or more substituents.

As used herein, the term "heterocyclyl" means a monocyclic (typically having 3- to 10-members) or a polycyclic (typically having 7- to 20-members) heterocyclic ring system which is either a saturated ring or a unsaturated non-aromatic ring. A 3- to 10-membered heterocycle can contain up to 5 heteroatoms; and a 7- to 20-membered heterocycle can contain up to 7 heteroatoms. Typically, a heterocycle has at least on carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents. Only stable isomers of such substituted heterocyclic groups are contemplated in this definition.

As used herein, the term "heteroaromatic", "heteroaryl" or like terms means a monocyclic or polycyclic heteroaromatic ring comprising carbon atom ring members and one or more heteroatom ring members. Each heteroatom is independently selected from nitrogen, which can be oxidized (e.g., N(O)) or quaternized; oxygen; and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring to another group may be at either a carbon atom or a heteroatom of the heteroaromatic or heteroaryl rings. Heteroaryl groups may be optionally substituted with one or more substituents.

As used herein, the term "($C_5$)heteroaryl" means an aromatic heterocyclic ring of 5 members, wherein at least one carbon atom of the ring is replaced with a heteroatom such as, for example, oxygen, sulfur or nitrogen. Representative ($C_5$)heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "($C_6$)heteroaryl" means an aromatic heterocyclic ring of 6 members, wherein at least one carbon atom of the ring is replaced with a heteroatom such as, for example, oxygen, nitrogen or sulfur. Representative ($C_6$)heteroaryls include pyridyl, pyridazinyl, pyrazinyl, triazinyl, tetrazinyl and the like.

As used herein, the term "heteroaralkyl" means a heteroaryl group that is attached to another group by a ($C_1$-$C_6$) alkylene. Representative heteroaralkyls include 2-(pyridin-4-yl)-propyl, 2-(thien-3-yl)-ethyl, imidazol-4-yl-methyl and the like. Heteroaralkyl groups may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroaralkyl groups include any substituent which will form a stable compound of the invention. Examples of substituents for an alkyl, alkylene, alkenyl, alkynyl, cycloalkyl, cycloalkenyl, heterocyclyl, aryl, aralkyl, heteroaryl, and heteroarylalkyl include an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, or a haloalkyl.

In addition, alkyl, cycloalkyl, alkylene, a heterocyclyl, and any saturated portion of a alkenyl, cycloalkenyl, alkynyl, aralkyl, and heteroaralkyl groups, may also be substituted with =O, or =S.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

As used herein, the term "lower" refers to a group having up to four atoms. For example, a "lower alkyl" refers to an alkyl radical having from 1 to 4 carbon atoms, "lower alkoxy" refers to "—O—($C_1$-$C_4$)alkyl and a "lower alkenyl" or "lower alkynyl" refers to an alkenyl or alkynyl radical having from 2 to 4 carbon atoms, respectively.

Unless indicated otherwise, the compounds of the invention containing reactive functional groups (such as (without limitation) carboxy, hydroxy, thiol, and amino moieties) also include protected derivatives thereof. "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

Exemplary Hsp90 inhibitors include those disclosed in U.S. Pat. Nos. 8,362,055 and 7,825,148. Examples of such compounds include AUY-922:

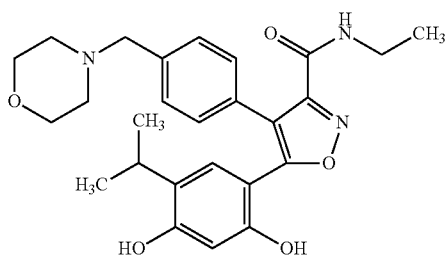 [SMILES: CCNC(=O)c1noc(-c2cc(C(C)C)c(O)cc2O)c1-c1ccc(CN2CCOCC2)cc1]

In various embodiments, the binding moiety can be an Hsp90-binding compound of formula (IV):

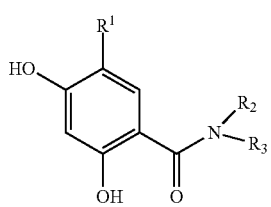

wherein

R[1] may be alkyl, aryl, halo, carboxamido or sulfonamido; R[2] and R[3] are independently $C_1$-$C_5$ hydrocarbyl groups optionally substituted with one or more of hydroxy, halogen, $C_1$-$C_2$ alkoxy, amino, mono- and di-$C_1$-$C_2$ alkylamino; 5- to 12-membered aryl or heteroaryl groups; or, R[2] and R[3], taken together with the nitrogen atom to which they are attached, form a 4- to 8-membered monocyclic heterocyclic group, of which up to 5 ring members are selected from O, N and S. Examples of such compounds include AT-13387:

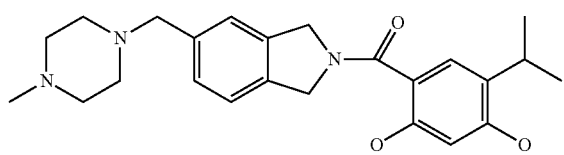

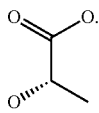

In various embodiments, the binding moiety includes an Hsp90-targeting moiety, for example one or more geldanamycins, e.g.,

IPI-493

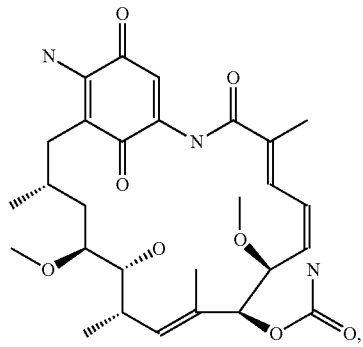

macbecins, tripterins, tanespimycins, e.g.,

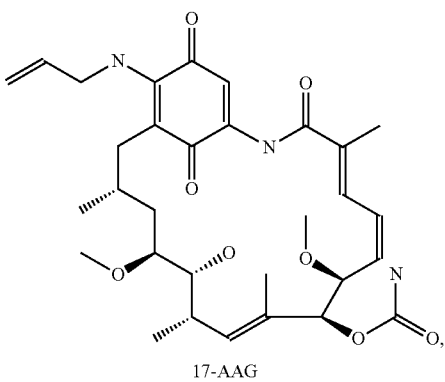

17-AAG

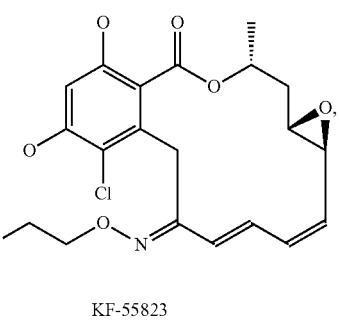

KF-55823

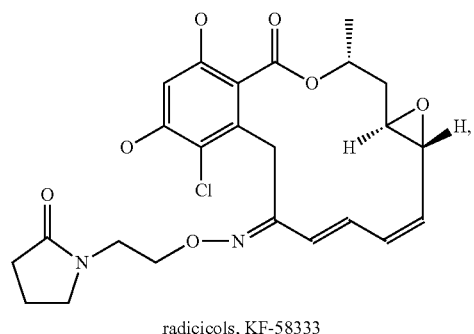

radicicols, KF-58333

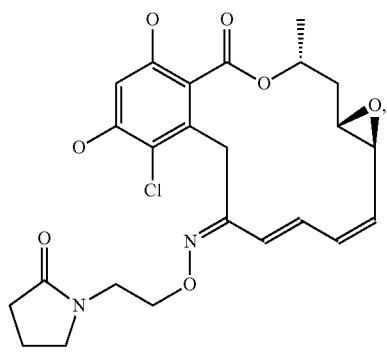

KF-58332

-continued
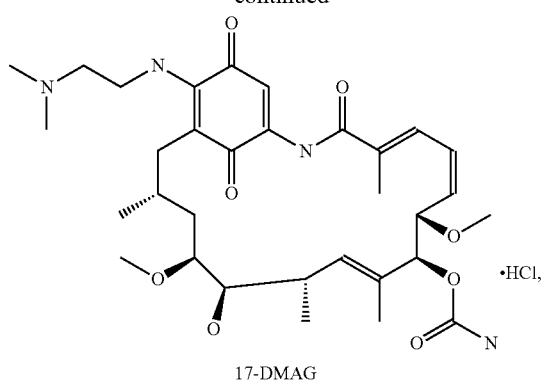
17-DMAG
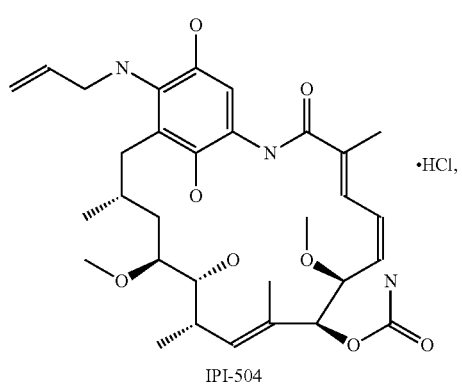
IPI-504
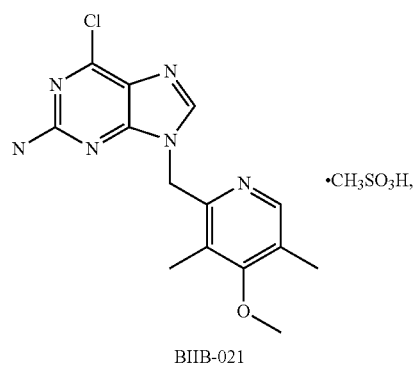
BIIB-021
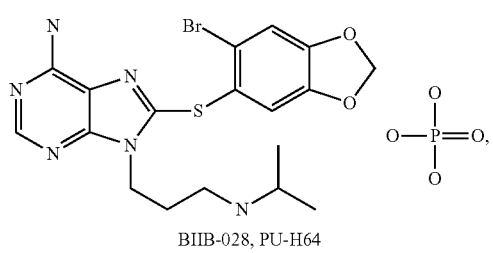
BIIB-028, PU-H64
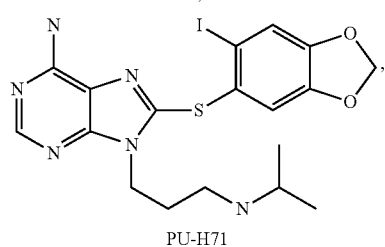
PU-H71
-continued
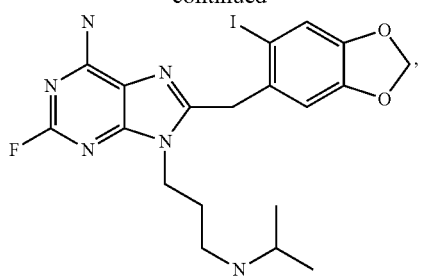
PU-DZ8
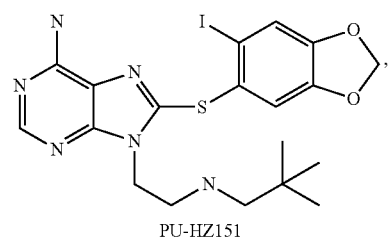
PU-HZ151
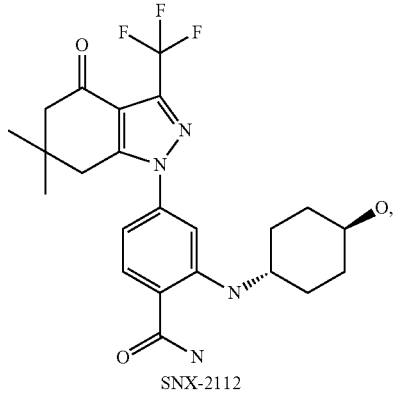
SNX-2112
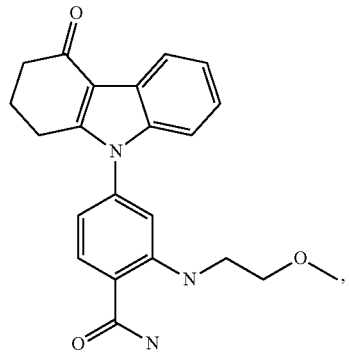
SNX-2321
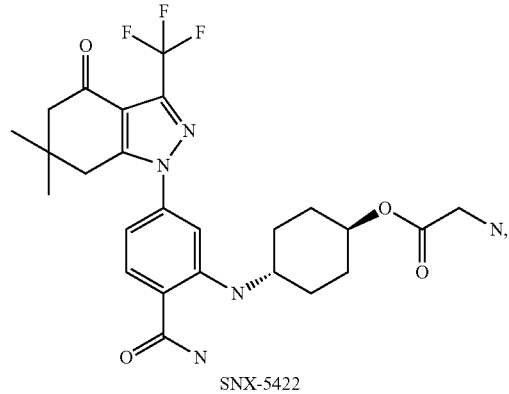
SNX-5422

-continued
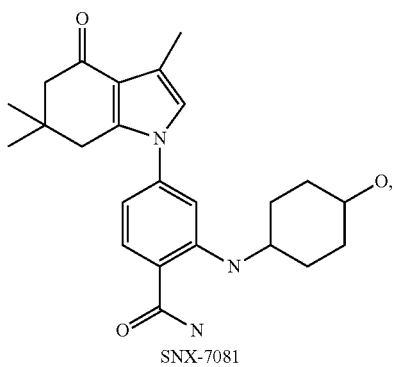
SNX-7081
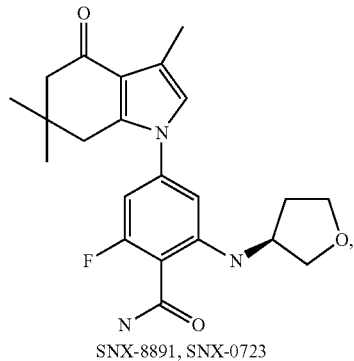
SNX-8891, SNX-0723
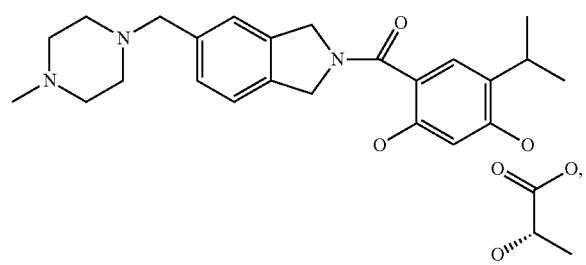
SAR-567530, ABI-287, ABI-328, AT-13387
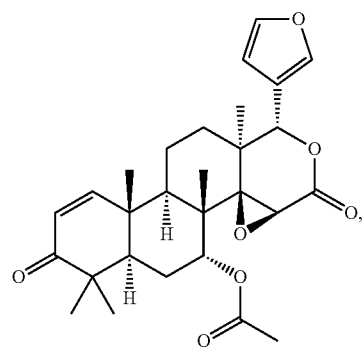
NSC-113497
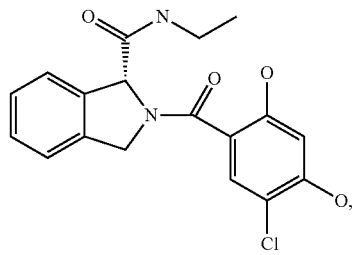
PF-3823863
-continued
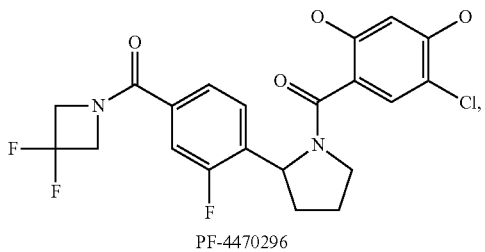
PF-4470296
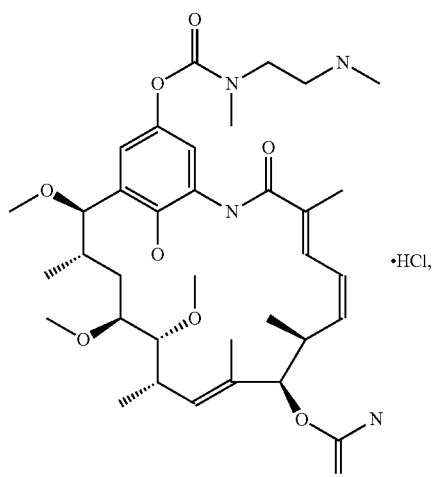
EC-102, EC-154, ARQ-250-RP, BC-274
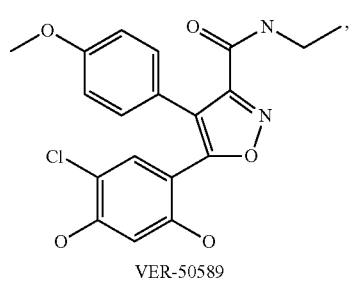
VER-50589
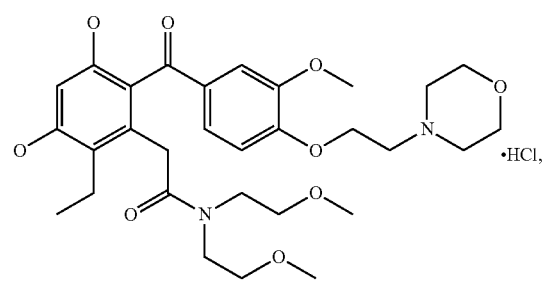
KW-2478
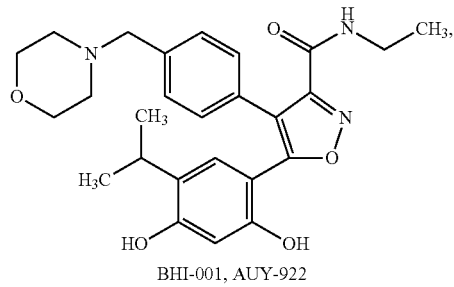
BHI-001, AUY-922

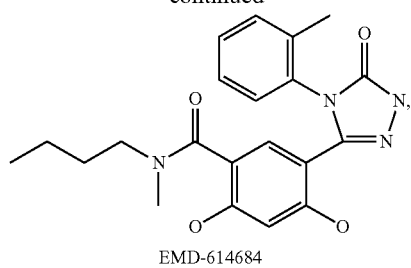
EMD-614684
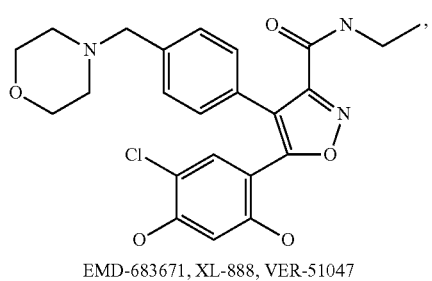
EMD-683671, XL-888, VER-51047
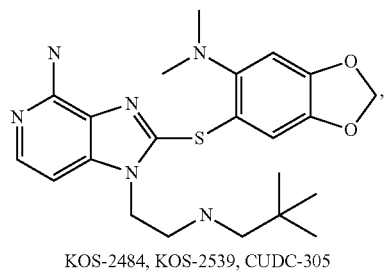
KOS-2484, KOS-2539, CUDC-305
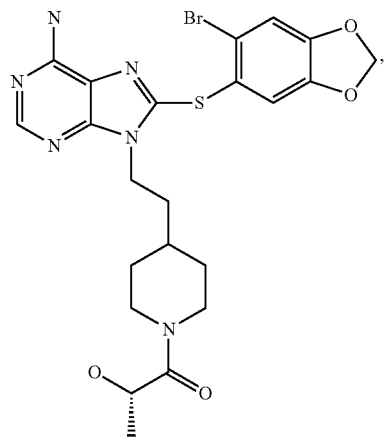
MPC-3100
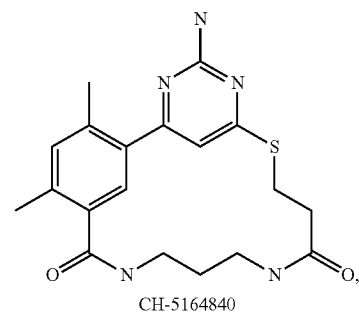
CH-5164840
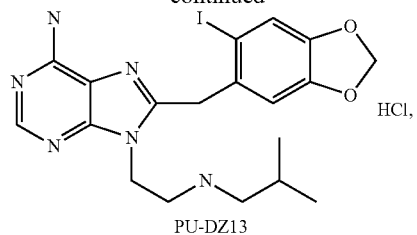
PU-DZ13
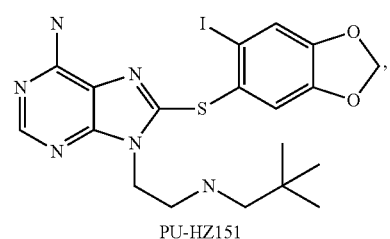
PU-HZ151
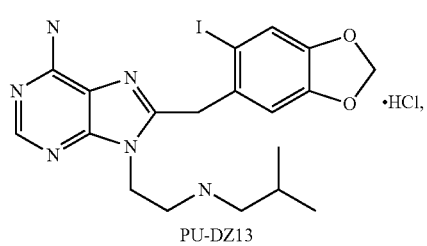
PU-DZ13
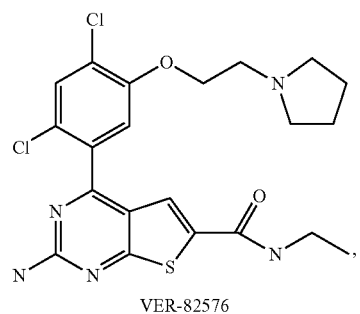
VER-82576
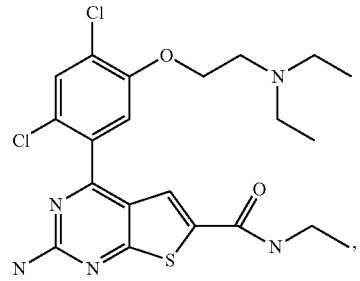
VER-82160
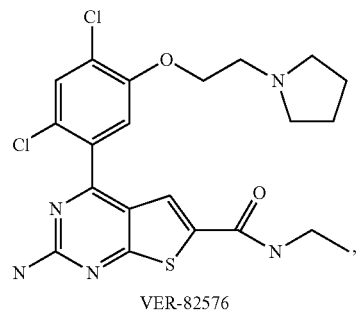
VER-82576

-continued

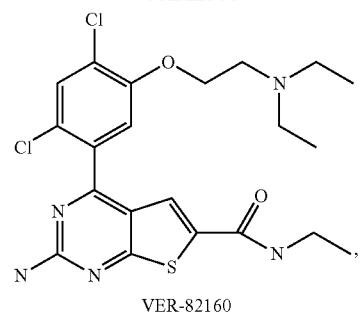
VER-82160

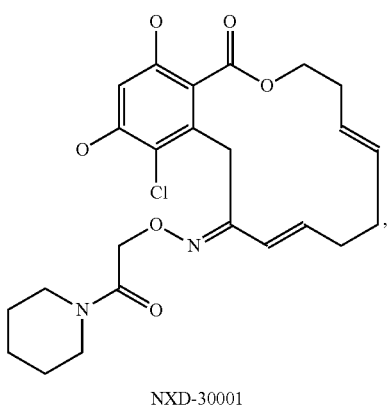
NXD-30001

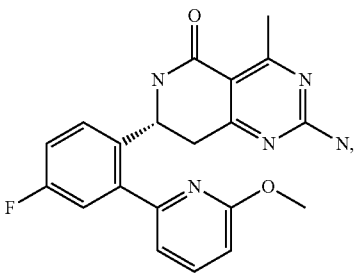
NVP-HSP990

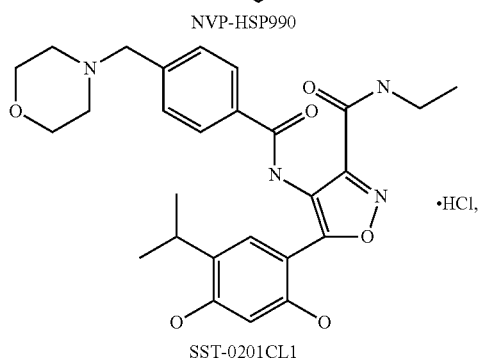
SST-0201CL1

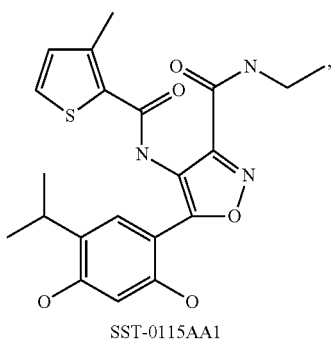
SST-0115AA1

-continued

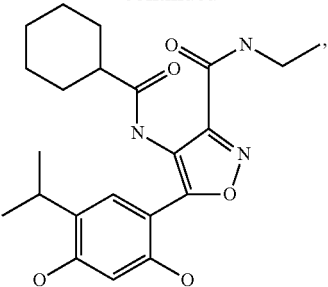
SST-0221AA1

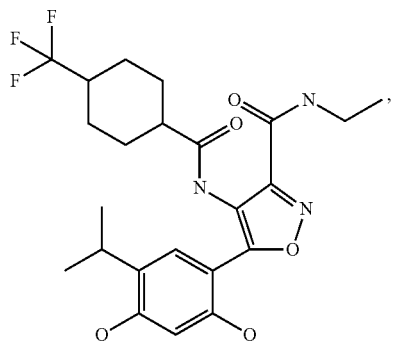
SST-0223AA1 novobiocin (a C-terminal Hsp90i.)

In various embodiments, the cytotoxic moiety is selected from the group consisting of bortezomib, ixazomib, and delanzomib.

In various embodiments, the cytotoxic moiety is not suitable for administration alone. The cytotoxic moiety can be unsuitable for administration alone due to toxicity. The cytotoxic moiety can be unsuitable for administration alone due to undesired targeting or a lack of targeting.

In various embodiments, the binding moiety and the effector moiety are covalently attached. The binding moiety and the effector moiety can be covalently attached, for example by a linker. The linker can comprise a cleavable linker. The cleavable linker can comprise an enzymatically cleavable linker. The linker can be selected from the group consisting of disulfide, carbamate, amide, ester, and ether linkers.

In various embodiments, the SDC-TRAP has a molecular weight of less than about 1600 Dalton. For example, the SDC-TRAP molecular weight can be less than about 1600, 1550, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, or 200 Dalton.

In various embodiments, the binding moiety has a molecular weight of less than about 800 Dalton. For example, the binding moiety molecular weight can be less than about 800, 750, 700, 650, 600, 550, 500, 450, 400, 350, 300, 250, 200, 150, or 100 Dalton.

In various embodiments, the effector moiety has a molecular weight of less than about 800 Dalton. For example, the effector moiety molecular weight can be less than about 800, 750, 700, 650, 600, 550, 500, 450, 400, 350, 300, 250, 200, 150, or 100 Dalton.

In various embodiments, the binding moiety and the effector moiety are approximately equal in size. For example, the binding moiety and the effector moiety can have less than about a 25, 50, 75, 100, 125, 150, 175, 200, 225, 250, 275, 300, 325, 350, 375, or 400 Dalton difference in molecular weight.

In various embodiments, the binding moiety has a high affinity for a molecular target. For example, the binding moiety has a high affinity for a molecular target that is a $K_d$ of 50, 100, 150, 200, 250, 300, 350, 400 nM or higher.

In various embodiments, when administered to a subject, the SDC-TRAP is present at a ratio of about 2:1, 5:1, 10:1, 25:1, 50:1, 75:1, 100:1, 150:1, 200:1, 250:1, 300:1, 400:1, 500:1, 600:1, 700:1, 800:1, 900:1, 1000:1, or greater. The ratio can be, for example, at 1, 2, 3, 4, 5, 6, 7, 8, 12, 24, 48, 72, or more hours from administration.

In various embodiments, the SDC-TRAP is present in target cells and/or tissue for at least 24 hours. The SDC-TRAP can be present in cancer cells for longer, for example, for at least 48, 72, 96, or 120 hours.

In various embodiments, the effector moiety is released for a period of at least 6 hours. The effector moiety can be released for a longer period, for example, for at least 12, 24, 48, 72, 96, or 120 hours.

In various embodiments, the effector moiety is selectively released inside a target cell and/or tissue.

In various embodiments, the present invention provides SDC-TRAP molecules comprising a binding moiety is an inhibitor of a target protein but that is ineffective as a therapeutic agent when administered alone. In these, and in other embodiments, the SDC-TRAP may facilitate an additive or synergistic effect between the binding moiety and effector moiety.

In various embodiments, the present invention provides method for treating a subject having a cancer comprising administering a therapeutically effective amount of at least one SDC-TRAP to the subject, thereby treating the cancer.

In various embodiments, the present invention provides a method for treating a subject having a colon cancer comprising administering a therapeutically effective amount of at least one SDC-TRAP to the subject, thereby treating the colon cancer.

In various embodiments, the present invention provides a method for treating a subject having a breast cancer comprising administering a therapeutically effective amount of at least one SDC-TRAP to the subject, thereby treating the breast cancer.

In various embodiments, the present invention provides a method for treating a subject having an ovarian cancer comprising administering a therapeutically effective amount of at least one SDC-TRAP to the subject, thereby treating the ovarian cancer.

In various embodiments, the present invention provides a method for treating a subject having a lung cancer comprising administering a therapeutically effective amount of at least one SDC-TRAP to the subject, thereby treating the lung cancer. The lung cancer can comprise small cell lung cancer.

In various embodiments, the present invention provides a method for treating a subject having a skin cancer comprising administering a therapeutically effective amount of at least one SDC-TRAP to the subject, thereby treating the skin cancer.

In various embodiments, the present invention provides a method for treating a subject having actinic keratosis comprising administering a therapeutically effective amount of at least one SDC-TRAP to the subject, thereby treating the actinic keratosis.

The present invention is described in further detail by the figures and examples below, which are used only for illustration purposes and are not limiting.

DETAILED DESCRIPTION OF THE INVENTION

Figure 1:
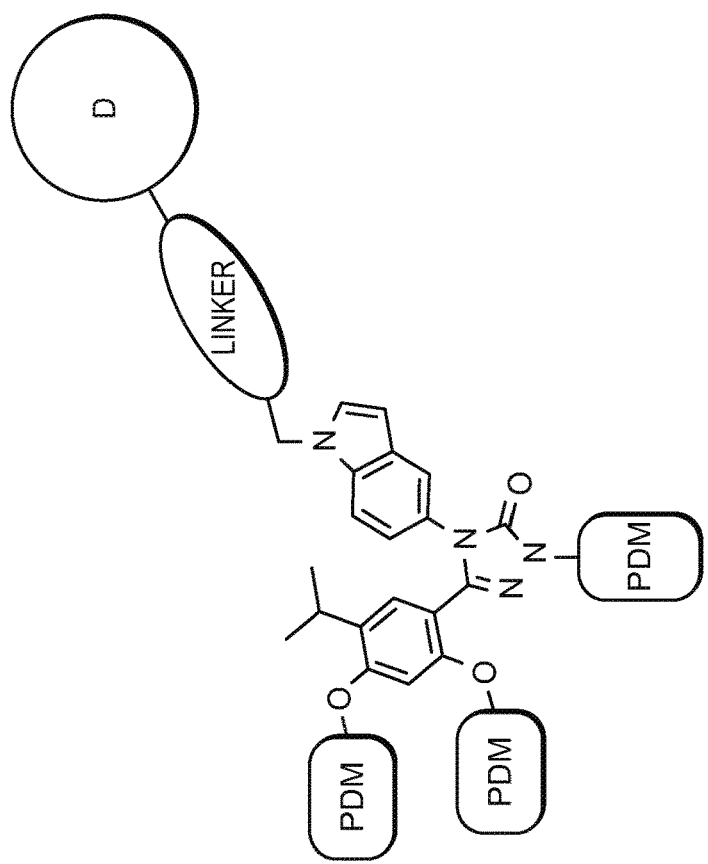
FIG. 1 shows how an illustrative Hsp90-targeting moiety may be suitably modified at one or more positions to enhance the physical, pharmacokinetic, or pharmacodynamic properties of the conjugate.
Figure 1:
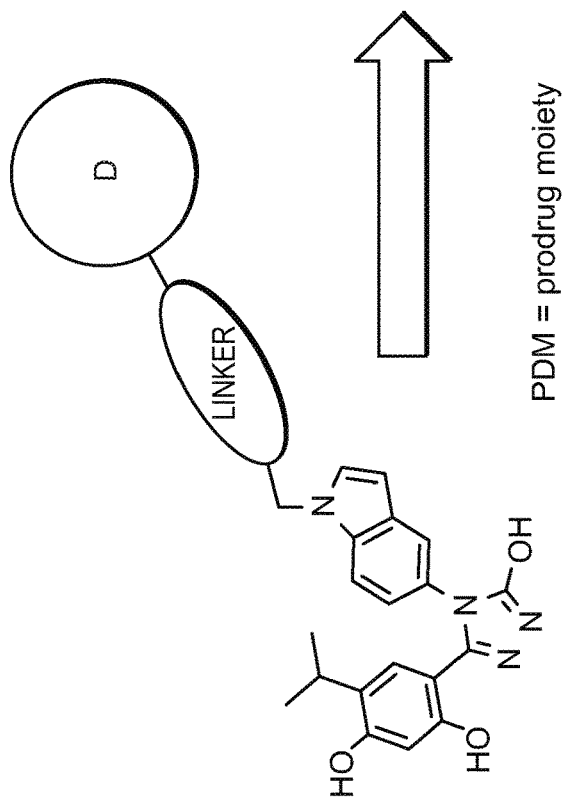
Figure 2:
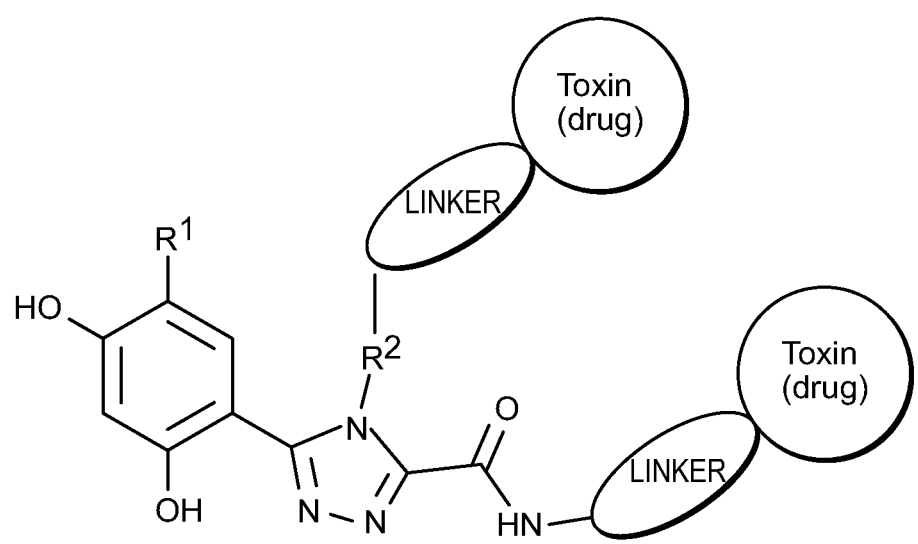
FIG. 2 illustrates an embodiment of a pharmaceutical conjugate having two effector moieties. Other features and advantages of the instant invention will be apparent from the following detailed description and claims.

The present invention provides molecules including an effector moiety conjugated to a binding moiety that directs the effector moiety to a biological target of interest. The molecules of the invention allow for selective targeting of an effector moiety by trapping the molecules of the invention in a desired cell, e.g., a cancer cell. The molecules can be described as Small molecule Drug Conjugates that are TRAPped intracellularly (SDC-TRAP), due to their selective binding to high concentration intracellular proteins. In order for the molecules of the invention to be trapped within the cells of interest, the binding moieties that are part of the SDC-TRAP molecules interact with proteins that are overexpressed in targeted cells. In exemplary embodiments, the proteins that are overexpressed are characteristic of a particular disease or disorder. In certain preferred embodiments of the invention, the small molecule drug conjugate includes a small molecule drug attached to an HSP90 inhibitor. Accordingly, the present invention provides compositions, kits, and methods (e.g., therapeutic, diagnostic, and imaging) that include the molecules of the invention.

In one embodiment of the invention, SDC-TRAPs allow for the delivery of a effector molecule that would otherwise be unsuitable for administration alone due to toxicity and/or undesired systemic effects. Using the targeted delivery molecules described herein (SDC-TRAPs) allows for effector moieties that are too toxic to administer by current methods to be dosed at lower levels thereby allowing the toxic effector to be targeted to specific diseased cells at sub-toxic levels.

In various exemplary aspects and embodiments, the present invention provides compounds for treating cancer. For example, an SDC-TRAP can comprise an Hsp90 binding moiety (i.e., targeting Hsp90, which is overexpressed in cancer cells compared to normal cells) and an effector moiety (e.g., the Hsp90 binding moiety can be an Hsp90 inhibitor that is conjugated to a cytotoxic agent). As indicated above, the invention is exemplified herein in terms of Hsp90-targeted binding moieties and cytotoxic agents. Other binding moieties that are contemplated, mentioned or described herein are intended to be included within the scope of the invention.

In various aspects and embodiments, the present invention provides an SDC-TRAP comprising a binding moiety and an effector moiety, wherein the SDC-TRAP molecule is able to enter a cell by passive transport. The ability of an SDC-TRAP to enter a cell by passive transport can be a result of one or more unique chemical properties of the SDC-TRAP (e.g., size, weight, charge, polarity, hydrophobicity, etc.) and can facilitate the delivery and/or action of the SDC-TRAP. The ability of an SDC-TRAP to enter a cell by passive transport is a functional property, which along with its physico-chemical properties, differentiates SDC-TRAPs from other targeted molecules such as antibody-drug conjugates.

In various aspects and embodiments, the present invention provides an SDC-TRAP comprising a binding moiety and an effector moiety, wherein SDC-TRAP molecule is able to enter a cell by active transport. The ability of an SDC-TRAP to enter a cell by active transport can be a result of one or more unique chemical properties of the SDC-TRAP and can facilitate the delivery and/or action of the SDC-TRAP. Example of SDC-TRAP active transport can include, for example, endocytosis, phagocytosis, pinocytosis, and exocytosis.

In various aspects and embodiments, the present invention provides an SDC-TRAP having a molecular weight of less than about 1600 Dalton (e.g., less than about 1600, 1550, 1500, 1450, 1400, 1350, 1300, 1250, 1200, 1150, 1100, 1050, 1000, 950, 900, 850, 800, 750, 700, 650, 600, 550, 500, 450, 400, 350, 300, 250, 200, etc.). Similarly, in various aspects and embodiments, the present invention provides a binding moiety having a molecular weight of less than about 800 Dalton (e.g., less than about 800, 750, 700, 650, 600, 550, 500, 450, 400, 350, 300, 250, 200, 150, 100, etc.) and/or an effector moiety having a molecular weight of less than about 800 Dalton (e.g., less than about 800, 750, 700, 650, 600, 550, 500, 450, 400, 350, 300, 250, 200, 150, 100, etc.). The overall molecular weight of an SDC-TRAP, and the individual weights of a binding moiety, effector moiety, and any linking moiety, can affect transport of the SDC-TRAP. In various examples, it has been observed that lower molecular weights can facilitate delivery and/or activity of an SDC-TRAP.

In various aspects and embodiments, the present invention provides an SDC-TRAP comprising an Hsp90 binding moiety and an effector moiety, wherein the Hsp90 binding moiety and the effector moiety are approximately equal in size (e.g., the Hsp90 binding moiety and the effector moiety have less than about a 25, 50, 75, 100, 125, 150, 175, 200, 225, 250, 275, 300, 325, 350, 375, 400, etc. Dalton difference in molecular weight.) In various examples, it has been observed that lower differences in molecular weight can facilitate delivery and/or activity of an SDC-TRAP.

In various aspects and embodiments, the present invention provides an SDC-TRAP comprising a target protein-interacting binding moiety. A target protein-interacting binding moiety can selectively interact with any one or more domains of a target protein. For example, where a target protein is Hsp90, the binding moiety can be an Hsp90 binding moiety that interacts with the N-terminal domain of Hsp90, the C-terminal domain of Hsp90, and/or the middle domain of Hsp90. Selective interaction with any one or more domains of a target protein can advantageously increase specificity and/or increase the concentration of molecular targets within a target tissue and/or cell.

In various aspects and embodiments, the present invention provides an SDC-TRAP comprising a binding moiety having a high affinity for a molecular target (e.g., a $K_d$ of 50, 100, 150, 200, 250, 300, 350, 400 nM or higher). For example, where a binding moiety is an Hsp90 binding moiety, the Hsp90 binding moiety can have a $K_d$ of 50, 100, 150, 200, 250, 300, 350, 400 nM or higher. A binding moiety having a high affinity for a molecular target can advantageously improve targeting and/or increase the resonance time of the SDC-TRAP in a target cell and/or tissue.

In various aspects and embodiments, the present invention provides an SDC-TRAP comprising a binding moiety (e.g., Hsp90 binding moiety) and an effector moiety, wherein when administered to a subject the SDC-TRAP is present at a ratio of about 2:1 in tumor cells compared to plasma. The ratio can be higher, for example, about 5:1, 10:1, 25:1, 50:1, 75:1, 100:1, 150:1, 200:1, 250:1, 300:1, 400:1, 500:1, 600:1, 700:1, 800:1, 900:1, 1000:1, or greater.

In various aspects and embodiments, the ratio is at 1, 2, 3, 4, 5, 6, 7, 8, 12, 24, 48, 72, or more hours from administration. The effectiveness of targeting can be reflected in the ratio of SDC-TRAP in a target cell and/or tissue compared to plasma.

In various aspects and embodiments, the present invention provides an SDC-TRAP comprising a binding moiety (e.g., Hsp90 binding moiety) and an effector moiety, wherein the SDC-TRAP is present in target (e.g., cancer) cells for at least 24 hours. The SDC-TRAP can be present in cancer cells for longer, for example, for at least 48, 72, 96, or 120 hours. It can be advantageous for an SDC-TRAP to be present in target cells for longer periods of time to increase the therapeutic effect of a given dose of SDC-TRAP and/or increase an interval between administrations of SDC-TRAP.

In various aspects and embodiments, the present invention provides an SDC-TRAP comprising a binding moiety (e.g., Hsp90 binding moiety) and an effector moiety, wherein the effector moiety is released for a period of at least 6 hours. The effector moiety can be released for a longer period, for example, for at least 12, 24, 48, 72, 96, or 120 hours. Selective release can be used to control, delay, and/or extend the period of release of an effector moiety and, therefore, increase the therapeutic effect of a given dose of SDC-TRAP, decrease the undesired side effects of a given dose of SDC-TRAP, and/or increase an interval between administrations of SDC-TRAP.

In various aspects and embodiments, the present invention provides an SDC-TRAP comprising an Hsp90 binding moiety and an effector moiety, wherein the effector moiety is selectively released inside a target (e.g., cancer) cell. Selective release can be achieved, for example, by a cleavable linker (e.g., an enzymatically cleavable linker). Selective release can be used to decrease undesired toxicity and/or unwanted side effects. For example, an SDC-TRAP can be designed where an effector moiety such is inactive (or relatively inactive) in a conjugated form, but active (or more active) after it is selectively released inside a target (e.g., cancer) cell.

In various aspects and embodiments, the present invention provides an SDC-TRAP comprising a binding moiety (e.g., Hsp90 binding moiety) and an effector moiety, wherein the SDC-TRAP allows for the use of an effector moiety that is otherwise toxic or unfit for administration to a subject. The effector moiety can be unfit for administration to a subject because of undesired toxicity. In such cases, a strategy such as selective release may be used to address the undesired toxicity. The effector moiety can be unfit for administration to a subject because of undesired targeting or a lack of targeting. Targeting can address such problems, for example, by minimizing systemic toxicity while maximizing local toxicity at a target (e.g., a tumor).

In various aspects and embodiments, the SDC-TRAP can exhibit decreased and/or minimized toxicity concurrently with increased efficacy (e.g., as compared to that of the effector moiety when used alone). Decreasing and/or minimizing toxicity can encompass reducing toxicity to a predetermined level (e.g., a regulatory guideline or suggested level, for example promulgated by the US Food and Drug Administration "FDA"). Increasing efficacy can encompass increasing efficacy to a predetermined level (e.g., a regulatory guideline or suggested level, for example promulgated by the US FDA). Similarly, decreasing and/or minimizing toxicity concurrently with increasing efficacy can encompass achieving a predetermined therapeutic ratio (e.g., a regulatory guideline or suggested value, for example promulgated by the US FDA).

Decreasing and/or minimizing toxicity can encompass, for example, reducing toxicity by 5, 10, 15, 20, 25, 30, 35, 40, 45, 50, 55, 60, 65, 70, 75, 80, 85, 90, 95%, or more. Increasing efficacy can encompass, for example, increasing efficacy by 5, 10, 15, 20, 25, 30, 35, 40, 45, 50, 55, 60, 65, 70, 75, 80, 85, 90, 95, 100, 125, 150, 175, 200, 250, 300, 400, 500%, or more. Decreasing and/or minimizing toxicity concurrently with increasing efficacy can encompass, for example: essentially the same efficacy with decreased toxicity; essentially the same toxicity with increased efficacy; or decreased toxicity and increased efficacy. Similarly, decreasing and/or minimizing toxicity concurrently with increasing efficacy can encompass, for example, scenarios such as: increased efficacy enabling a lower dose (e.g., lower dose of effector moiety with a correspondingly lower net toxicity) and decreased toxicity enabling a higher dose (e.g., higher dose of effector moiety without a correspondingly higher net toxicity).

In various aspects and embodiments, the present invention provides an SDC-TRAP comprising a binding moiety (e.g., Hsp90 binding moiety) and an effector moiety, wherein the binding moiety is an inhibitor (e.g., Hsp90 inhibitor) that is ineffective as a therapeutic agent when administered alone. In such cases, the SDC-TRAP may facilitate an additive or synergistic effect between the binding moiety and effector moiety, thereby advantageously improving the efficacy and/or reducing the side effects of a therapy.

In specific aspects and embodiments, the present invention provides an SDC-TRAP as set forth as SDC-TRAP-236 through SDC-TRAP-252 and methods of using the same for treatment of subject having cancer.

In order that the present invention may be more readily understood, certain terms are first defined. In addition, it should be noted that whenever a value or range of values of a parameter are recited, it is intended that values and ranges intermediate to the recited values are also intended to be part of this invention. Unless defined otherwise, all technical and scientific terms used herein have the same meaning as commonly understood to one of ordinary skill in the art to which this invention belongs. It is also to be understood that the terminology employed is for the purpose of describing particular embodiments, and is not intended to be limiting.

Definitions

The articles "a," "an," and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to."

The term "or" is used herein to mean, and is used interchangeably with, the term "and/or," unless context clearly indicates otherwise.

The term "such as" is used herein to mean, and is used interchangeably, with the phrase "such as but not limited to."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state, diminishing rate of or time to progression, and remission (whether partial or total), whether detectable or undetectable. "Treatment" can also mean prolonging survival as compared to expected survival in the absence of treatment. Treatment does not need to be curative.

A "therapeutically effective amount" is that amount sufficient to treat a disease in a subject. A therapeutically effective amount can be administered in one or more administrations.

By "diagnosing" and the like, as used herein, refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. Diagnostic methods provide an indicator that a disease is or is not present. A single diagnostic test typically does not provide a definitive conclusion regarding the disease state of the subject being tested.

The terms "administer," "administering" or "administration" include any method of delivery of a pharmaceutical composition or agent into a subject's system or to a particular region in or on a subject. In certain embodiments of the invention, an agent is administered intravenously, intramuscularly, subcutaneously, intradermally, intranasally, orally, transcutaneously, or mucosally. In a preferred embodiment, an agent is administered intravenously. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

As used herein, the term "survival" refers to the continuation of life of a subject which has been treated for a disease or condition, e.g., cancer. The time of survival can be defined from an arbitrary point such as time of entry into a clinical trial, time from completion or failure or an earlier treatment regimen, time from diagnosis, etc.

As used herein, the term "recur" refers to the re-growth of tumor or cancerous cells in a subject in whom primary treatment for the tumor has been administered. The tumor may recur in the original site or in another part of the body. In one embodiment, a tumor that recurs is of the same type as the original tumor for which the subject was treated. For example, if a subject had an ovarian cancer tumor, was treated and subsequently developed another ovarian cancer tumor, the tumor has recurred. In addition, a cancer can recur in or metastasize to a different organ or tissue than the one where it originally occurred.

As used herein, the terms "identify" or "select" refer to a choice in preference to another. In other words, to identify a subject or select a subject is to perform the active step of picking out that particular subject from a group and confirming the identity of the subject by name or other distinguishing feature.

As used herein, the term "benefit" refers to something that is advantageous or good, or an advantage. Similarly, the term "benefiting," as used herein, refers to something that improves or advantages. For example, a subject will benefit from treatment if they exhibit a decrease in at least one sign or symptom of a disease or condition (e.g., tumor shrinkage, decrease in tumor burden, inhibition or decrease of metastasis, improving quality of life ("QOL"), if there is a delay of time to progression ("TTP"), if there is an increase of overall survival ("OS"), etc.), or if there is a slowing or stopping of disease progression (e.g., halting tumor growth or metastasis, or slowing the rate of tumor growth or metastasis). A benefit can also include an improvement in quality of life, or an increase in survival time or progression free survival.

The terms "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/apoptosis, and certain characteristic morphological features. Cancer cells are often in the form of a solid tumor. However, cancer also includes non-solid tumors, e.g., blood tumors, e.g., leukemia, wherein the cancer cells are derived from bone marrow. As used herein, the term "cancer" includes pre-malignant as well as malignant cancers. Cancers include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, Burkitt's lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin, and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor. Other cancers include primary cancer, metastatic cancer, oropharyngeal cancer, hypopharyngeal cancer, liver cancer, gall bladder cancer, bile duct cancer, small intestine cancer, urinary tract cancer, kidney cancer, urothelium cancer, female genital tract cancer, uterine cancer, gestational trophoblastic disease, male genital tract cancer, seminal vesicle cancer, testicular cancer, germ cell tumors, endocrine gland tumors, thyroid cancer, adrenal cancer, pituitary gland cancer, hemangioma, sarcoma arising from bone and soft tissues, Kaposi's sarcoma, nerve cancer, ocular cancer, meningial cancer, glioblastomas, neuromas, neuroblastomas, Schwannomas, solid tumors arising from hematopoietic malignancies such as leukemias, metastatic melanoma, recurrent or persistent ovarian epithelial cancer, fallopian tube cancer, primary peritoneal cancer, gastrointestinal stromal tumors, colorectal cancer, gastric cancer, melanoma, glioblastoma multiforme, non-squamous non-small-cell lung cancer, malignant glioma, epithelial ovarian cancer, primary peritoneal serous cancer, metastatic liver cancer, neuroendocrine carcinoma, refractory malignancy, triple negative breast cancer, HER2-amplified breast cancer, nasopharageal cancer, oral cancer, biliary tract, hepatocellular carcinoma, squamous cell carcinomas of the head and neck (SCCHN), non-medullary thyroid carcinoma, recurrent glioblastoma multiforme, neurofibromatosis type 1, CNS cancer, liposarcoma, leiomyosarcoma, salivary gland cancer, mucosal melanoma, acral/lentiginous melanoma, paraganglioma, pheochromocytoma, advanced metastatic cancer, solid tumor, triple negative breast cancer, colorectal cancer, sarcoma, melanoma, renal carcinoma, endometrial cancer, thyroid cancer, rhabdomysarcoma, multiple myeloma, ovarian cancer, glioblastoma, gastrointestinal stromal tumor, mantle cell lymphoma, and refractory malignancy.

"Solid tumor," as used herein, is understood as any pathogenic tumor that can be palpated or detected using imaging methods as an abnormal growth having three dimensions. A solid tumor is differentiated from a blood tumor such as leukemia. However, cells of a blood tumor are derived from bone marrow; therefore, the tissue producing the cancer cells is a solid tissue that can be hypoxic.

"Tumor tissue" is understood as cells, extracellular matrix, and other naturally occurring components associated with the solid tumor.

As used herein, the term "isolated" refers to a preparation that is substantially free (e.g., 50%, 60%, 70%, 80%, 90% or more, by weight) from other proteins, nucleic acids, or compounds associated with the tissue from which the preparation is obtained.

The term "sample" as used herein refers to a collection of similar fluids, cells, or tissues isolated from a subject. The term "sample" includes any body fluid (e.g., urine, serum, blood fluids, lymph, gynecological fluids, cystic fluid, ascetic fluid, ocular fluids, and fluids collected by bronchial lavage and/or peritoneal rinsing), ascites, tissue samples (e.g., tumor samples) or a cell from a subject. Other subject samples include tear drops, serum, cerebrospinal fluid, feces, sputum, and cell extracts. In one embodiment, the sample is removed from the subject. In a particular embodiment, the sample is urine or serum. In another embodiment, the sample does not include ascites or is not an ascites sample. In another embodiment, the sample does not include peritoneal fluid or is not peritoneal fluid. In one embodiment, the sample comprises cells. In another embodiment, the sample does not comprise cells. Samples are typically removed from the subject prior to analysis. However, tumor samples can be analyzed in the subject, for example, using imaging or other detection methods.

The term "control sample," as used herein, refers to any clinically relevant comparative sample, including, for example, a sample from a healthy subject not afflicted with cancer, a sample from a subject having a less severe or slower progressing cancer than the subject to be assessed, a sample from a subject having some other type of cancer or disease, a sample from a subject prior to treatment, a sample of non-diseased tissue (e.g., non-tumor tissue), a sample from the same origin and close to the tumor site, and the like. A control sample can be a purified sample, protein, and/or nucleic acid provided with a kit. Such control samples can be diluted, for example, in a dilution series to allow for quantitative measurement of analytes in test samples. A control sample may include a sample derived from one or more subjects. A control sample may also be a sample made at an earlier time point from the subject to be assessed. For example, the control sample could be a sample taken from the subject to be assessed before the onset of the cancer, at an earlier stage of disease, or before the administration of treatment or of a portion of treatment. The control sample may also be a sample from an animal model, or from a tissue or cell lines derived from the animal model, of the cancer. The level in a control sample that consists of a group of measurements may be determined, e.g., based on any appropriate statistical measure, such as, for example, measures of central tendency including average, median, or modal values.

As used herein, the term "obtaining" is understood herein as manufacturing, purchasing, or otherwise coming into possession of.

As used herein, the term "identical" or "identity" is used herein in relation to amino acid or nucleic acid sequences refers to any gene or protein sequence that bears at least 30% identity, more preferably 40%, 50%, 60%, 70%, 75%, 80%, 81%, 82%, 83%, 84%, 85%, 86%, 87%, 88%, 89%, 90%, 91%, 92%, 93%, 94%, and most preferably 95%, 96%, 97%, 98%, 99% or more identity to a known gene or protein sequence over the length of the comparison sequence. Protein or nucleic acid sequences with high levels of identity throughout the sequence can be said to be homologous. A "homologous" protein can also have at least one biological activity of the comparison protein. In general, for proteins, the length of comparison sequences will be at least 10 amino acids, preferably 10, 20, 30, 40, 50, 60, 70, 80, 90, 100, 150, 175, 200, 250, or at least 300 amino acids or more. For nucleic acids, the length of comparison sequences will generally be at least 25, 50, 100, 125, 150, 200, 250, 300, 350, 400, 450, 500, 550, 600, 650, 700, 800, or at least 850 nucleotides or more.

As used herein, "detecting," "detection" and the like are understood that an assay performed for identification of a specific analyte in a sample. The amount of analyte or activity detected in the sample can be none or below the level of detection of the assay or method.

The terms "modulate" or "modulation" refer to upregulation (i.e., activation or stimulation), downregulation (i.e., inhibition or suppression) of a level, or the two in combination or apart. A "modulator" is a compound or molecule that modulates, and may be, e.g., an agonist, antagonist, activator, stimulator, suppressor, or inhibitor.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

As used herein, "level of activity" is understood as the amount of protein activity, typically enzymatic activity, as determined by a quantitative, semi-quantitative, or qualitative assay. Activity is typically determined by monitoring the amount of product produced in an assay using a substrate that produces a readily detectable product, e.g., colored product, fluorescent product, or radioactive product.

As used herein, "changed as compared to a control" sample or subject is understood as having a level of the analyte or diagnostic or therapeutic indicator (e.g., marker) to be detected at a level that is statistically different than a sample from a normal, untreated, or control sample control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g., β-galactosidase or luciferase). Depending on the method used for detection the amount and measurement of the change can vary. Changed as compared to a control reference sample can also include a change in one or more signs or symptoms associated with or diagnostic of disease, e.g., cancer. Determination of statistical significance is within the ability of those skilled in the art, e.g., the number of standard deviations from the mean that constitute a positive result.

"Elevated" or "lower" refers to a patient's value of a marker relative to the upper limit of normal ("ULN") or the lower limit of normal ("LLN") which are based on historical normal control samples. As the level of the marker present in the subject will be a result of the disease, and not a result of treatment, typically a control sample obtained from the patient prior to onset of the disease will not likely be available. Because different labs may have different absolute results, values are presented relative to that lab's upper limit of normal value (ULN).

The "normal" level of expression of a marker is the level of expression of the marker in cells of a subject or patient not afflicted with cancer. In one embodiment, a "normal" level of expression refers to the level of expression of the marker under normoxic conditions.

An "over-expression" or "high level of expression" of a marker refers to an expression level in a test sample that is greater than the standard error of the assay employed to assess expression, and is preferably at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 4, 5, 6, 7, 8, 9, or 10 times the expression level of the marker in a control sample (e.g., sample from a healthy subject not having the marker associated disease, i.e., cancer). In one embodiment, expression of a marker is compared to an average expression level of the marker in several control samples.

A "low level of expression" or "under-expression" of a marker refers to an expression level in a test sample that is less than at least 0.9, 0.8, 0.7, 0.6, 0.5, 0.4, 0.3, 0.2, or 0.1 times the expression level of the marker in a control sample (e.g., sample from a healthy subject not having the marker associated disease, i.e., cancer). In one embodiment, expression of a marker is compared to an average expression level of the marker in several control samples.

As used herein, "binding" is understood as having at least a $10^2$ or more, $10^3$ or more, preferably $10^4$ or more, preferably $10^5$ or more, preferably $10^6$ or more preference for binding to a specific binding partner as compared to a non-specific binding partner (e.g., binding an antigen to a sample known to contain the cognate antibody).

"Determining" as used herein is understood as performing an assay or using a diagnostic method to ascertain the state of someone or something, e.g., the presence, absence, level, or degree of a certain condition, biomarker, disease state, or physiological condition.

"Prescribing" as used herein is understood as indicating a specific agent or agents for administration to a subject.

As used herein, the terms "respond" or "response" are understood as having a positive response to treatment with a therapeutic agent, wherein a positive response is understood as having a decrease in at least one sign or symptom of a disease or condition (e.g., tumor shrinkage, decrease in tumor burden, inhibition or decrease of metastasis, improving quality of life ("QOL"), delay of time to progression ("TTP"), increase of overall survival ("OS"), etc.), or slowing or stopping of disease progression (e.g., halting tumor growth or metastasis, or slowing the rate of tumor growth or metastasis). A response can also include an improvement in quality of life, or an increase in survival time or progression free survival.

The terms "administer," "administering" or "administration" can include any method of delivery of a pharmaceutical composition or agent into a subject's system or to a particular region in or on a subject. In certain embodiments of the invention, an Hsp90 inhibitor is administered intravenously, intramuscularly, subcutaneously, intradermally, intranasally, orally, transcutaneously, or mucosally. In a preferred embodiment, an agent is administered intravenously. Administering can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

As used herein, the term "high concentration" refers to the concentration of SDC-TRAP that accumulates in target cells of the invention due to the selective binding of the binding moiety of the SDC-TRAP to the target protein. In one embodiment, the concentration is higher than in similar cells that do not overexpress the target protein, e.g., lung cancer cells as compared to non-cancerous lung cells. In another embodiment, the concentration is higher in target cells compared to cells that do not express, or overexpress, the target protein. In exemplary embodiments, the high concentration is 1.5, 2, 3, 4, 5, 10, 15, 20, 50, 100, 1000 times or more than cells that are not targeted by the SDC-TRAP molecules of the invention.

The term "moiety" refers generally to a portion of a molecule, which may be a functional group, a set of functional groups, and/or a specific group of atoms within a molecule, that is responsible for a characteristic chemical, biological, and/or medicinal property of the molecule.

The term "binding moiety" refers to low molecular weight (e.g., less than about 800, 700, 600, 500, 400, 300, 200, or 100 etc. Dalton) organic compounds, which may serve as a therapeutic or a regulator of a biological process. Binding moieties include molecules that can bind to a biopolymer such as protein, nucleic acid, or polysaccharide and acts as an effector, altering the activity or function of the biopolymer. Binding moieties can have a variety of biological functions, serving as cell signaling molecules, as tools in molecular biology, as drugs in medicine, as pesticides in farming, and in many other roles. These compounds can be natural (such as secondary metabolites) or artificial (such as antiviral drugs); they may have a beneficial effect against a disease (such as drugs) or may be detrimental (such as teratogens and carcinogens). Biopolymers such as nucleic acids, proteins, and polysaccharides (such as starch or cellulose) are not binding moieties, although their constituent monomers—ribo- or deoxyribo-nucleotides, amino acids, and monosaccharides, respectively—are often considered to be. Small oligomers are also usually considered binding moieties, such as dinucleotides, peptides such as the antioxidant glutathione, and disaccharides such as sucrose.

As used herein, a "protein interacting binding moiety" or "binding moiety" refers to a binding moiety, or portion thereof, that interacts with a predetermined target. The interaction is achieved through some degree of specificity and/or affinity for the target. Both specificity and affinity is generally desirable, although in certain cases higher specificity may compensate for lower affinity and higher affinity may compensate for lower specificity. Affinity and specificity requirements will vary depending upon various factors including, but not limited to, absolute concentration of the target, relative concentration of the target (e.g., in cancer vs. normal cells), potency and toxicity, route of administration, and/or diffusion or transport into a target cell. The target can be a molecule of interest and/or localized in an area of interest. For example, the target can be a therapeutic target and/or localized in an area targeted for a therapy (e.g., a protein that is overexpressed in cancerous cells, as compared to normal cells). In one particular example, a target can be a chaperonin protein such as Hsp90 and the binding moiety can be an Hsp90 binding moiety (e.g., therapeutic, cytotoxic, or imaging moiety). Preferentially, the binding moiety will enhance, be compatible with, or not substantially reduce, passive transport of a conjugate including the binding moiety into a cell, e.g., a cell comprising a target protein.

The term "effector moiety" refers to a molecule, or portion thereof, that has an effect on a target and/or proximally to the target. In various preferred embodiments, the effector moiety is a binding moiety, or portion thereof. An effect can include, but is not limited to, a therapeutic effect, an imaging effect, and/or a cytotoxic effect. At a molecular or cellular level, an effect can include, but is not limited to, promotion or inhibition of the target's activity, labeling of the target, and/or cell death. Preferentially, the effector moiety will enhance, be compatible with, or not substantially reduce, passive transport of a conjugate including the effector moiety into a cell comprising a target. Different effector moieties can be used together and therapeutics in accordance with the present invention may include more than one effector moiety (e.g., two or more different (or same) effector moieties in a single therapeutic in accordance with the present invention, two or more different therapeutics in accordance with the present invention including different effector moieties).

In some embodiments, the effector moiety is selected from the group consisting of bortezomib, ixazomib, and delanzomib.

The term "small molecule drug conjugate that is trapped intracellularly" or "binding moiety drug conjugate that is trapped intracellularly" or "SDC-TRAP" refers to a binding moiety and effector moiety joined to one another, or acting as if joined to one another. A binding moiety and effector moiety can be joined through essentially any chemical or physical force, either directly (e.g., binding moiety and effector moiety viewed as two moieties on the same molecule, or a single moiety having both functions) or through an intermediate (e.g., linker). For example, a binding moiety and effector moiety can be joined by one or more covalent bonds, ionic bonds, hydrogen bonds, the hydrophobic effect, dipole-dipole forces, ion-dipole forces, dipole-induced dipole forces, instantaneous dipole-induced dipole forces, and/or combinations thereof. Preferentially, the SDC-TRAP will be capable of passive and/or active transport into a cell comprising a target. Moreover, SDC-TRAP molecules of the invention may comprise multiple effector molecules conjugated to the binding moiety.

The term "linker" or "linking moiety," as used herein in the context of binding moiety, effector moieties, and/or SDC-TRAPs refers to a chemical moiety that joins two other moieties (e.g., a binding moiety and an effector moiety). A linker can covalently join a binding moiety and an effector moiety. A linker can include a cleavable linker, for example an enzymatically cleavable linker. A linker can include a disulfide, carbamate, amide, ester, and/or ether linkers.

In some embodiments, the linker or linking moiety of an SDC-TRAP can be advantageous when compared to the limited linking chemistry of antibody-drug conjugates (ADC). For example, unlike ADCs that are limited by the need to maintain the structure and/or stability of an antibody, SDC-TRAPs can use a wider range of linking chemistries and/or solvents (e.g., that can alter, distort, or denature an antibody).

As used herein, a "ligand" is a substance (e.g., a binding moiety) that can form a complex with a biomolecule. The ligand and/or formation of the ligand-biomolecule complex can have a biological or chemical effect, such as a therapeutic effect, cytotoxic effect, and/or imaging effect.

As used herein, a "prodrug" is a pharmacological substance that is administered in an inactive or less than fully active form and that is subsequently converted to an active pharmacological agent (i.e., the drug) through a metabolic processes. Prodrugs can be used to improve how the intended drug is absorbed, distributed, metabolized, and/or excreted. A prodrug may also be used to improve how selectively the intended drug interacts with cells or processes that are not its intended target (e.g., to reduce adverse or unintended effects of the intended drug, for example a chemotherapy drug).

The phrase "Hsp90 ligand or a prodrug thereof" refers generally to molecules that bind to and in some cases effect Hsp90, and inactive forms (i.e., prodrugs) thereof. An Hsp90 ligand can be an "Hsp90 inhibitor," which is understood as a therapeutic agent that reduces the activity of Hsp90 either by directly interacting with Hsp90 or by, for example, preventing the formation of the Hsp90/CDC37 complex such that the expression and proper folding of at least one client protein of Hsp90 is inhibited. "Hsp90" includes each member of the family of heat shock proteins having a mass of about 90-kilodaltons. For example, in humans the highly conserved Hsp90 family includes cytosolic Hsp90$^\alpha$ and Hsp90$^\beta$ isoforms, as well as GRP94, which is found in the endoplasmic reticulum, and HSP75/TRAP1, which is found in the mitochondrial matrix. As used herein, Hsp90 inhibitors include, but are not limited to ganetespib, geldanamycin (tanespimycin), e.g., IPI-493, macbecins, tripterins, tanespimycins, e.g., 17-AAG (alvespimycin), KF-55823, radicicols, KF-58333, KF-58332, 17-DMAG, IPI-504, BIIB-021, BIIB-028, PU-H64, PU-H71, PU-DZ8, PU-HZ151, SNX-2112, SNX-2321, SNX-5422, SNX-7081, SNX-8891, SNX-0723, SAR-567530, ABI-287, ABI-328, AT-13387, NSC-113497, PF-3823863, PF-4470296, EC-102, EC-154, ARQ-250-RP, BC-274, VER-50589, KW-2478, BHI-001, AUY-922, EMD-614684, EMD-683671, XL-888, VER-51047, KOS-2484, KOS-2539, CUDC-305, MPC-3100, CH-5164840, PU-DZ13, PU-HZ151, PU-DZ13, VER-82576, VER-82160, VER-82576, VER-82160, NXD-30001, NVP-HSP990, SST-0201CL1, SST-0115AA1, SST-0221AA1, SST-0223AA1, novobiocin (a C-terminal Hsp90i, herbinmycin A, radicicol, CCT018059, PU-H71, or celastrol.

The term "therapeutic moiety" refers to molecule, compound, or fragment thereof that is used for the treatment of a disease or for improving the well-being of an organism or that otherwise exhibit healing power (e.g., pharmaceuticals, drugs, and the like). A therapeutic moiety can be a chemical, or fragment thereof, of natural or synthetic origin used for its specific action against disease, for example cancer. Therapeutic agents used for treating cancer may be called chemotherapeutic agents. As described herein, a therapeutic moiety is preferentially a small molecule. Exemplary small molecule therapeutics include those that are less than 800 Daltons, 700 Daltons, 600 Daltons, 500 Daltons, 400 Daltons, or 300 Daltons.

The term "cytotoxic moiety" refers to molecule, compound, or fragment thereof that has a toxic or poisonous effect on cells, or that kills cells. Chemotherapy and radiotherapy are forms of cytotoxic therapy. Treating cells with a cytotoxic moiety can produce a variety of results—cells may undergo necrosis, stop actively growing and dividing, or activate a genetic program of controlled cell death (i.e., apoptosis). Examples of cytotoxic moieties include, but are not limited to, SN-38, bendamustine, VDA, doxorubicin, pemetrexed, vorinostat, lenalidomide, irinotecan, ganetespib, docetaxel, 17-AAG, 5-FU, abiraterone, crizotinib, KW-2189, BUMB2, DC1, CC-1065, adozelesin, or fragment(s) thereof.

The term "imaging moiety" refers to a molecule, compound, or fragment thereof that facilitates a technique and/or process used to create images or take measurements of a cell, tissue, and/or organism (or parts or functions thereof) for clinical and/or research purposes. An imaging moiety can produce, for example, a signal through emission and/or interaction with electromagnetic, nuclear, and/or mechanical (e.g., acoustic as in ultrasound) energy. An imaging moiety can be used, for example, in various radiology, nuclear medicine, endoscopy, thermography, photography, spectroscopy, and microscopy methods.

"Pharmaceutical conjugate" refers to a non-naturally occurring molecule that includes a binding moiety (e.g., an Hsp90-targeting moiety) associated with an effector moiety, where these two components may also be covalently bonded to each other either directly or through a linking group.

The term "drug" refers to any active agent that affects any biological process. Active agents that are considered drugs for purposes of this application are agents that exhibit a pharmacological activity. Examples of drugs include active agents that are used in the prevention, diagnosis, alleviation, treatment or cure of a disease condition.

By "pharmacologic activity" is meant an activity that modulates or alters a biological process so as to result in a phenotypic change, e.g., cell death, cell proliferation etc.

By "pharmacokinetic property" is meant a parameter that describes the disposition of an active agent in an organism or host.

By "half-life" is meant the time for one-half of an administered drug to be eliminated through biological processes, e.g., metabolism, excretion, etc.

The term "efficacy" refers to the effectiveness of a particular active agent for its intended purpose, i.e., the ability of a given active agent to cause its desired pharmacologic effect.

Binding Moiety-Effector Moiety Drug Conjugates that are Trapped Intracellularly (SDC-TRAPs)

The present invention provides SDC-TRAPs, as well as SDC-TRAP compositions, kits, and methods of use thereof. SDC-TRAPs include a binding moiety (e.g., a binding moiety such as a ligand) conjugated to an effector moiety (e.g., a pharmacological agent such as a drug or imaging agent). These two moieties can be joined by a linker, e.g., a covalently-bonded linking group. SDC-TRAPs are useful in a variety of therapeutic, imaging, diagnostic, and/or research applications. In one illustrative example of cancer therapy, an SDC-TRAP can be a pharmaceutical conjugate of an Hsp90-binding moiety such as an Hsp90 ligand or inhibitor associated with an effector moiety such as a therapeutic or cytotoxic agent.

In various embodiments, an SDC-TRAP can be further characterized in that the binding moiety (e.g., targeting moiety) and effector moiety are different, such that the pharmaceutical conjugate may be viewed as a heterodimeric compound produced by the joining of two different moieties. In terms of function, SDC-TRAP molecules have a targeting functionality and effector functionality (e.g., therapeutic, imaging, diagnostic). These functions are provided by corresponding chemical moieties that can be different (or, in some cases, the same). SDC-TRAPs can include any one or more binding moieties conjugated to any one or more effector moieties. In some embodiments, a composition or method can include a combination of two or more binding moeities and/or two or more effector moieties (e.g., a combination therapy and/or multi target therapy) embodied in one or more different types of SDC-TRAPs.

In various embodiments, an SDC-TRAP is further characterized by its ability to passively diffuse and/or be actively transported into a target cell of interest. The diffusion and/or transport properties of the SDC-TRAP can be derived, at least in part, from ionic, polar, and/or hydrophobic properties of the SDC-TRAP. In preferred embodiments, the SDC-TRAP enter cells primarily by passive diffusion. The diffusion and/or transport properties of the SDC-TRAP can be derived, at least in part, from the molecular weight of the SDC-TRAP, the binding moiety, the effector moiety, and/or the similarity in weight between the binding moiety and the effector moiety. SDC-TRAPs are desirably small, such as in comparison to antibody-drug conjugates ("ADCs"). For example, the molecular weight of an SDC-TRAP can be less than about 1600, 1500, 1400, 1300, 1200, 1100, 1000, 900, 800, 700, 600, 500, or 400 Daltons. A binding moiety and an effector moiety can each be less than about 1000, 900, 800, 700, 600, 500, 400, 300, or 200 Daltons. A binding moiety and an effector moiety can be approximately equal in size (e.g., differ in weight by less than 400, 350, 300, 250, 200, 150, 100, or 50 Daltons).

Delivery of an effector molecule by an SDC-TRAP can result in greater potency compared to administering an untargeted drug comprising the same effector moiety, for example, because the SDC-TRAP can be localized at a desired target for an extended period of time through the association of a binding moiety and its target. Such localization can cause an effector moiety to be active and/or released in a target cell and/or tissue over an extended period of time. This resonance time can be selected through deliberate design of a linker moiety. In contrast, administration of the drug by itself in vivo can be more apt to have a shorter resonance time in a given target cell and/or tissue—if it traverses into the cell at all—due to the lack of an "anchor" within the cell.

SDC-TRAPs, in part because they comprise a targeting moiety and are relatively small in size, can be efficiently taken up or internalized by a target cell. Conversely, uptake or internalization is relatively inefficient for ADCs, which must deal with limited antigen expression and relatively inefficient internalization mechanisms for the antibody portion of the molecule. Hsp90 provides a good illustrative example of a difference between SDC-TRAPs and conventional ADCs. By way of comparison, the localization rate of radiolabeled monoclonal antibodies at a tumor in patients is low, on the order of 0.003-0.08% of the injected dose/g tumor. In contrast, a much higher accumulation rate (15-20% injected dose/g tumor) has been measured for SDC-TRAPs in mouse tumor xenografts.

SDC-TRAP pharmaceutical conjugates in accordance with the present invention can represent a significant advance over the state of the art in targeted drugs. SDC-TRAPs have broad application in many therapeutic, imaging, and diagnostic application. As discussed above, SDC-TRAPs are advantageously small in comparison to ADCs, enabling better penetration of solid tumors and more rapid clearance from normal tissues (e.g., reduced toxicity). The design of SDC-TRAPs (e.g., a structure-property relationship) can be established using methods and rationales within the grasp of those of ordinary skill in the art, and companion imaging diagnostics for targeted therapies may also easily be provided, in view of the simpler chemistry involved.

SDC-TRAPs of the invention are characterized by selective targeting of SDC-TRAPs to target cells in which a target protein is overexpressed. This leads to high intracellular concentrations of SDC-TRAP molecules in target cells as compared to non-targeted cells. Likewise, SDC-TRAPs of the invention are characterized by low concentrations of SDC-TRAP in non-targeted cells.

One illustrative embodiment involves a conjugate of an Hsp90 binding moiety linked to a chelator (i.e., the effector moiety, for metals such as In or Gd, which conjugate may function as an imaging agent for the cells/tissues targeted by the conjugate). Another, illustrative embodiment involves a conjugate of an Hsp90 binding moiety linked to a chemotherapeutic (i.e., the effector moiety, for example, SN-38). Alternatively, an illustrative SDC-TRAP is contemplated wherein an Hsp90 targeting moiety bearing radiolabeled halogen (e.g., such as an iodine isotope) can serve to image the cells/tissues targeted by the conjugate, and the effector moiety can be drug to treat the targeted cells/tissues. The progression of treatment may therefore be determined by imaging the tissues being treated and reviewing the images for the presence or absence of the labeled conjugate. Such embodiments are readily adaptable to essentially any cancer, or other chemotherapeutic target. Molecular targets (e.g., interacting with a binding moiety) used to target a particular cell or tissue can be selected based upon their presence in the target cell or tissue and/or their relative abundance in the target cell or tissue (e.g., disease-related versus normal cells).

SDC-TRAP molecules of the present invention represent a new class of drugs. One particular advantage of SDC-TRAPs is that they can be designed to selectively deliver an effector moiety (e.g., a chemotherapeutic drug) into a targeted cell because of the relative overexpression or presence of a binding moiety's molecular target in the cell. After the binding moiety binds the molecular target, the effector moiety is thereafter available (e.g., through cleavage of a linker moiety joining the binding moiety and the effector moiety) to act upon the cell. Accordingly, SDC-TRAPs employ a different mechanism from strategies currently used in the art, for example delivering an Hsp90 inhibitor to a cell using HPMA copolymer-Hsp90i conjugates, Hsp90i prodrugs, nanoparticle-Hsp90i conjugates, or micellar methodologies.

SDC-TRAPs can also described by the formula:

Binding moiety-$L$-$E$

Where "binding moiety" is a protein interacting binding moiety; L is a conjugation or linking moiety (e.g., a bond or a linking group); and E is an effector moiety. These elements are discussed in the context of additional illustrative examples below. However, while features of each element may be discussed separately, design and selection of an SDC-TRAP can involve the interplay and/or cumulative effect of features of each element (e.g., diffusion, binding, and effect).

Once SDC-TRAP molecules of the invention enter a target cell the effector molecule is released from the SDC-TRAP. In one embodiment, the effector molecule has no activity until it is released from the SDC-TRAP. Accordingly, once the SDC-TRAP molecules enter a target cell an equilibrium exists between free and bound SDC-TRAP molecules. In one embodiment, the effector moiety is only released from the SDC-TRAP when the SDC-TRAP is not associated with the target protein. For example, when an SDC-TRAP molecule is not bound intracellular enzymes can access the linker region thereby freeing the effector moiety. Alternatively, when free SDC-TRAP molecules may be able to release effector molecules through, for example, hydrolysis of the bond or linker that connects the binding moiety and effector moiety.

Accordingly, the rate of effector molecule release and the amount of effector molecule released can be controlled by using binding moieties that bind to the target protein with different affinities. For example, binding moieties that bind to the target protein with lower affinity will be free, resulting in higher concentrations of unbound intracellular SDC-TRAP, and thereby resulting in higher concentrations of free effector molecule. Therefore, in at least one embodiment, irreversibly-binding binding moieties are incompatible with certain aspects of the invention, e.g., those embodiments where effector molecule release is based on free intracellular SDC-TRAP molecules.

In one embodiment, SDC-TRAPs have favorable safety profiles, for example, when compared to, for example, the binding moiety or effector molecule alone. One reason for the increased safety profile is the rapid clearance of SDC-TRAP molecules that do not enter into a target cell.

A number of exemplary SDC-TRAP molecules are set forth in the examples. Specifically a number of Hsp90-specific SDC-TRAP molecules are described and used to demonstrate the efficacy of SDC-TRAP molecules.

Binding Moieties

A primary role of a binding moiety is to ensure that the SDC-TRAP delivers its payload—the effector moiety—to its target by binding to a molecular target in or on a target cell or tissue. In this respect, it is not necessary that the binding moiety also have an effect on the target (e.g., in the case of an Hsp90-targeting moiety, to inhibit Hsp90 in the manner that Hsp90 is are known to do, that is, exhibit pharmacological activity or interfere with its function), but in some embodiments, the binding moiety does have an effect on the target. Accordingly, in various embodiments, an activity of the SDC-TRAP is due solely to the effector moiety exerting a pharmacological effect on the target cell(s), which has been better facilitated by the pharmaceutical conjugate targeting the target cell(s). In other embodiments, an activity of the SDC-TRAP is due in part to the binding moiety—that is, the binding moiety can have an effect beyond targeting.

The molecular target of a binding moiety may or may not be part of a complex or structure of a plurality of biological molecules, e.g., lipids, where the complexes or structures may include lipoproteins, lipid bilayers, and the like. However, in many embodiments, the molecular target to which the binding moiety binds will be free (e.g., cytoplasmic globular protein and/or not be part of a macromolecular assembly or aggregation). The present invention can exploit the selectively high presence of a molecular target in locations of high physiological activity (e.g., Hsp90 in oncological processes). For example, where a drug target is an intracellular drug target, a corresponding molecular target (e.g., Hsp90) can be present in the cell. Likewise, where a drug target is an extracellular drug target, a corresponding molecular target (e.g., Hsp90) can be extracellular, proximal, or associated with the extracellular cell membrane of the target cell or tissue.

In various embodiments, a binding moiety can effect a target cell or tissue (e.g., in the case of an Hsp90-targeting moiety that in fact inhibits Hsp90, for example, Hsp90i). In such embodiments, a pharmacological activity of the binding moiety contributes to, complements, or augments, the pharmacological activity of the effector moiety. Such embodiments go beyond the advantages combination therapies (e.g., a cancer combination therapy of Hsp90i and a second drug such as ganetespib or crizotinib) by providing a therapy that can be carried out by administration of a single SDC-TRAP that realizes both the benefits of the combination therapy and targeting. Other examples of such SDC-TRAPs include conjugates of an Hsp90i (such as ganetespib) and a second cancer drug such as bortezomib, ixazomib, or delanzomib.

A range of pharmaceutical activities can be achieved by judicious selection of a binding moiety and an effector moiety. For example, for treating solid tumors, e.g., colon cancer, high continuous doses of antimetabolites such as capecitabine or gemcitabine tend to be required in combination with other drugs. A conjugate having an Hsp90-targeting moiety with lower binding affinity or inhibitory activity to Hsp90, e.g., as determined by a HER2 degradation assay, can be designed to meet this need. Such a conjugate can comprise an effector moiety that is a strong, potent antimetabolite such as 5-FU, to afford a high dose of the conjugate that may be dosed relatively frequently. Such an approach not only achieves the aim of providing a high dose of an antimetabolite fragment at the tumor, but also lowers the toxicity of administering the drug on its own, owing to the plasma stability of SDC-TRAPs of the invention, and the ability of the Hsp90-targeting moiety to deliver the antimetabolite to the desired cells or tissues.

In embodiments where solid tumors such as SCLC or colorectal cancer are to be treated with drugs such as topotecan or irinotecan, only low doses of the drug may be dosed. Due to the very high intrinsic activity of these drugs, an SDC-TRAP should be designed to provide a low dose of such drugs at the target tissue. In this scenario, for example, an Hsp90-targeting moiety having a higher binding affinity or inhibitory activity to Hsp90 (e.g., as determined by a HER2 degradation assay) can sufficiently maintain the presence of the drug in the tissue at a very high level, to ensure that enough of the drug reaches and is retained by the desired target tissue due to the low dosing.

In various illustrative embodiments where a molecular target of a binding moiety is Hsp90, the binding moiety can be an Hsp90-targeting moiety, for example a triazole/resorcinol-based compound that binds Hsp90, or a resorcinol amide-based compound that binds Hsp90, e.g., ganetespib, AUY-922 or AT-13387. In another embodiment, the binding moiety may advantageously be an Hsp90-binding compound of formula (I):

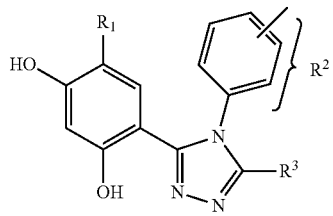

wherein $R^1$ may be alkyl, aryl, halide, carboxamide or sulfonamide; $R^2$ may be alkyl, cycloalkyl, aryl or heteroaryl, wherein when $R^2$ is a 6 membered aryl or heteroaryl, $R^2$ is substituted at the 3- and 4-positions relative to the connection point on the triazole ring, through which a linker L is attached; and $R^3$ may be SH, OH, —CONHR$^4$, aryl or heteroaryl, wherein when $R^3$ is a 6 membered aryl or heteroaryl, $R^3$ is substituted at the 3 or 4 position.

In another embodiment, the binding moiety may advantageously be an Hsp90-binding compound of formula (II):

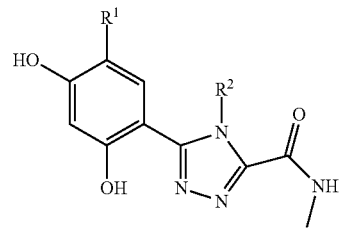

wherein $R^1$ may be alkyl, aryl, halo, carboxamido, sulfonamido; and $R^2$ may be optionally substituted alkyl, cycloalkyl, aryl or heteroaryl. Examples of such compounds include 5-(2,4-dihydroxy-5-isopropylphenyl)-N-(2-morpholinoethyl)-4-(4-(morpholinomethyl)phenyl)-4H-1,2,4-triazole-3-carboxamide and 5-(2,4-dihydroxy-5-isopropylphenyl)-4-(4-(4-methylpiperazin-1-yl)phenyl)-N-(2,2,2-trifluoroethyl)-4H-1,2,4-triazole-3-carboxamide.

In another embodiment, the binding moiety may advantageously be an Hsp90-binding compound of formula (III):

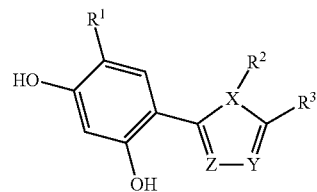

wherein

X, Y, and Z may independently be CH, N, O or S (with appropriate substitutions and satisfying the valency of the corresponding atoms and aromaticity of the ring); $R^1$ may be alkyl, aryl, halide, carboxamido or sulfonamido; $R^2$ may be substituted alkyl, cycloalkyl, aryl or heteroaryl, where a linker L is connected directly or to the extended substitutions on these rings; $R^3$ may be SH, OH, NR$^4$R$^5$ AND —CONHR$^6$, to which an effector moiety may be connected; $R^4$ and $R^5$ may independently be H, alkyl, aryl, or heteroaryl; and $R^6$ may be alkyl, aryl, or heteroaryl, having a minimum of one functional group to which an effector moiety may be connected. Examples of such compounds include AUY-922:

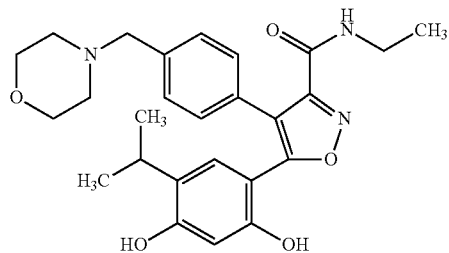 [SMILES: CCNC(=O)c1noc(-c2cc(C(C)C)c(O)cc2O)c1-c1ccc(CN2CCOCC2)cc1]

In another embodiment, the binding moiety may advantageously be an Hsp90-binding compound of formula (IV):

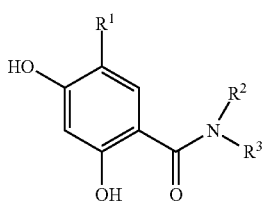

wherein

R[1] may be alkyl, aryl, halo, carboxamido or sulfonamido; R[2] and R[3] are independently $C_1$-$C_5$ hydrocarbyl groups optionally substituted with one or more of hydroxy, halogen, $C_1$-$C_2$ alkoxy, amino, mono- and di-$C_1$-$C_2$ alkylamino; 5- to 11-membered aryl or heteroaryl groups; or, R[2] and R[3], taken together with the nitrogen atom to which they are attached, form a 4- to 8-membered monocyclic heterocyclic group, of which up to 5 ring members are selected from O, N and S. Examples of such compounds include AT-13387:

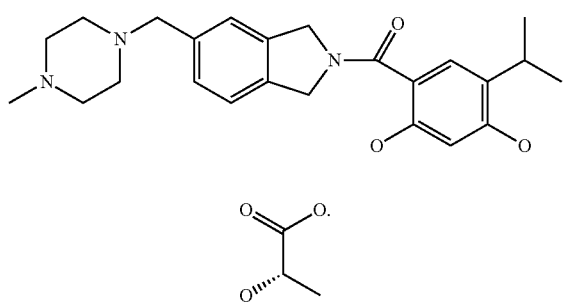

In certain embodiments, to enhance the bioavailability or delivery of the pharmaceutical conjugate, the binding moiety may be a prodrug of the Hsp90-binding compound. FIG. 1 shows how the illustrated Hsp90-targeting moiety may be suitably modified at one or more positions to enhance the physical, pharmacokinetic or pharmacodynamic properties of the conjugate.

Specific examples of suitable Hsp90-targeting moieties include geldanamycins, e.g.,

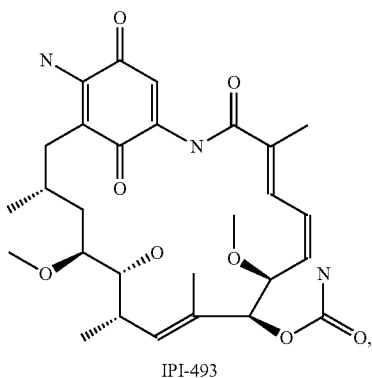

IPI-493

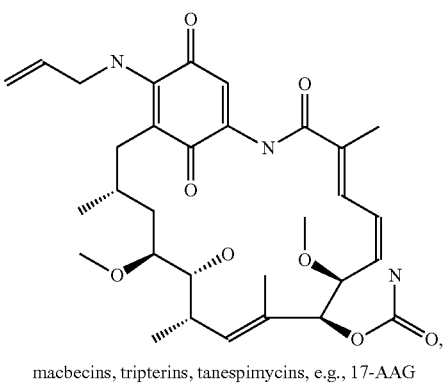

macbecins, tripterins, tanespimycins, e.g., 17-AAG

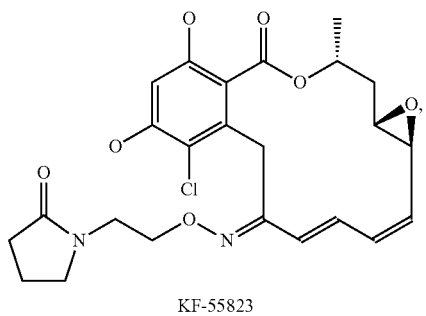

KF-55823

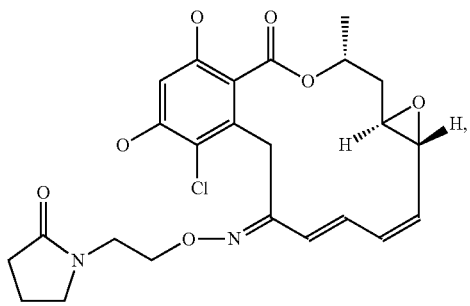

radicicols, KF-58333

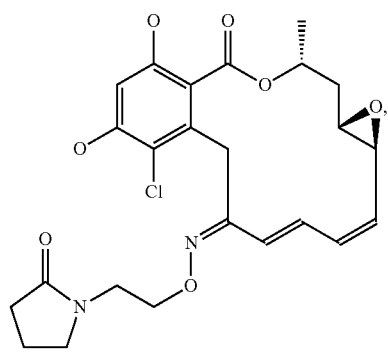

KF-58332

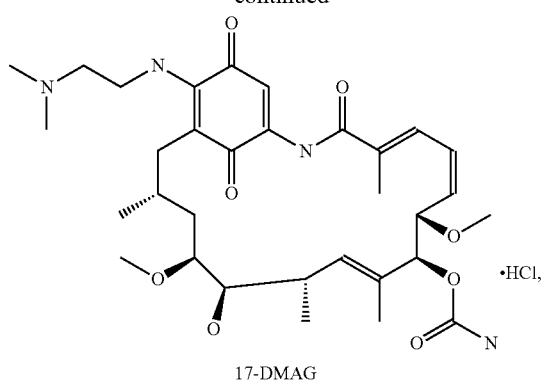
17-DMAG
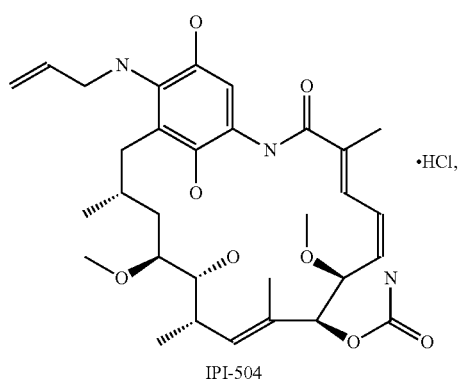
IPI-504
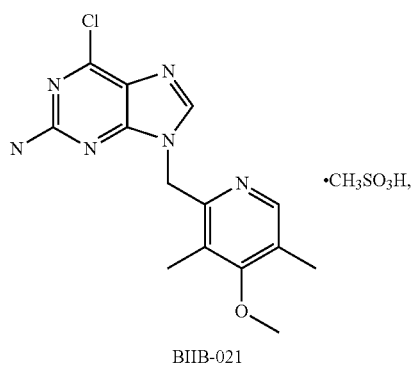
BIIB-021
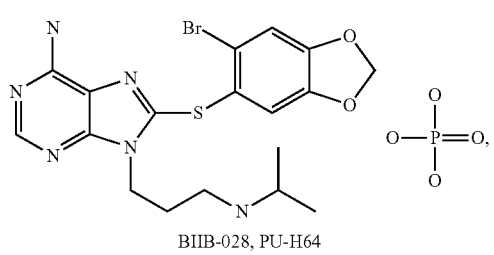
BIIB-028, PU-H64
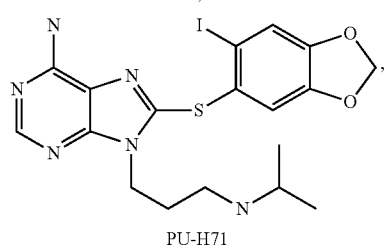
PU-H71
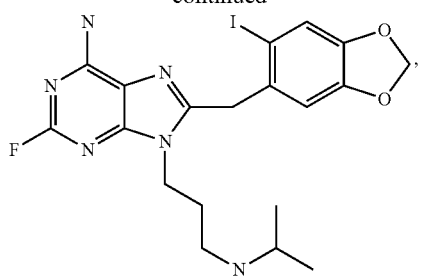
PU-DZ8
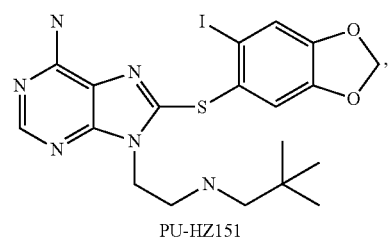
PU-HZ151
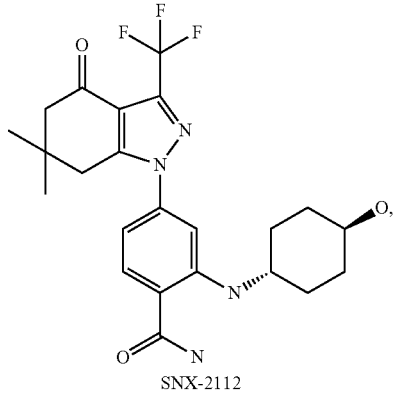
SNX-2112
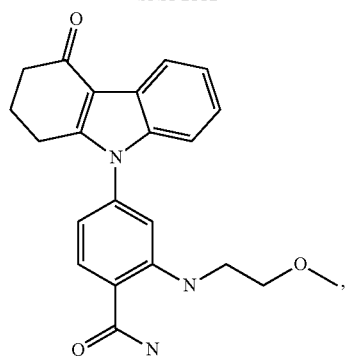
SNX-2321
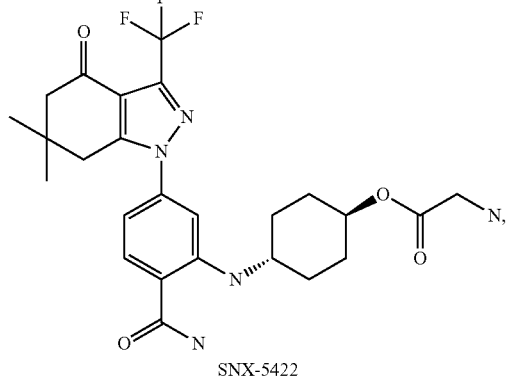
SNX-5422

-continued
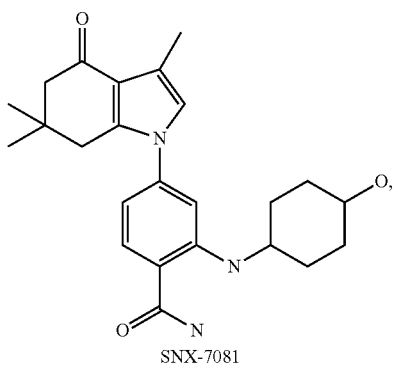
SNX-7081
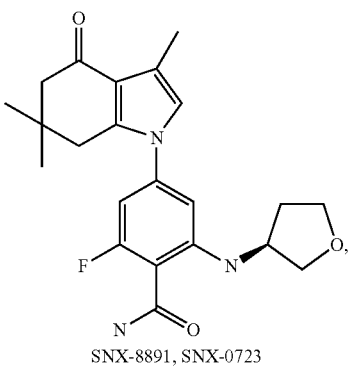
SNX-8891, SNX-0723
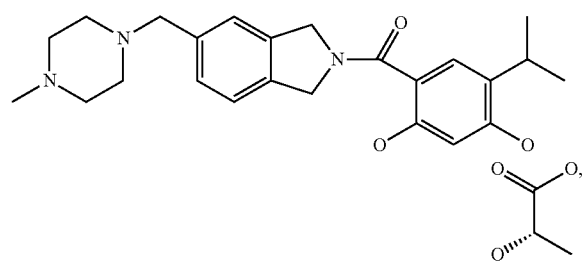
SAR-567530, ABI-287, ABI-328, AT-13387
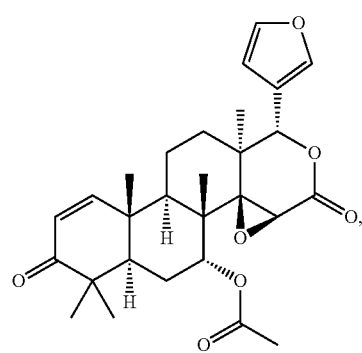
NSC-113497
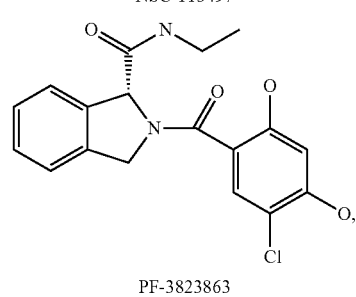
PF-3823863
-continued
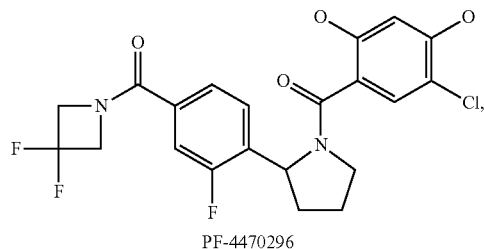
PF-4470296
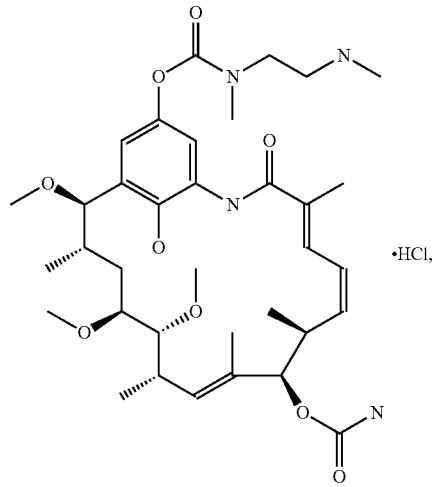
EC-102, EC-154, ARQ-250-RP, BC-274
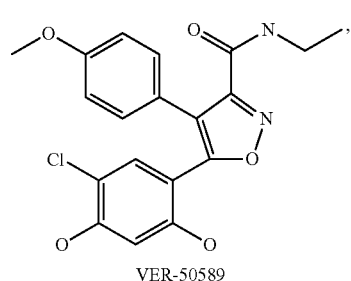
VER-50589
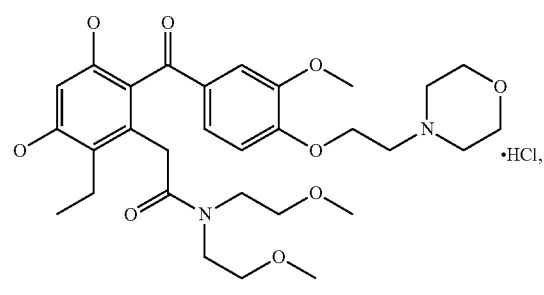
KW-2478
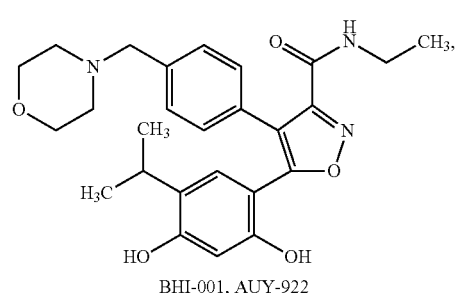
BHI-001, AUY-922

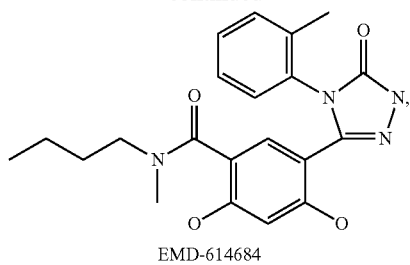
EMD-614684
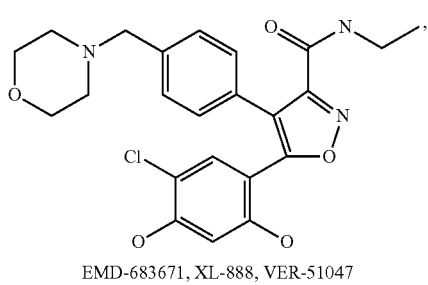
EMD-683671, XL-888, VER-51047
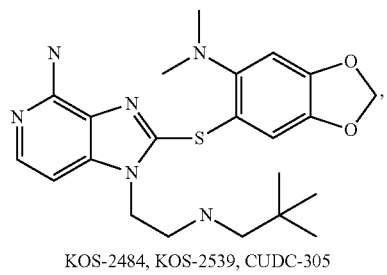
KOS-2484, KOS-2539, CUDC-305
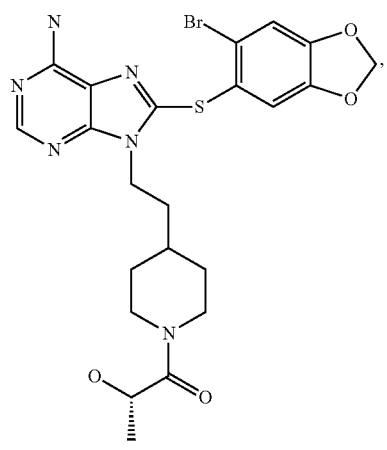
MPC-3100
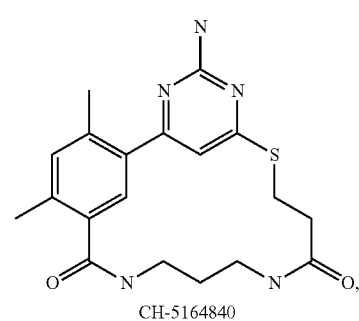
CH-5164840
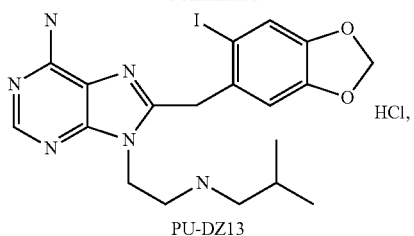
PU-DZ13
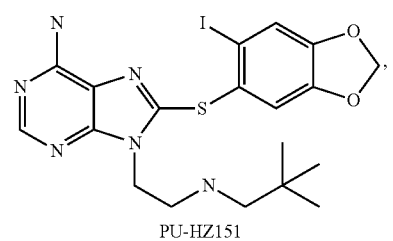
PU-HZ151
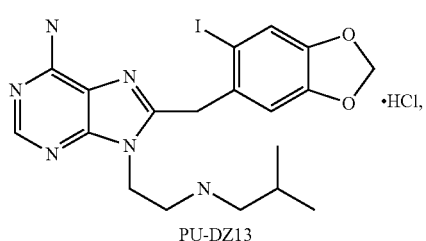
PU-DZ13
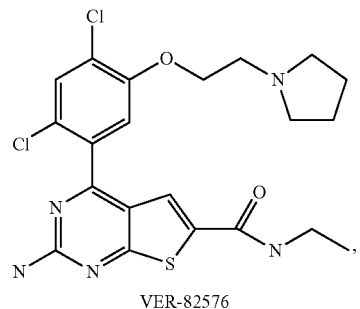
VER-82576
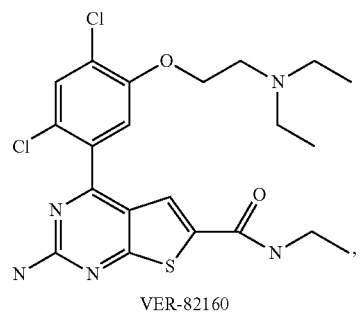
VER-82160
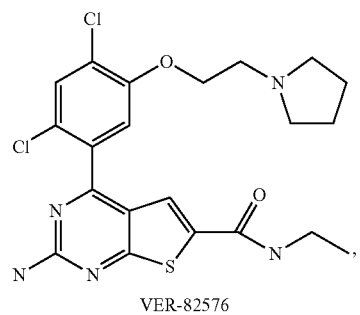
VER-82576

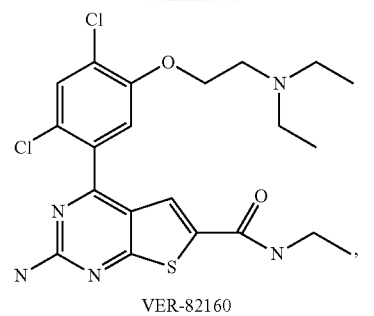

VER-82160

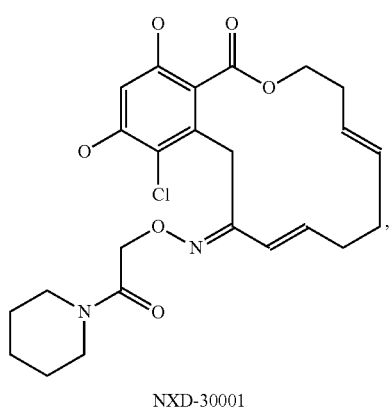

NXD-30001

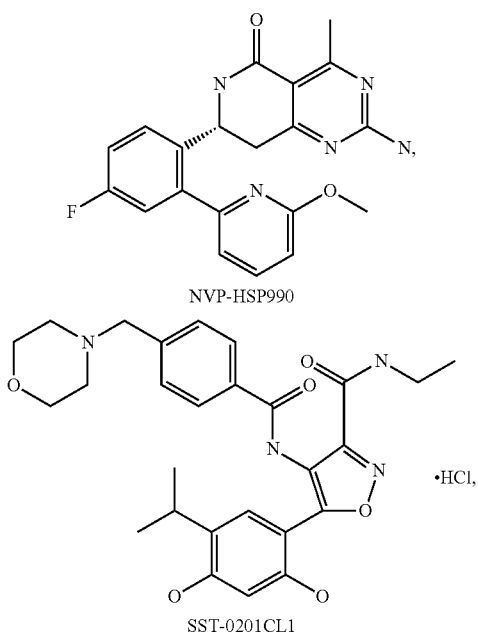

NVP-HSP990

SST-0201CL1 ·HCl,

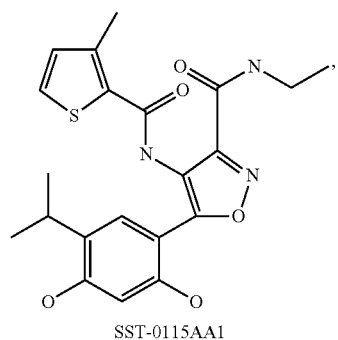

SST-0115AA1

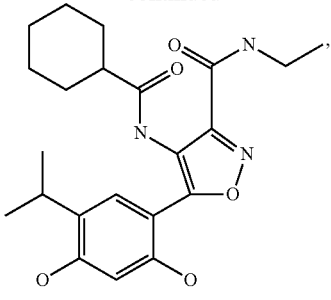

SST-0221AA1

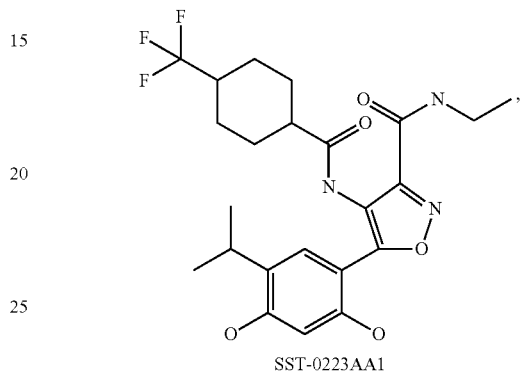

SST-0223AA1 novobiocin (a C-terminal Hsp90i.) The selection of other Hsp90-targeting moieties will be within the grasp of one of ordinary skill in the art. Likewise, the selection of binding moieties suitable for other molecular targets and/or other applications will be within the ability of one of ordinary skill in the art.

Additionally Hsp90 targeting moieties can be used to construct SDC-TRAP molecules for the treatment of inflammation. For example, binding moieties comprising the compounds shown in Tables 5, 6, and 7 of U.S. Patent Publication 2010/0280032, which is incorporated herein by reference in its entirety, or compounds of any formula therein, or tautomers, pharmaceutically acceptable salts, solvates, clathrates, hydrates, polymorphs or prodrugs thereof, inhibit the activity of Hsp90 and, thereby cause the degradation of Hsp90 client proteins. Any of these compounds may be coupled to an effector molecule to form an SDC-TRAP. The glucocorticoid receptor is a client protein of Hsp90 and binds to Hsp90 when it is in the conformation that is able to bind glucocorticoid ligands such as cortisol. Once a glucocorticoid binds to GR, the receptor disassociates with Hsp90 and translocates to the nucleus where it modulates gene expression to reduce inflammatory responses such as proinflammatory cytokine production. Thus, glucocorticoids may be given to patients in need of immunosuppression and patients with inflammatory and autoimmune disorders. Unfortunately, although glucocorticoids are effective at relieving inflammation, they have a number of severe side effects including osteoporosis, muscle wasting, hypertension, insulin resistance, truncal obesity and fat redistribution, and inhibition of wound repair. Inhibition of Hsp90 causes changes in GR activity which results in reduction of inflammatory responses similar to those seen for glucocorticoids. However, since the mechanism for reducing inflammation is different than that of glucocorticoids, it is expected that some or all of the side effects of glucocorticoid treatment will be reduced or eliminated.

Effector Moieties

An effector moiety can be any therapeutic or imaging agent that can be conjugated to a binding moiety and, in a thus conjugated state, delivered to a molecular target of the binding moiety. An effector molecule can, in some cases, require a linking moiety for conjugation (e.g., cannot be directly conjugated to a binding moiety). Similarly, an effector molecule can, in some cases, impede or reduce the ability of the binding moiety and/or SDC-TRAP to reach a target as long as the SDC-TRAP can still effect the target. However, in preferred embodiments, an effector moiety is readily conjugatable and may benefits delivery to, and effecting, of the target.

As described in greater detail below, an effector moiety can comprise a region that can be modified and/or participate in covalent linkage to a binding moiety without substantially adversely affecting the binding moiety's ability to bind to its target. An effector moiety can be a pharmaceutical molecule or a derivative thereof, which essentially retains activity while conjugated to a binding moiety. It will be appreciated that drugs with otherwise good and desirable activity can prove challenging to administer conventionally (e.g., due to poor bioavailability or undesirable side-effects in vivo prior to reaching their target)—such drugs can be "reclaimed" for use as effector moieties in the SDC-TRAPs of the present invention. Examples of effector moieties include, for example, bortezomib, ixazomib, and delanzomib. Further details regarding these compounds and their activities are provided below.

Conjugation and Linking Moieties

Binding moieties and effector moieties of the present invention can be conjugated, for example, through a linker or linking moiety L, where L may be either a bond or a linking group. For example, in various embodiments, a binding moiety and an effector moiety are bound directly or are parts of a single molecule. Alternatively, a linking moiety can provide a covalent attachment between a binding moiety and effector moiety. A linking moiety, as with a direct bond, can achieve a desired structural relationship between a binding moiety and effector moiety and or an SDC-TRAP and its molecular target. A linking moiety can be inert, for example, with respect to the targeting of a binding moiety and biological activity of an effector moiety.

Appropriate linking moieties can be identified using the affinity, specificity, and/or selectivity assays described herein. Linking moieties can be selected based on size, for example, to provide an SDC-TRAP with size characteristics as described above. In various embodiments, a linking moiety can be selected, or derived from, known chemical linkers. Linking moieties can comprise a spacer group terminated at either end with a reactive functionality capable of covalently bonding to the drug or ligand moieties. Spacer groups of interest include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine. Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. Specific linking moieties that may find use in the SDC-TRAPs include disulfides and stable thioether moieties.

In some embodiments, the linker or linking moiety of an SDC-TRAP can be advantageous when compared to the limited linking chemistry of antibody-drug conjugates (ADC). For example, unlike ADCs that are limited by the need to maintain the structure and/or stability of an antibody, SDC-TRAPs can use a wider range of linking chemistries and/or solvents (e.g., that can alter, distort, or denature an antibody).

In various embodiments, a linking moiety is cleavable, for example enzymatically cleavable. A cleavable linker can be used to release an effector moiety inside a target cell after the SDC-TRAP is internalized. The susceptibility of a linking moiety to cleavage can be used to control delivery of an effector molecule. For example, a linking moiety can be selected to provide extended or prolonged release of an effector moiety in a target cell over time (e.g., a carbamate linking moiety may be subject to enzymatic cleavage by a carboxylesterase via the same cellular process used to cleave other carbamate prodrugs like capecitabine or irinotecan). In these, and various other embodiments, a linking moiety can exhibit sufficient stability to ensure good target specificity and low systemic toxicity, but not so much stability that it results in lowering the potency and efficacy of the SDC-TRAP.

Exemplary linkers are described in U.S. Pat. No. 6,214,345 (Bristol-Myers Squibb), U.S. Pat. Appl. 2003/0096743 and U.S. Pat. Appl. 2003/0130189 (both to Seattle Genetics), de Groot et al., J. Med. Chem. 42, 5277 (1999); de Groot et al. J. Org. Chem. 43, 3093 (2000); de Groot et al., J. Med. Chem. 66, 8815, (2001); WO 02/083180 (Syntarga); Carl et al., J. Med. Chem. Lett. 24, 479, (1981); Dubowchik et al., Bioorg & Med. Chem. Lett. 8, 3347 (1998) and Doronina et al. BioConjug Chem. 2006; Doronina et al. Nat Biotech 2003.

Identification and Selection of Targets and Corresponding SDC-TRAPs

The present invention provides for a broad class of pharmacological compounds including an effector moiety conjugated to an binding moiety directing the effector moiety to a biological target of interest. While treating cancer using an Hsp90 inhibitor binding moiety conjugated to a cytotoxic agent effector moiety is one illustrative example of the present invention, SDC-TRAPs are fundamentally broader in terms of their compositions and uses.

In various embodiments, the broad class of SDC-TRAP pharmacological compounds that are directed to biological targets have the following properties:

the biological target (a cell and/or tissue target of interest, e.g., a tumor) should be effectible by an effector moiety, and the effector moiety should be known or developed for the biological target (e.g., chemotherapeutic agent for the tumor); the biological target should be associated with a molecular target (e.g., biomolecule, capable of being specifically bound, that is uniquely represented in the biological target) that specifically interacts with a binding moiety, and the binding moiety should be known or developed for the molecular target (e.g., ligand for the biomolecule); and the effector moiety and binding moiety should be amenable to coupling and should essentially retain their respective activity after coupling. Furthermore, the conjugate should be capable of reaching and interacting with the molecular target, and in clinical applications should be suitable for administration to a subject (e.g., a subject can tolerate a therapeutically effective dose). Examples of therapeutic molecular targets (i.e., binding moiety binding partners) for various conditions/disease states include, for example, bortezomib, ixazomib, and delanzomib.

Imaging Moieties, and Diagnostic and Research Applications

In various embodiments, the effector moiety is an imaging moiety—that is, a molecule, compound, or fragment thereof that facilitates a technique and/or process used to create images or take measurements of a cell, tissue, and/or organism (or parts or functions thereof) for clinical and/or research purposes. An imaging moiety can produce, for example, a signal through emission and/or interaction with electromagnetic, nuclear, and/or mechanical (e.g., acoustic as in ultrasound) energy. An imaging moiety can be used, for example, in various radiology, nuclear medicine, endoscopy, thermography, photography, spectroscopy, and microscopy methods.

Imaging studies can be used, for example, in a clinical or research setting to diagnose a subject, select a subject for therapy, select a subject for participation in a clinical trial, monitor the progression of a disease, monitor the effect of therapy, to determine if a subject should discontinue or continue therapy, to determine if a subject has reached a clinical end point, and to determine recurrence of a disease. Imaging studies can be used, for example, to conduct research to identify effective interacting moieties and/or effector moieties and/or combinations thereof, to identify effective dosing and dose scheduling, to identify effective routes of administration, and to identify suitable targets (e.g., diseases susceptible to particular treatment).

Methods of Making Pharmaceutical Conjugates

The pharmaceutical conjugates, i.e., SDC-TRAPs, of the invention may be prepared using any convenient methodology. In a rational approach, the pharmaceutical conjugates are constructed from their individual components, binding moiety, in some cases a linker, and effector moiety. The components can be covalently bonded to one another through functional groups, as is known in the art, where such functional groups may be present on the components or introduced onto the components using one or more steps, e.g., oxidation reactions, reduction reactions, cleavage reactions and the like. Functional groups that may be used in covalently bonding the components together to produce the pharmaceutical conjugate include: hydroxy, sulfhydryl, amino, and the like. The particular portion of the different components that are modified to provide for covalent linkage will be chosen so as not to substantially adversely interfere with that components desired binding activity, e.g., for the effector moiety, a region that does not affect the target binding activity will be modified, such that a sufficient amount of the desired drug activity is preserved. Where necessary and/or desired, certain moieties on the components may be protected using blocking groups, as is known in the art, see, e.g., Green & Wuts, Protective Groups in Organic Synthesis (John Wiley & Sons) (1991).

Alternatively, the pharmaceutical conjugate can be produced using known combinatorial methods to produce large libraries of potential pharmaceutical conjugates which may then be screened for identification of a bifunctional, molecule with the pharmacokinetic profile. Alternatively, the pharmaceutical conjugate may be produced using medicinal chemistry and known structure-activity relationships for the targeting moiety and the drug. In particular, this approach will provide insight as to where to join the two moieties to the linker.

A number of exemplary methods for preparing SDC-TRAP molecules are set forth in the examples. As one of skill in the art will understand, the exemplary methods set forth in the examples can be modified to make other SDC-TRAP molecules. Additional exemplary methods for preparation and testing of SDC-TRAPs are provided in PCT Publication WO2013/158644 which is incorporated herein by reference in its entirety.

Methods of Use, Pharmaceutical Preparations, and Kits

The pharmaceutical conjugates find use in treatment of a host condition, e.g., a disease condition. In these methods, an effective amount of the pharmaceutical conjugate is administered to the host, where "effective amount" means a dosage sufficient to produce the desired result, e.g., an improvement in a disease condition or the symptoms associated therewith. In many embodiments, the amount of drug in the form of the pharmaceutical conjugate that need be administered to the host in order to be an effective amount will vary from that which must be administered in free drug form. The difference in amounts may vary, and in many embodiments may range from two-fold to ten-fold. In certain embodiments, e.g., where the resultant modulated pharmacokinetic property or properties result(s) in enhanced activity as compared to the free drug control, the amount of drug that is an effective amount is less than the amount of corresponding free drug that needs to be administered, where the amount may be two-fold, usually about four-fold and more usually about ten-fold less than the amount of free drug that is administered.

The pharmaceutical conjugate may be administered to the host using any convenient means capable of producing the desired result. Thus, the pharmaceutical conjugate can be incorporated into a variety of formulations for therapeutic administration. More particularly, the pharmaceutical conjugate of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the pharmaceutical conjugate can be achieved in various ways, including oral, buccal, rectal, parenteral, intraperitoneal, intradermal, transdermal, intracheal, etc., administration. In pharmaceutical dosage forms, the pharmaceutical conjugate may be administered alone or in combination with other pharmaceutically active compounds.

The subject methods find use in the treatment of a variety of different disease conditions. In certain embodiments, of particular interest is the use of the subject methods in disease conditions where an active agent or drug having desired activity has been previously identified, but which active agent or drug does not bind to its target with desired affinity and/or specificity. With such active agents or drugs, the subject methods can be used to enhance the binding affinity and/or specificity of the agent for its target.

The specific disease conditions treatable by with the subject bifunctional compounds are as varied as the types of drug moieties that can be present in the pharmaceutical conjugate. Thus, disease conditions include cellular proliferative diseases, such as neoplastic diseases, autoimmune diseases, central nervous system or neurodegenerative diseases, cardiovascular diseases, hormonal abnormality diseases, infectious diseases, and the like.

By treatment is meant at least an amelioration of the symptoms associated with the disease condition afflicting the host, where amelioration is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

Methods of use of the invention extend beyond strict treatment of a disease. For example, the invention includes uses in a clinical or research setting to diagnose a subject, select a subject for therapy, select a subject for participation in a clinical trial, monitor the progression of a disease, monitor the effect of therapy, to determine if a subject should discontinue or continue therapy, to determine if a subject has reached a clinical end point, and to determine recurrence of a disease. The invention also includes uses in conducting research to identify effective interacting moieties and/or effector moieties and/or combinations thereof, to identify effective dosing and dose scheduling, to identify effective routes of administration, and to identify suitable targets (e.g., diseases susceptible to particular treatment).

A variety of hosts are treatable according to the subject methods. Generally such hosts are "mammals" or "mammalian," where these terms are used broadly to describe organisms which are within the class Mammalia, including the orders carnivore (e.g., dogs and cats), rodentia (e.g., mice, guinea pigs, and rats), and primates (e.g., humans, chimpanzees, and monkeys). In many embodiments, the hosts will be humans.

The invention provides kits for treating a subject in need thereof comprising at least one SDC-TRAP and instruction for administering a therapeutically effective amount of the at least one SDC-TRAP to the subject, thereby treating the subject. The invention also provides kits for imaging, diagnosing, and/or selecting a subject comprising at least one SDC-TRAP and instruction for administering an effective amount of at least one SDC-TRAP to the subject, thereby imaging, diagnosing, and/or selecting the subject.

Kits with unit doses of the pharmaceutical conjugate, usually in oral or injectable doses and often in a storage stable formulation, are provided. In such kits, in addition to the containers containing the unit doses, an informational package insert describing the use and attendant benefits of the drugs in treating pathological condition of interest will be included. Preferred compounds and unit doses are those described herein above.

The invention also provides methods for treatment of a disease or disorder in which the subject to be treated is selected for treatment based on the presence of, or the overexpression of, a particular protein. For example, subjects may be selected for treatment of cancer based on the presence of greater the normal levels of Hsp90. In this case, subjects would be administered an SDC-TRAP that comprises a binding moiety that selectively binds to Hsp90.

The invention provides methods of treating or preventing an inflammatory disorder in a subject, comprising administering to the subject an effective amount of a compound represented by any one of formula (I) through (LXXII), or any embodiment thereof, or a compound shown in Table 5, 6, or 7 as disclosed in U.S. Patent Publication 2010/0280032. In one embodiment, the compound or binding moiety or SDC-TRAP may be administered to a human to treat or prevent an inflammatory disorder. In another embodiment, the inflammatory disorder is selected from the group consisting of transplant rejection, skin graft rejection, arthritis, rheumatoid arthritis, osteoarthritis and bone diseases associated with increased bone resorption; inflammatory bowel disease, ileitis, ulcerative colitis, Barrett's syndrome, Crohn's disease; asthma, adult respiratory distress syndrome, chronic obstructive airway disease; corneal dystrophy, trachoma, onchocerciasis, uveitis, sympathetic ophthalmitis, endophthalmitis; gingivitis, periodontitis; tuberculosis; leprosy; uremic complications, glomerulonephritis, nephrosis; sclerodermatitis, psoriasis, eczema; chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immune-complex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma. In another embodiment, an SDC-TRAP, or a compound shown in Table 5, 6, or 7 as disclosed in U.S. Patent Publication 2010/0280032, is administered with an additional therapeutic agent. In another embodiment, the additional therapeutic agent may an anti-inflammatory agent.

In one embodiment, an SDC-TRAP that is administered to a subject but does not enter a target cell is rapidly cleared from the body. In this embodiment, the SDC-TRAP that does not enter a target cell is rapidly cleared in order to reduce the toxicity due to the components of the SDC-TRAP, the degradation products of the SDC-TRAP or the SDC-TRAP molecule. Clearance rate can be determined by measuring the plasma concentration of the SDC-TRAP molecule as a function of time.

Likewise, SDC-TRAP molecules that enter non-targeted cells by passive diffusion rapidly exit the non-targeted cell or tissue and are either eliminated from the subject or proceed to enter and be retained a targeted cell or tissue. For example, an SDC-TRAP that is intended to treat tumor cells and is targeted to tumor cells that overexpress, for example, Hsp90 will accumulate selectively in tumor cells that overexpress Hsp90. Accordingly, very low levels of this exemplary SDC-TRAP will be present in non-tumor tissue such as normal lung tissue, heart, kidney, and the like. In one embodiment, the safety of the SDC-TRAP molecules of the invention can be determined by their lack of accumulation in non-targeted tissue. Conversely, the safety of the SDC-TRAP molecules of the invention can be determined by their selective accumulation in the targeted cells and/or tissue.

EXAMPLES

The following examples, which are briefly summarized and then discussed in turn below, are offered by way of illustration and not by way of limitation.

Example 1—The Design of the HSP90-Inhibitor Bortezomib Conjugates

One of the major challenges in cancer chemotherapy involves delivery of potent drugs selectively to the pathological cells without exposing the toxic effects of the drugs to the normal tissue. Bortezomib (Velcade®), the first proteasome inhibitor approved by the FDA in 2003, is a drug that suffers such selectivity. In 2003, bortezomib received fast-track approval for the treatment of refractory multiple myeloma (MM) based on the data presented from two independent phase II trials: the CREST trial (British Journal of Haematology, 2004, 127, 165-172; British Journal of Haematology, 2008, 143, 537-540) and the SUMMIT trial (The New England Journal of Medicine, 2003, 348, 2609-2617). The drug is a C-terminal boronic acid and it is the boron atom that is in fact essential for inhibiting proteasome activity because of its ability to specifically and tightly bind the 35 catalytic subunit. In 2008, bortezomib successfully became the front-line therapy for newly diagnosed MM patients based on the phase III VISTA trial (The New England Journal of Medicine, 2008, 359, 906-917; Journal of Clinical Oncology, 2010, 28, 2259-2266). There is great interest in expanding the use of bortezomib for the treatment of other cancers. With the good, however, comes some disadvantages and/or limitations of bortezomib that have been observed during its preclinical and clinical development.

First, in solid tumors, the efficacy of bortezomib has been disappointing. Its use has been extensively investigated in several solid tumor types, but its success has fallen short when compared to hematological malignancies. For example, in a study including patients with castration resistant metastatic prostate cancer neither bortezomib alone, nor combined with prednisone, exhibited significant antitumor effects (Journal of Urology, 2007, 178, 2378-2383). Similarly, a trial testing bortezomib monotherapy in chemotherapy-naïve patients with advanced stage non-small cell lung cancer was terminated in the first stage due to lack of response in patients (Lung Cancer, 2010, 68, 89-93). Bortezomib monotherapy was also inactive in patients with unresectable or metastatic gastric and gastroesophageal junction adenocarcinoma (Investigational New Drugs, 2011, 29, 1475-1481).

Second, although it is generally well-tolerated, bortezomib still generates some toxicity, and in some cases the regimen must be discontinued. The most frequent occurring side effects are nausea, diarrhea and fatigue. More serious adverse drug reactions include peripheral neuropathy, thrombocytopenia, neutropenia and lymphopenia. It is estimated that more than 40% of patients will present with peripheral neuropathy (Nature, 2011, 480, S40-S42).

Another shortcoming of bortezomib is its narrow therapeutic window. According to a phase I trial, the therapeutic dose of bortezomib is 1.3 mg/m2 and the dose-limiting toxic effects are observed with only a slightly higher dose of 1.5 mg/m$^2$.

Targeting of drugs to cancer cells can be improved by conjugation of anti-cancer drugs (e.g, bortezomib) to a targeting moiety, specifically an HSP-90 inhibitor to form an HSP-90 Inhibitor Drug Conjugate (SDC-TRAP). Small-molecule drug conjugates consisting of a drug (e.g., an anti-cancer drug, e.g., bortezomib) covalently attached to another molecule that possesses the requisite cancer cell recognition properties, in this case the HSP90 inhibitor can be prepared. The active HSP90 protein in tumors attracts the HSP90-inhibitor portion in the SDC-TRAPs, bringing the entire SDC-TRAP, in this case HSP90-inhibitor anti-cancer drug conjugate, preferentially to tumors. Upon entry of the conjugate into the cell through diffusion, the SDC-TRAP will bind the HSP90 protein, and slowly release the drug into the cell to allow it to perform its pharmacological activity, and eventually lead to efficacy. The ultimate effects are: (a) higher concentration and sustained exposure of the cancer cell to the drug occurs, compared to unconjugated drug, (b) reduced side effects, (c) reduced frequency of dosing, and (d) an overall improved therapeutic window of the drug.

Bortezomib contains an electrophilic warhead boron atom, which is essential for inhibiting the proteasome activity. X-ray diffraction studies have shown that the inhibitor's boron atom reacts covalently with the active site Thr1-Oγ to form a tetrahedral boronate adduct (Chemical Reviews, 2007, 107, 687-717). The design of the HSP90-inhibitor bortezomib conjugates is to make a sterically hindered boronate ester as the linking unit between bortezomib and the HSP90 inhibitor. That will occur through conjugating the corresponding sterically hindered diol, the HSP90 inhibitor, to bortezomib. The sterically hindered boronate ester serves two purposes. One, the sterics slows down the hydrolysis of the boronate ester ultimately releasing bortezomib (the payload) form the HSP90 inhibitor. Second, the sterics shields the electrophilic boron atom, hence inactivating the drug towards its pharmacological activity, i.e. proteasome inhibition, until it is released from the conjugate (the SDC-TRAP). In this case, the drug's activity is muted in the conjugate, until the drug is released. This design should ultimately solve many of the toxicity profile associated with bortezomib (as mentioned above). The sterically shielded boron atom in the HSP90-inhibitor bortezomib conjugates will also allow bortezomib to withstand the rapid metabolism in plasma. The following is an illustration of the design.

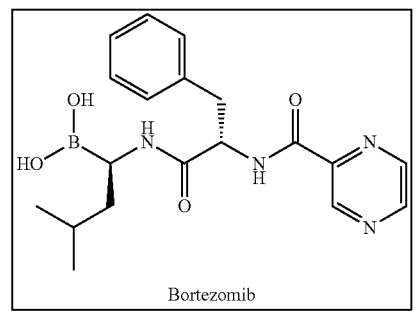

Bortezomib

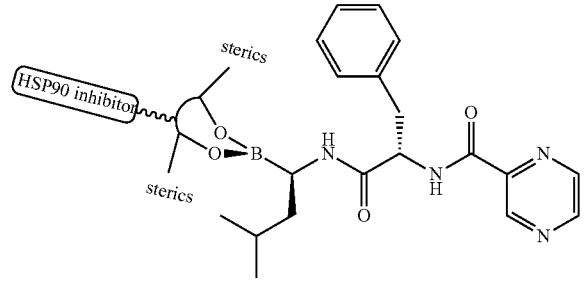

The necessary chemistry to prepare such conjugates is illustrated below using selected examples. A condensation reaction between bortezomib and the relevant sterically-hindered diol (HSP90-inhibitor moiety) takes place to yield the conjugate.

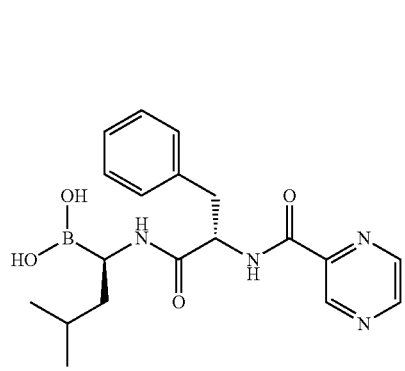
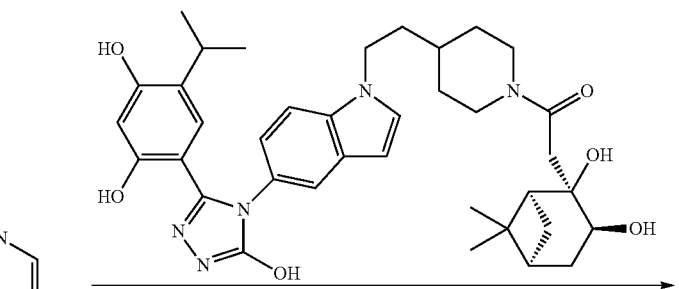
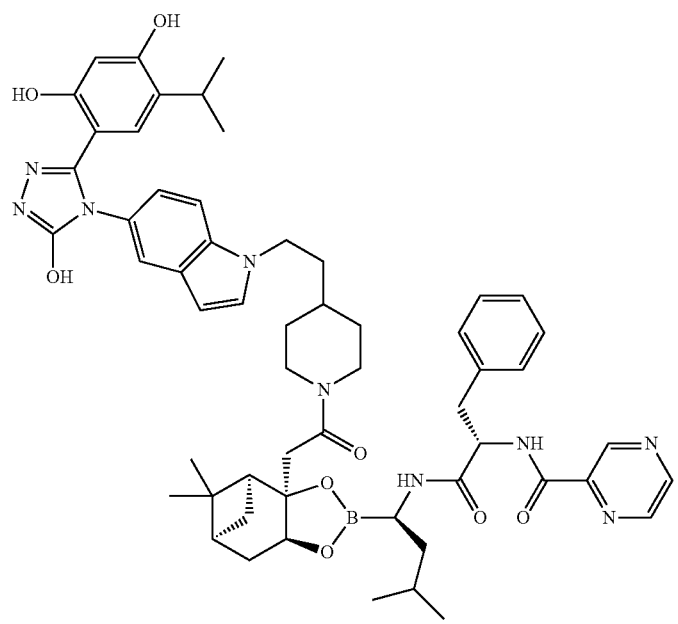
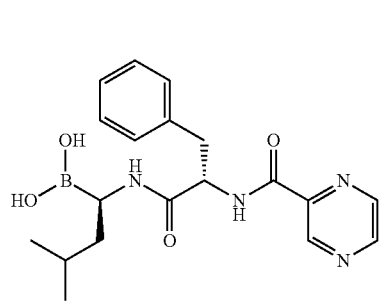
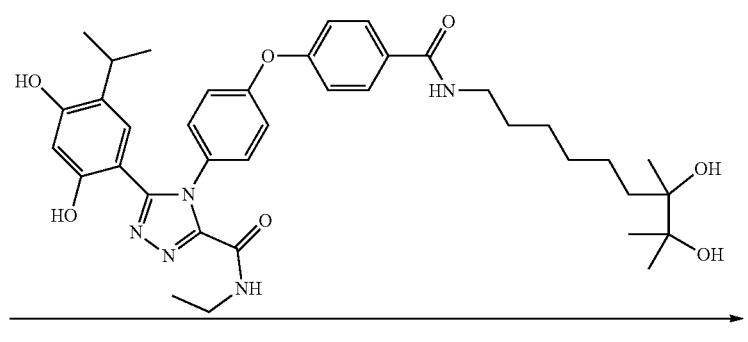

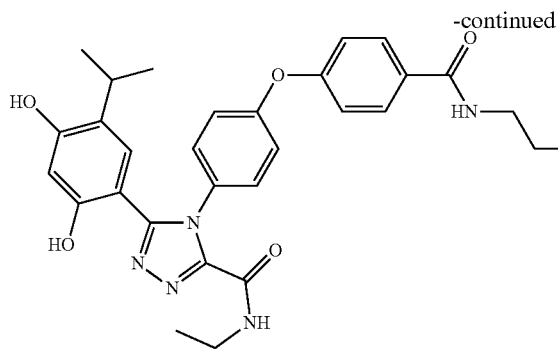
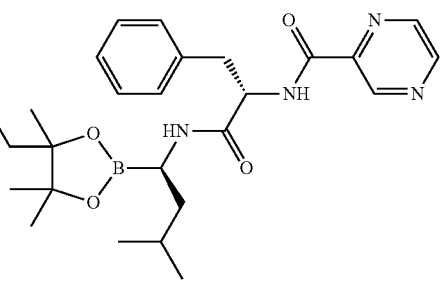

Example 2—Exemplary Bortezomib Conjugates

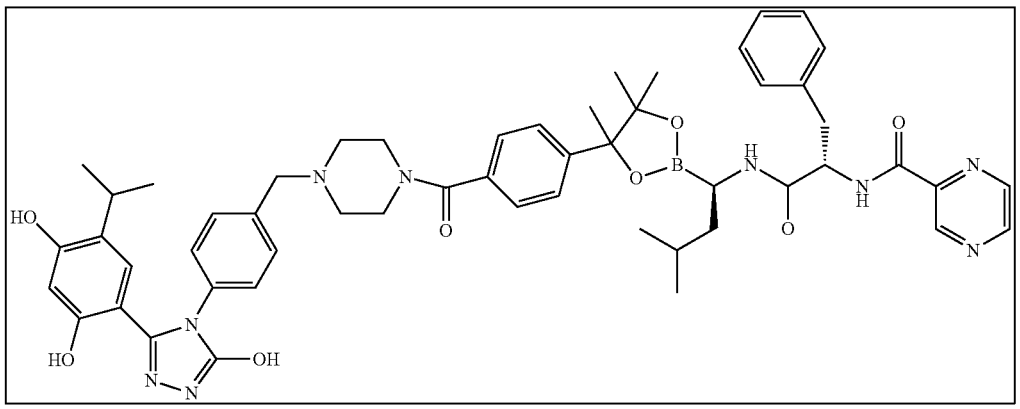

SDC-TRAP-0236

Other improvements to current design:

An alternative way to further improve the current design, to ultimately lead to more plasma-stable conjugates (to prevent or reduce pre-mature release of bortezomib) and further shield the warhead (boron atom), is to incorporate a nitrogen in the boronate unit, so as to form a dative bond with boron at the empty p orbital. This further interaction with boron should stabilize the boronate ester, and further shield the boron from any type of reactivity towards nucleophilic amino acids in vitro and in vivo.

rigid, stable
through dative
bond to boron
(shield boron atom)

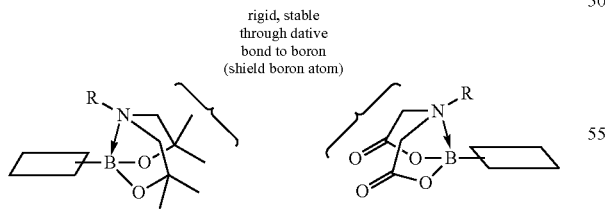

Alternative designs to the current one:

Other ways to prepare HSP90-inhibitor bortezomib conjugates is to functionalize one of the amides on bortezomib to the HSP90 inhibitor. The type of linkage will be a carbamate moiety. These types of linkages are inherently more stable than the boronate esters described above.

SDC-TRAPs of an Exemplary Embodiment May be Prepared in the Following Manner:

Synthetic protocol for 4-(2,3-dihydroxy-3-methylbutan-2-yl)benzoic acid.

The compound 4-(2,3-dihydroxy-3-methylbutan-2-yl)benzoic acid was prepared following the below scheme and references.

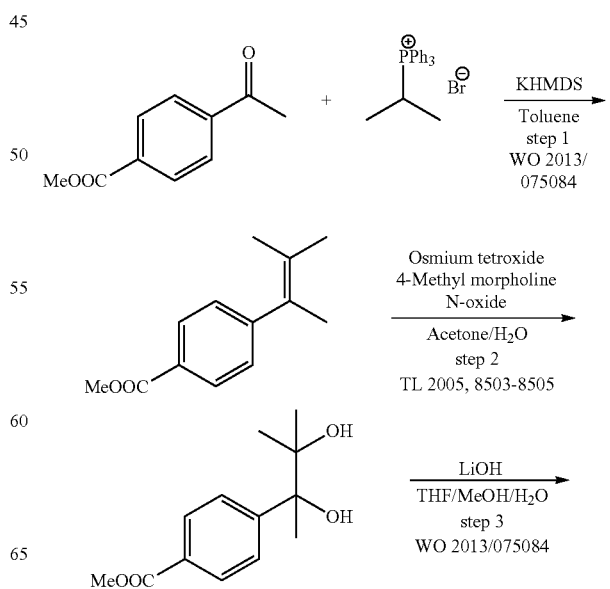

-continued

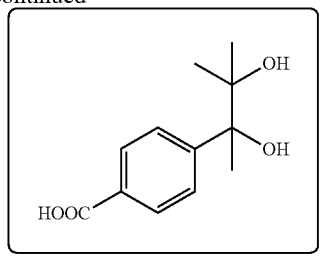

N-((2S)-1-(((1R)-1-(4-(4-(4-(4-(3-(2,4-dihydroxy-5-isopropylphenyl)-5-hydroxy-4H-1,2,4-triazol-4-yl)benzyl)piperazine-1-carbonyl)phenyl)-4,5,5-trimethyl-1,3,2-dioxaborolan-2-yl)-3-methylbutyl)amino)-1-oxo-3-phenylpropan-2-yl)pyrazine-2-carboxamide 1-ylmethyl)phenyl)-4H-1,2,4-triazol-3-yl)-6-isopropyl benzene-1,3-diol hydrochloride (0.3 mmol) in DMF (2 mL) was added HATU (0.36 mmol) followed by diisopropyl ethylamine (1.2 mmol). The reaction mixture was stirred at room temperature overnight then concentrated. The residue was partitioned between ethyl acetate and water. The organic phase was separated, washed with brine, dried ($Na_2SO_4$) and concentrated. The crude product was purified by ISCO using DCM/MeOH as eluent to afford (4-(2,3-dihydroxy-3-methylbutan-2-yl)phenyl)(4-(4-(3-(2,4-dihydroxy-5-isopropylphenyl)-5-hydroxy-4H-1,2,4-triazol-4-yl)benzyl)piperazin-1-yl)methanone as a white solid. ESMS calcd for $C_{34}H_{41}N_5O_6$: 615.31. found: 616.0 (M+H$^+$).

Step 2:

A round-bottomed flask was charged with (4-(2,3-dihydroxy-3-methylbutan-2-yl)phenyl)(4-(4-(3-(2,4-dihydroxy-5-isopropylphenyl)-5-hydroxy-4H-1,2,4-triazol-4-yl)benzyl)piperazin-1-yl)methanone (0.1 mmol), Bortezomib (0.1 mmol), DMF (1 mL) and 4 Å molecular sieves (100 mg). The mixture was stirred at 50° C. for 15 h then filtered. The filtrate was concentrated under reduced pressure and the

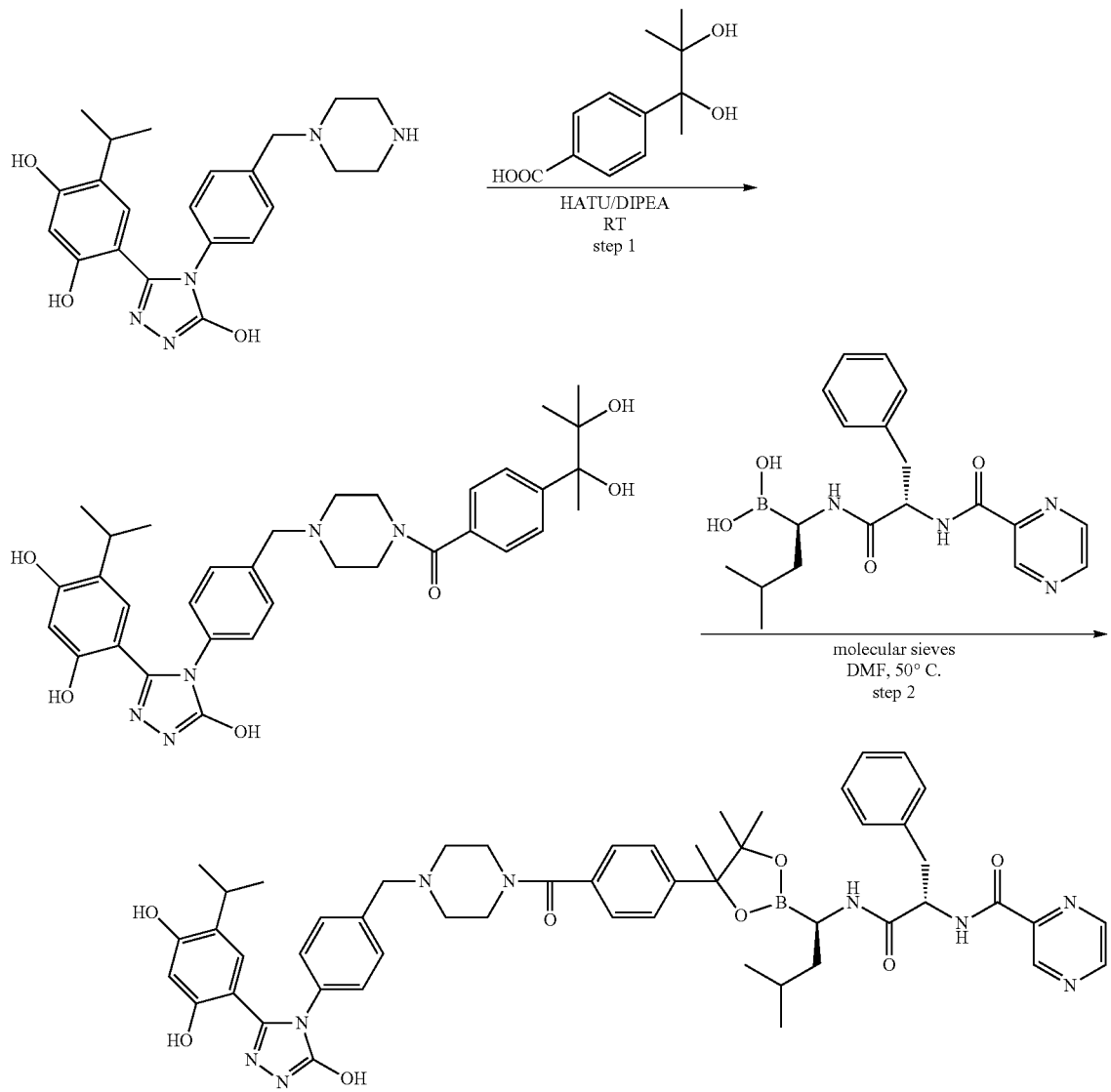

Step 1:
To a mixture of 4-(2,3-dihydroxy-3-methylbutan-2-yl)benzoic acid (0.3 mmol) and 4-(5-hydroxy-4-(4-(piperazinresulting residue was purified by silica gel chromatography (CH$_2$Cl$_2$/MeOH) then by reverse phase chromatography (ACN/H$_2$O with HCOOH) to afford the desired product as a white solid. ESMS calcd for C$_{53}$H$_{62}$BN$_9$O$_8$: 963.48. found: 964.1 (M+H$^+$).

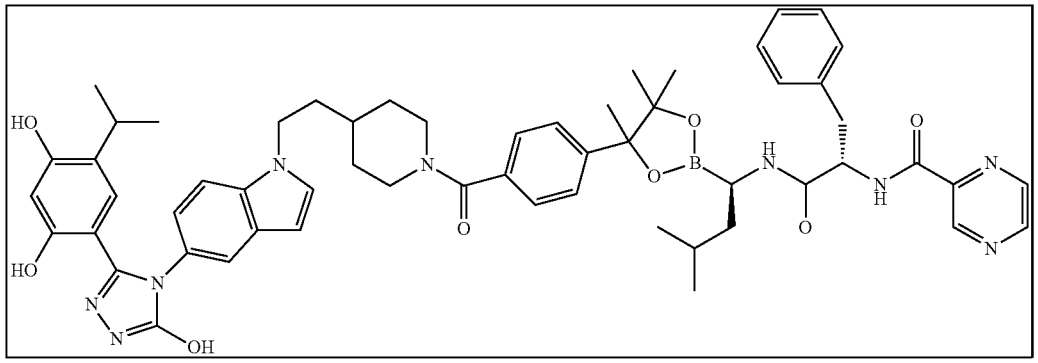

SDC-TRAP-0237

N-((2S)-1-(((1R)-1-(4-(4-(4-(2-(5-(3-(2,4-dihydroxy-5-isopropylphenyl)-5-hydroxy-4H-1,2,4-triazol-4-yl)-1H-indol-1-yl)ethyl)piperidine-1-carbonyl)phenyl)-4,5,5-trimethyl-1,3,2-dioxaborolan-2-yl)-3-methylbutyl)amino)-1-oxo-3-phenylpropan-2-yl) pyrazine-2-carboxamide

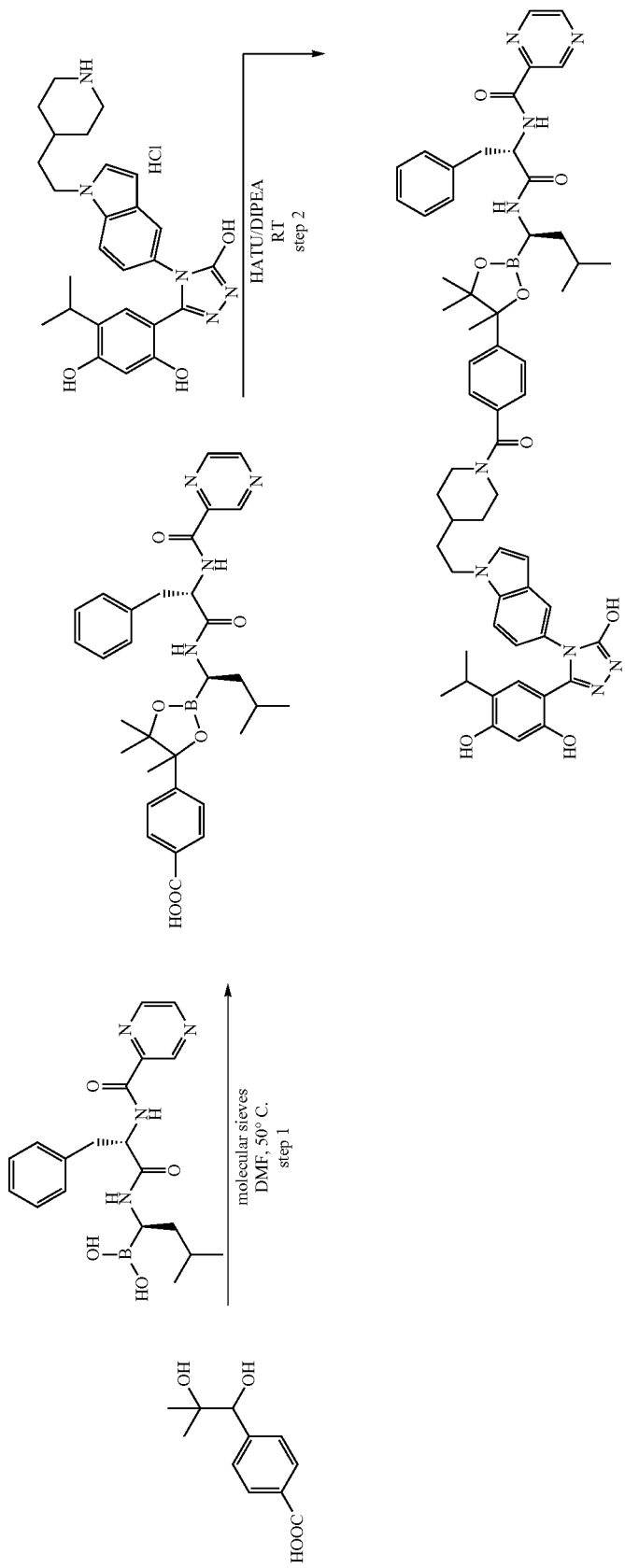

Step 1:

A round-bottomed flask was charged with 4-(2,3-dihydroxy-3-methylbutan-2-yl)benzoic acid (1 mmol), Bortezomib (1 mmol), DMF (10 mL) and 4 Å molecular sieves. The mixture was stirred at 50° C. for 15 h then filtered. The filtrate was concentrated under reduced pressure and the resulting residue was purified by silica gel chromatography ($CH_2Cl_2$/MeOH) to afford 4-(4,5,5-trimethyl-2-((R)-3-methyl-1-((S)-3-phenyl-2-(pyrazine-2-carboxamido)propanamido)butyl)-1,3,2-dioxaborolan-4-yl)benzoic acid as a white solid. ESMS calcd for $C_{31}H_{37}BN_4O_6$: 572.3. found: 573.0 (M+H$^+$).

Step 2:

To a mixture of 4-(4,5,5-trimethyl-2-((R)-3-methyl-1-((S)-3-phenyl-2-(pyrazine-2-carboxamido)propanamido)butyl)-1,3,2-dioxaborolan-4-yl)benzoic acid (0.06 mmol) and 4-(5-hydroxy-4-(1-(2-(piperidin-4-yl)ethyl)-1H-indol-5-yl)-4H-1,2,4-triazol-3-yl)-6-isopropylbenzene-1,3-diol hydrochloride (0.06 mmol) in DMF (1.5 mL) was added HATU (0.072 mmol) followed by diisopropyl ethylamine (0.24 mmol). The reaction mixture was stirred at room temperature overnight then concentrated. The residue was partitioned between ethyl acetate and water. The organic phase was separated, washed with brine, dried ($Na_2SO_4$) and concentrated. The crude product was purified by ISCO using DCM/MeOH as eluent to afford the title compound as a white solid. ESMS calcd for $C_{57}H_{66}BN_9O_8$: 1015.51. found: 1016.1 (M+H$^+$).

SDC-TRAP-0238

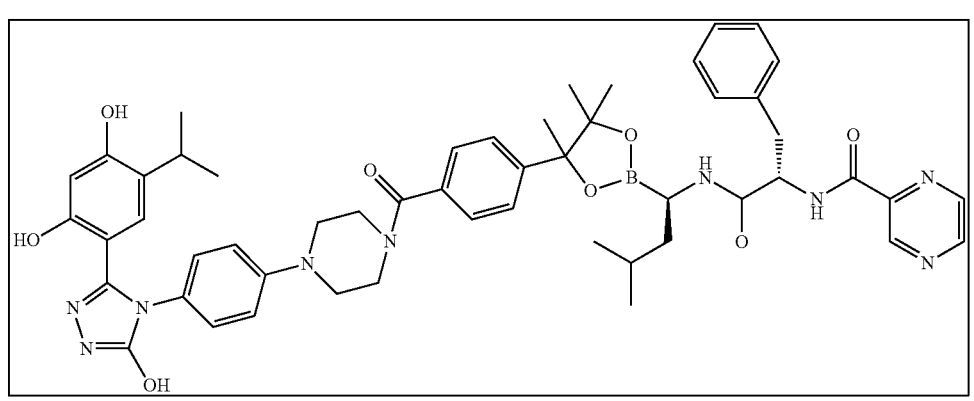

N-((2S)-1-(((1R)-1-(4-(4-(4-(4-(3-(2,4-dihydroxy-5-isopropylphenyl)-5-hydroxy-4H-1,2,4-triazol-4-yl)phenyl)piperazine-1-carbonyl)phenyl)-4,5,5-trimethyl-1,3,2-dioxaborolan-2-yl)-3-methylbutyl)amino)-1-oxo-3-phenylpropan-2-yl)pyrazine-2-carboxamide

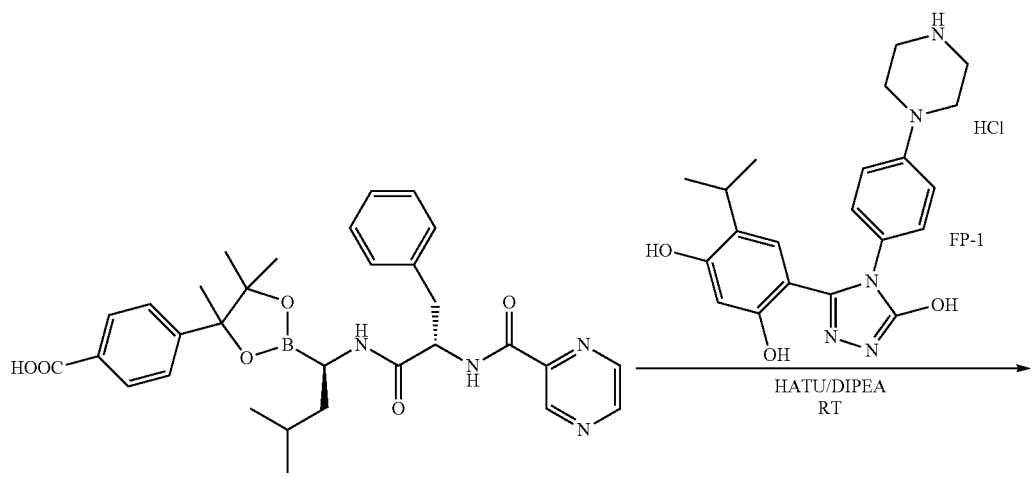

FP-1

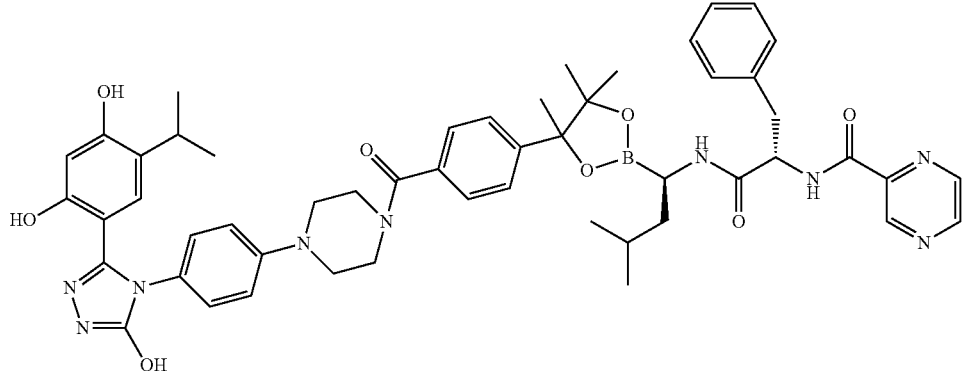

Preparation of SDC-TRAP-0238 followed a similar procedure as for SDC-TRAP-0237, starting from 4-(4,5,5-trimethyl-2-((R)-3-methyl-1-((S)-3-phenyl-2-(pyrazine-2-carboxamido)propanamido)butyl)-1,3,2-dioxaborolan-4-yl)benzoic acid. $^1$H NMR (400 MHz, DMSO-d$_6$) δ 11.83 (s, 1H), 9.64-9.56 (m, 2H), 9.42 (s, 1H), 9.15-9.12 (m, 1H), 9.04-8.97 (m, 1H), 8.89-8.87 (m, 1H), 8.77-8.74 (m, 1H), 7.54-7.49 (m, 2H), 7.36-7.17 (m, 7H), 7.05-6.92 (m, 4H), 6.80 (s, 1H), 6.25 (s, 1H), 5.03-4.94 (m, 1H), 3.8-3.4 (m, 4H), 3.28-3.10 (m, 5H), 2.99-2.94 (m, 2H), 2.56-2.51 (m, 1H), 1.67-1.57 (m, 2H), 1.48-1.41 (m, 3H), 1.41 (s, 3H), 1.30-1.20 (m, 2H), 1.02-0.96 (m, 5H), 0.90-0.82 (m, 6H), 0.63-0.62 (m, 3H) ppm; ESMS calcd for C$_{52}$H$_{60}$BN$_9$O$_8$: 949.47. found: 950.0 (M+H$^+$).

SDC-TRAP-0239

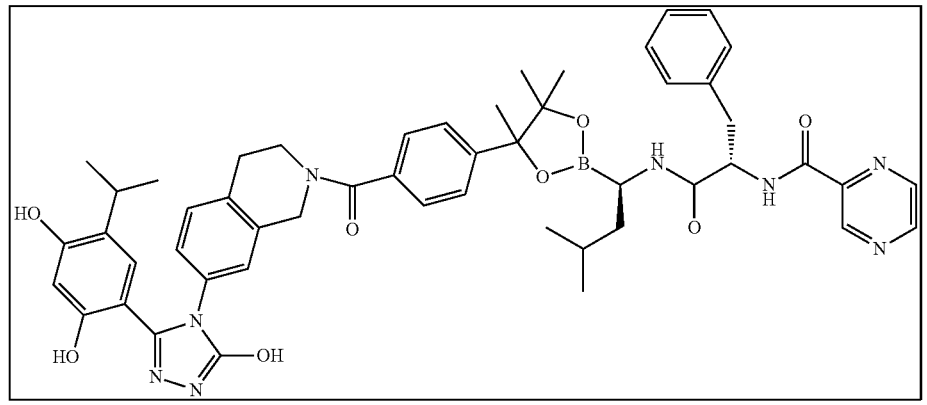

N-((2S)-1-(((1R)-1-(4-(4-(7-(3-(2,4-dihydroxy-5-isopropylphenyl)-5-hydroxy-4H-1,2,4-triazol-4-yl)-1,2,3,4-tetrahydroisoquinoline-2-carbonyl)phenyl)-4,5,5-trimethyl-1,3,2-dioxaborolan-2-yl)-3-methylbutyl)amino)-1-oxo-3-phenylpropan-2-yl)pyrazine-2-carboxamide

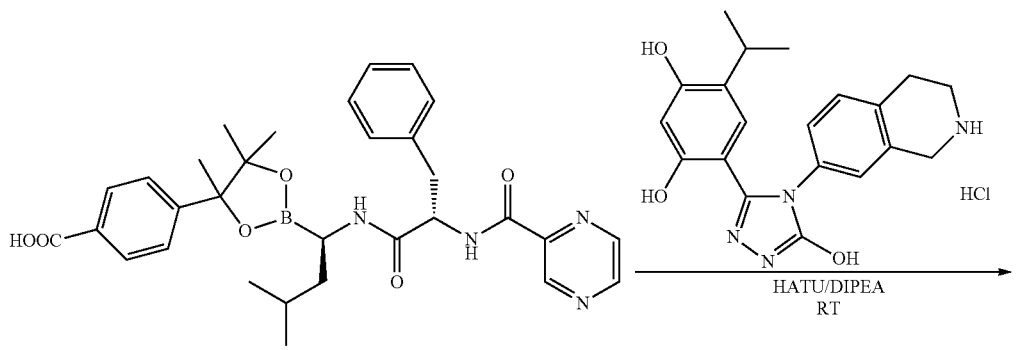

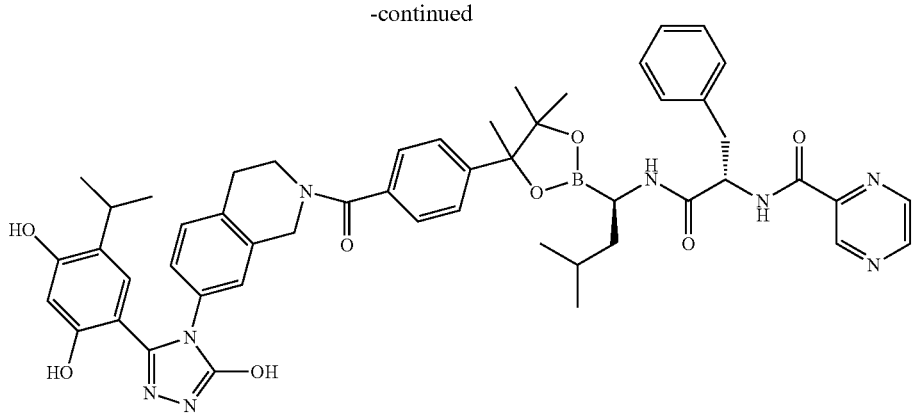

Preparation of SDC-TRAP-0239 followed a similar procedure as for SDC-TRAP-0237, starting from 4-(4,5,5-trimethyl-2-((R)-3-methyl-1-((S)-3-phenyl-2-(pyrazine-2-carboxamido)propanamido)butyl)-1,3,2-dioxaborolan-4-yl)benzoic acid. ESMS calcd for $C_{51}H_{57}BN_8O_8$: 920.44. found: 921.0 (M+H$^+$).

SDC-TRAP-0240

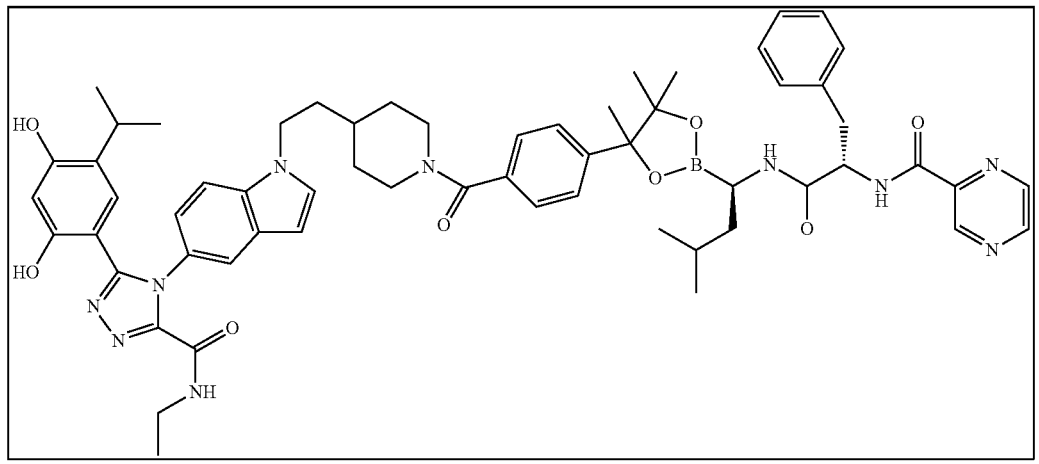

N-((2S)-1-(((1R)-1-(4-(4-(4-(2-(5-(3-(2,4-dihydroxy-5-isopropylphenyl)-5-(ethylcarbamoyl)-4H-1,2,4-triazol-4-yl)-1H-indol-1-yl)ethyl)piperidine-1-carbonyl)phenyl)-4,5,5-trimethyl-1,3,2-dioxaborolan-2-yl)-3-methylbutyl)amino)-1-oxo-3-phenylpropan-2-yl)pyrazine-2-carboxamide

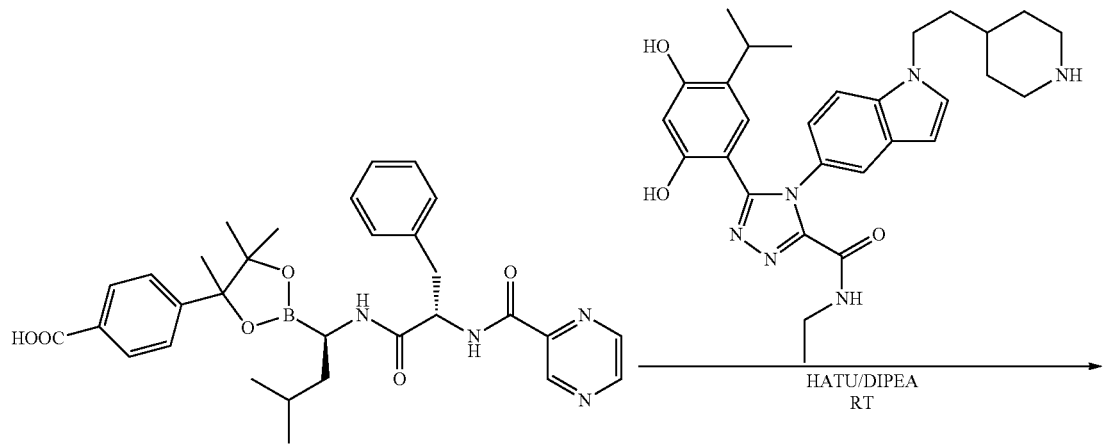

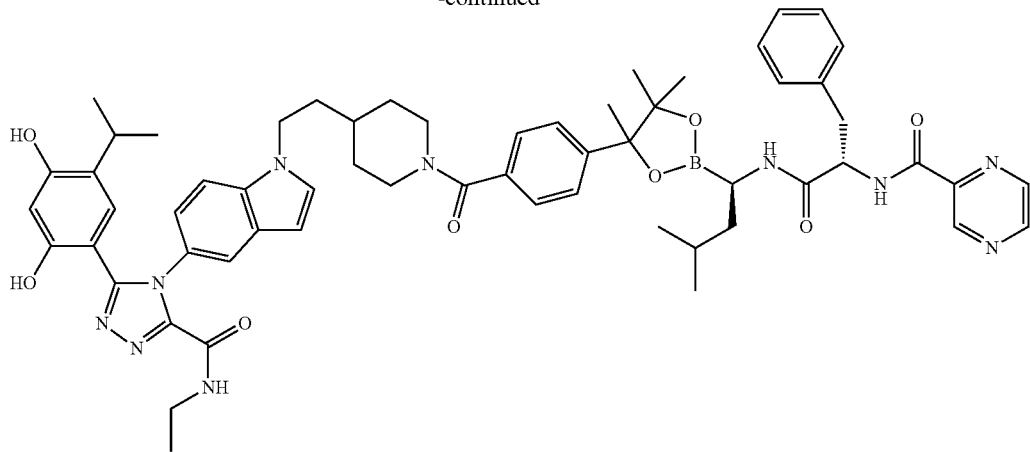

Preparation of SDC-TRAP-0240 followed a similar procedure as for SDC-TRAP-0237, starting from 4-(4,5,5-trimethyl-2-((R)-3-methyl-1-((S)-3-phenyl-2-(pyrazine-2-carboxamido)propanamido)butyl)-1,3,2-dioxaborolan-4-yl)benzoic acid. ESMS calcd for $C_{60}H_{71}BN_{10}O_8$: 1070.55. found: 1071.10 (M+H$^+$).

SDC-TRAP-0241

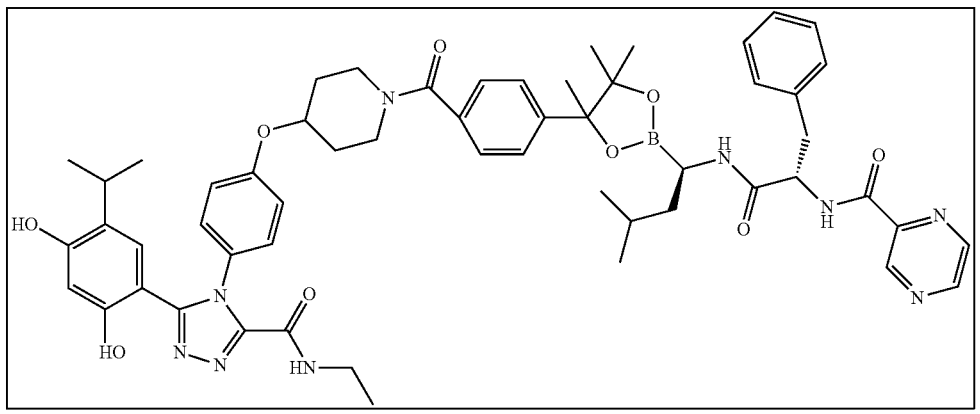

N-((2S)-1-(((1R)-1-(4-(4-(4-(4-(3-(2,4-dihydroxy-5-isopropylphenyl)-5-(ethylcarbamoyl)-4H-1,2,4-triazol-4-yl)phenoxy)piperidine-1-carbonyl)phenyl)-4,5,5-trimethyl-1,3,2-dioxaborolan-2-yl)-3-methylbutyl)amino)-1-oxo-3-phenylpropan-2-yl)pyrazine-2-carboxamide

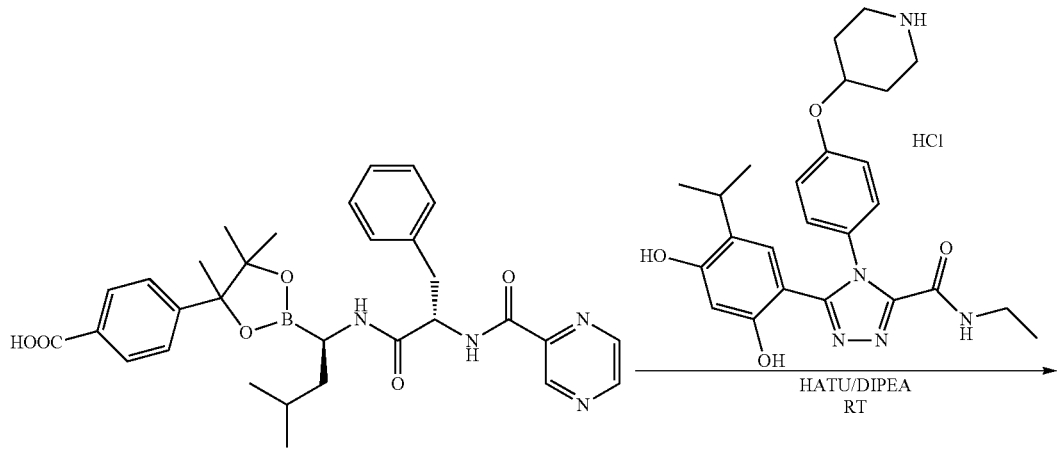

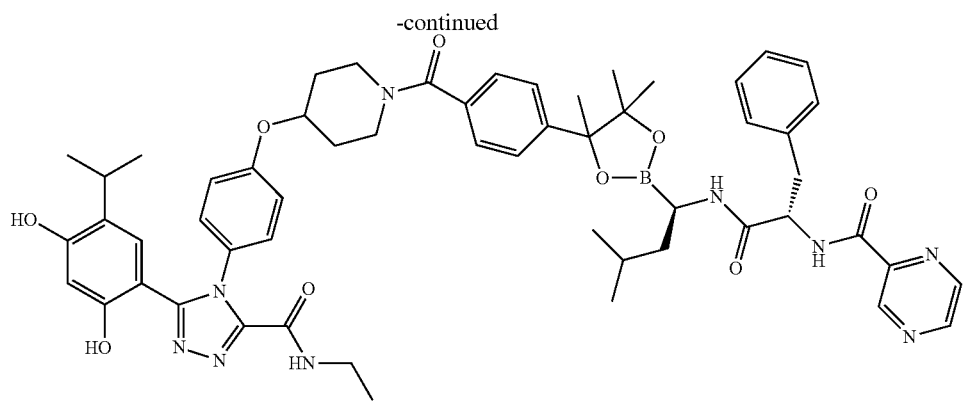

Preparation of SDC-TRAP-0241 followed a similar procedure as for SDC-TRAP-0237, starting from 4-(4,5,5-trimethyl-2-((R)-3-methyl-1-((S)-3-phenyl-2-(pyrazine-2-carboxamido)propanamido)butyl)-1,3,2-dioxaborolan-4-yl)benzoic acid. ESMS calcd for $C_{56}H_{66}BN_9O_9$: 1019.51. found: 1020.10 (M+H$^+$).

SDC-TRAP-0242

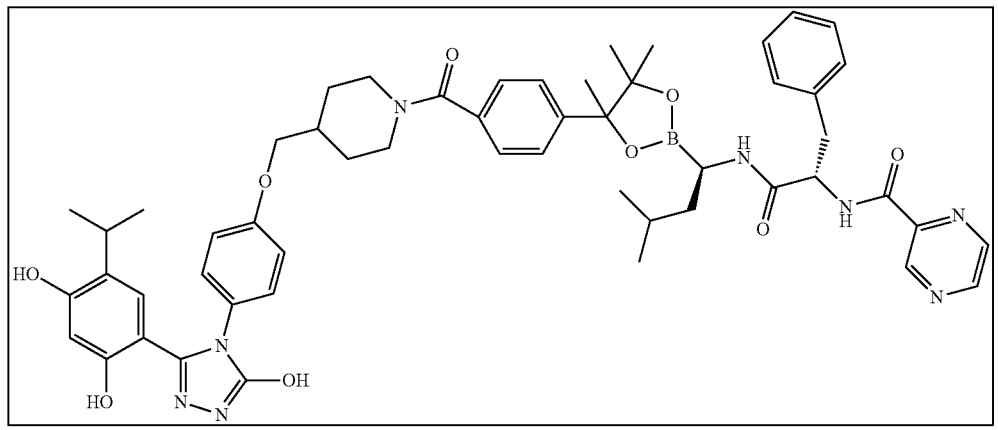

N-((2S)-1-(((1R)-1-(4-(4-(4-((4-(3-(2,4-dihydroxy-5-isopropylphenyl)-5-hydroxy-4H-1,2,4-triazol-4-yl)phenoxy)methyl)piperidine-1-carbonyl)phenyl)-4,5,5-trimethyl-1,3,2-dioxaborolan-2-yl)-3-methylbutyl)amino)-1-oxo-3-phenylpropan-2-yl)pyrazine-2-carboxamide

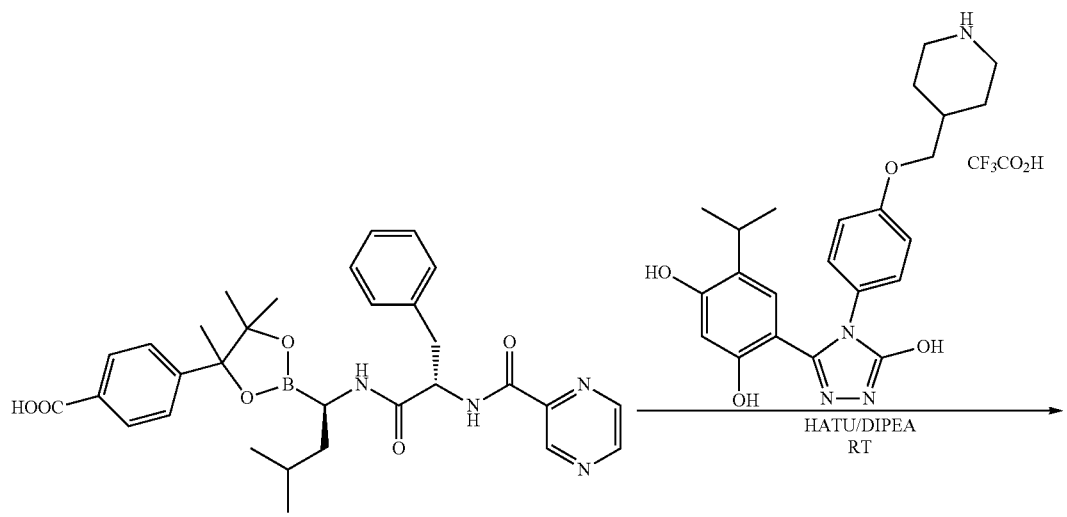

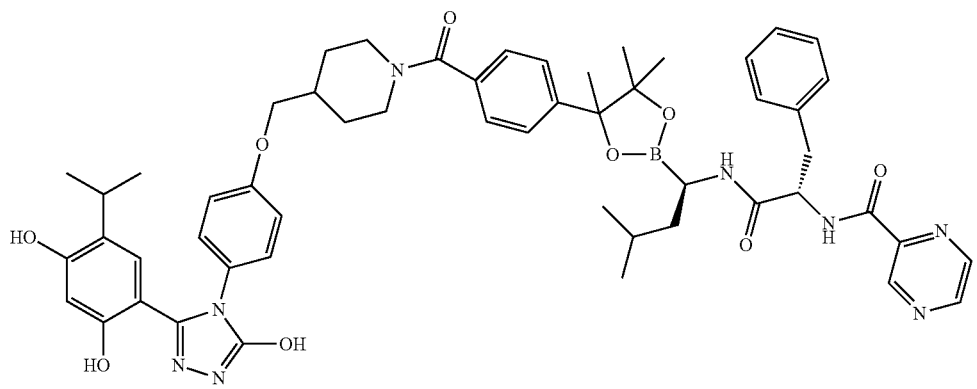
Preparation of SDC-TRAP-0242 followed a similar procedure as for SDC-TRAP-0237, starting from 4-(4,5,5-trimethyl-2-((R)-3-methyl-1-((S)-3-phenyl-2-(pyrazine-2-carboxamido)propanamido)butyl)-1,3,2-dioxaborolan-4-yl) benzoic acid. ESMS calcd for $C_{54}H_{63}BN_8O_9$: 978.48. found: 979.1 (M+H$^+$).
SDC-TRAP-0243
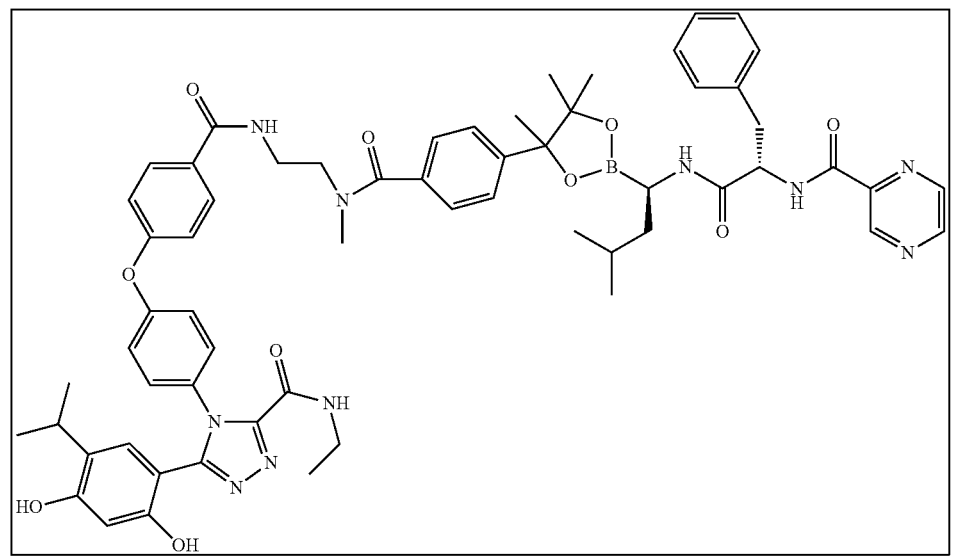

N-((2S)-1-(((1R)-1-(4-(4-((2-(4-(4-(3-(2,4-dihydroxy-5-isopropylphenyl)-5-(ethylcarbamoyl)-4H-1,2,4-triazol-4-yl)phenoxy)benzamido)ethyl)(methyl)carbamoyl)phenyl)-4,5,5-trimethyl-1,3,2-dioxaborolan-2-yl)-3-methylbutyl)amino)-1-oxo-3-phenylpropan-2-yl)pyrazine-2-carboxamide
5
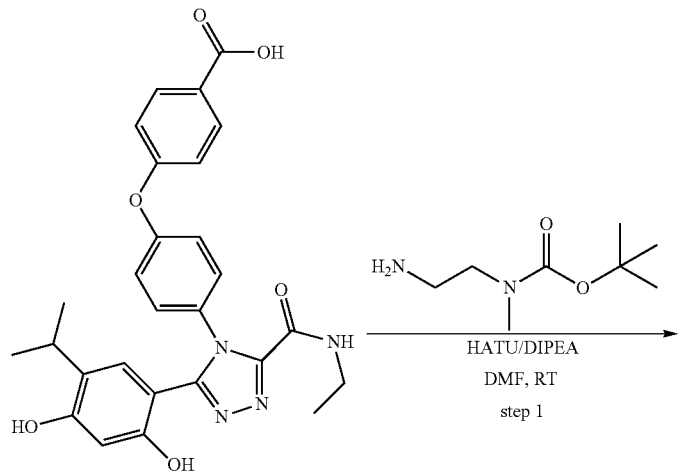
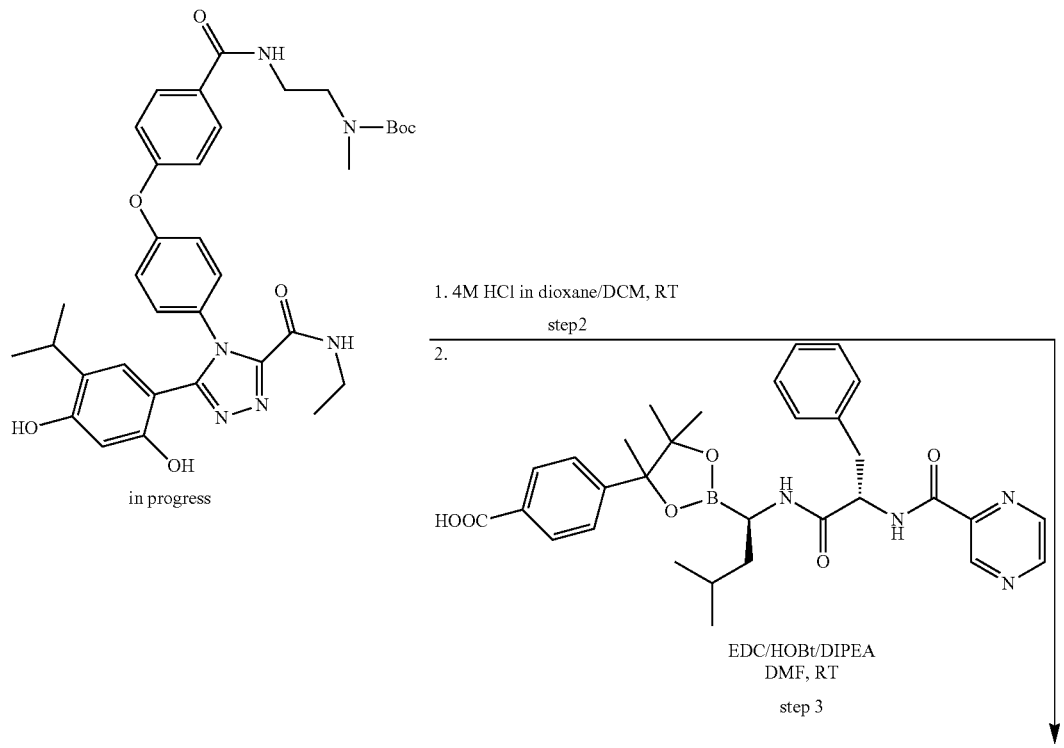
in progress

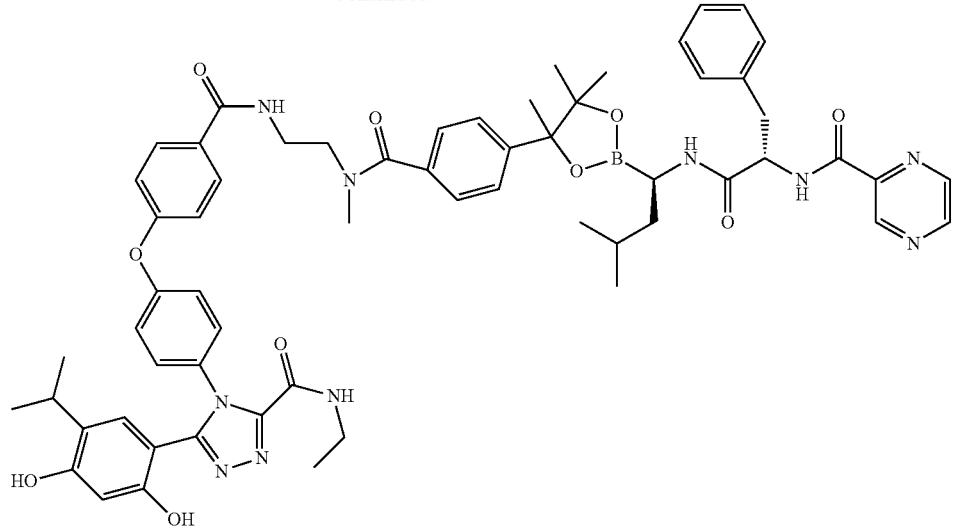

Step 1:

To a mixture of 4-(4-(3-(2,4-dihydroxy-5-isopropylphenyl)-5-(ethylcarbamoyl)-4H-1,2,4-triazol-4-yl)phenoxy)benzoic acid (1 mmol) tert-butyl (2-aminoethyl)(methyl)carbamate (1.1 mmol) in DMF (10 mL) was added HATU (1.25 mmol) followed by diisopropyl ethylamine (4 mmol). The reaction mixture was stirred at room temperature overnight then concentrated. The residue was partitioned between ethyl acetate and water. The organic phase was separated, washed with brine, dried ($Na_2SO_4$) and concentrated. The crude product was purified by ISCO using DCM/MeOH as eluent to afford the tert-butyl (2-(4-(4-(3-(2,4-dihydroxy-5-isopropylphenyl)-5-(ethylcarbamoyl)-4H-1,2,4-triazol-4-yl)phenoxy)benzamido)ethyl)(methyl)carbamate as a white solid. ESMS calcd for $C_{35}H_{42}BN_6O_7$: 658.31. found: 659.0 (M+H$^+$).

Step 2:

To a solution of tert-butyl (2-(4-(4-(3-(2,4-dihydroxy-5-isopropylphenyl)-5-(ethylcarbamoyl)-4H-1,2,4-triazol-4-yl)phenoxy)benzamido)ethyl)(methyl)carbamate (0.91 mmol) in DCM (5 mL) was added 4M HCl in dioxane (5 mL). The mixture was stirred at room temperature overnight. Nitrogen was bubbled into the solution to remove excess HCl. Diethyl ether was added, the resulting 5-(2,4-dihydroxy-5-isopropylphenyl)-N-ethyl-4-(4-(4-((2-(methylamino)ethyl)carbamoyl)phenoxy)phenyl)-4H-1,2,4-triazole-3-carboxamide hydrochloride was filtered, dried on high-vacuum.

Step 3:

To a mixture of 5-(2,4-dihydroxy-5-isopropylphenyl)-N-ethyl-4-(4-(4-((2-(methylamino)ethyl)carbamoyl)phenoxy)phenyl)-4H-1,2,4-triazole-3-carboxamide hydrochloride (0.073 mmol), 4-(4,5,5-trimethyl-2-((R)-3-methyl-1-((S)-3-phenyl-2-(pyrazine-2-carboxamido)propanamido)butyl)-1,3,2-dioxaborolan-4-yl)benzoic acid 90.07 mmol), EDCI (0.087 mmol) in DMF (1.5 mL) was added HOBt (0.087 mmol) followed by DIPEA (0.23 mmol).

The reaction mixture was stirred at room temperature overnight then concentrated. The residue was partitioned between ethyl acetate and water. The organic phase was separated, washed with brine, dried ($Na_2SO_4$) and concentrated. The crude product was purified by ISCO using DCM/MeOH as eluent to afford the title compound as a white solid. ESMS calcd for $C_{61}H_{69}BN_{10}O_{10}$: 1112.53. found: 1113.10 (M+H$^+$).

The compounds 2-((3aR,4R,6R,7 aS)-2,2,5,5-tetramethylhexahydro-4,6-methanobenzo[d][1,3]dioxol-3a-yl)ethanol and 2-((3aR,4R,6R,7 aS)-2,2,5,5-tetramethylhexahydro-4,6-methanobenzo[d][1,3]dioxol-3a-yl)acetic acid were prepared following below scheme and procedures in reference WO 2005/119255.

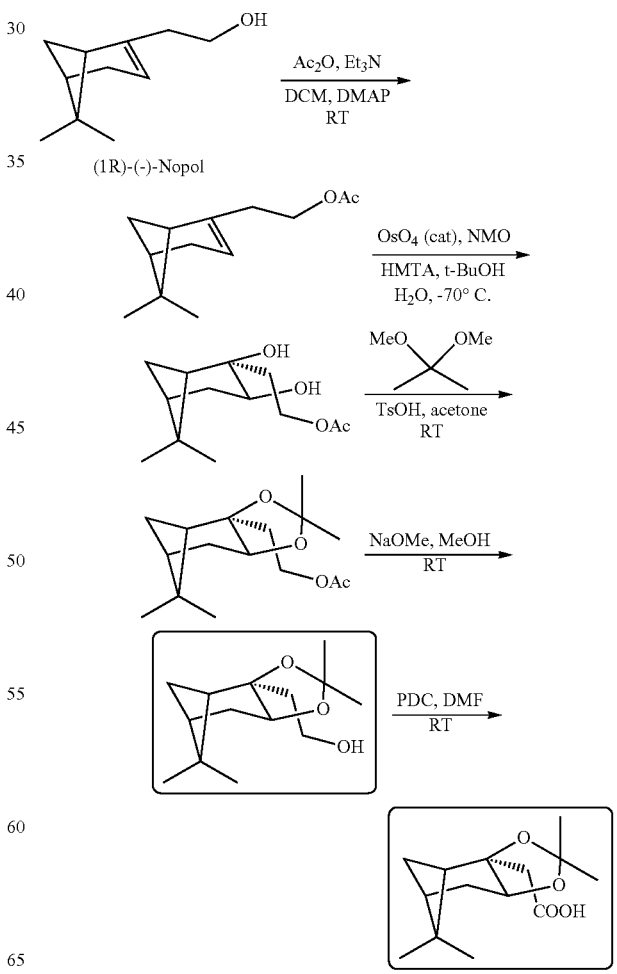

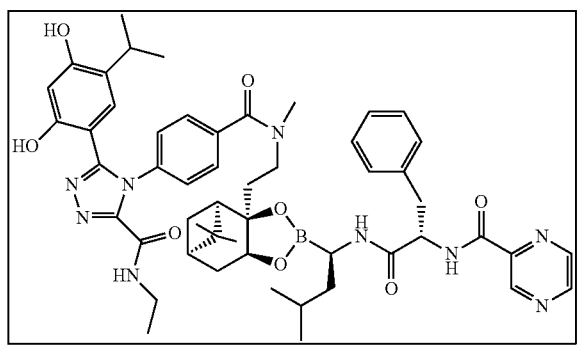
SDC-TRAP-0244
N—((S)-1-(((R)-1-((3aR,4R,6R,7aS)-3a-(2-(4-(3-(2,4-dihydroxy-5-isopropylphenyl)-5-(ethylcarbamoyl)-4H-1,2,4-triazol-4-yl)-N-methylbenzamido)ethyl)-5,5-dimethylhexahydro-4,6-methanobenzo[d][1,3,2]dioxaborol-2-yl)-3-methylbutyl)amino)-1-oxo-3-phenylpropan-2-yl)pyrazine-2-carboxamide
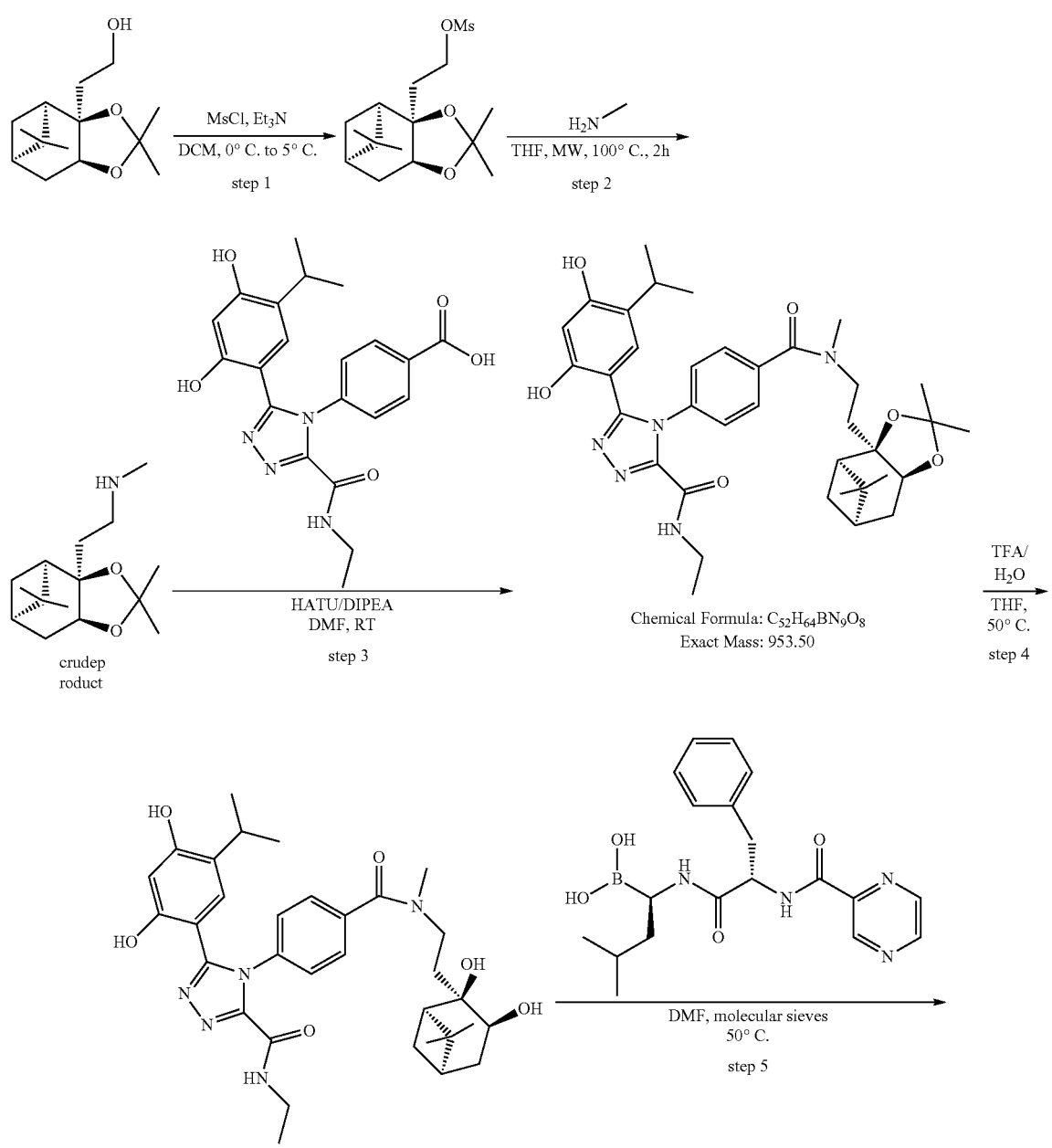

-continued

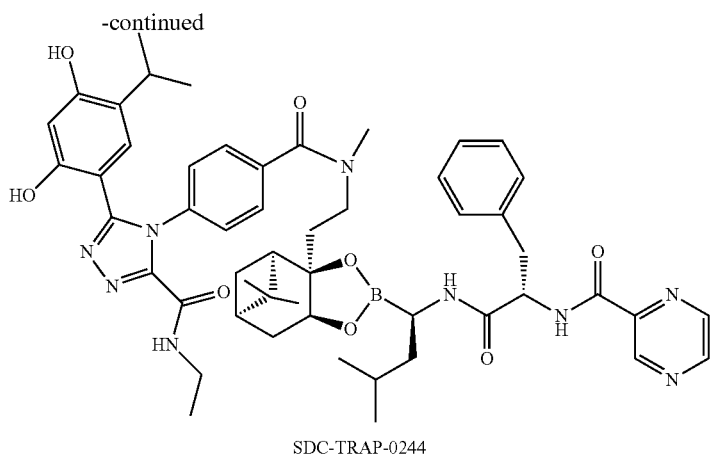

SDC-TRAP-0244

Step 1:
To a solution of 2-((3aR,4R,6R,7aS)-2,2,5,5-tetramethylhexahydro-4,6-methanobenzo[d][1,3]dioxol-3a-yl)ethanol (1 mmol) in DCM (6 mL) at 0° C. was added Et₃N (2.2 mmol) followed by MsCl (1.1 mmol). The reaction mixture was stirred between 0-5° C. for 2 h. The mixture was quenched with water, extracted with DCM, dried (Na₂SO₄), filtered, concentrated and dried on high vacuum to get crude mesylate.

Step 2:
The above crude mesylate and 2M MeNH₂ in THF (20 mL) were taken in microwave tube, heated in the microwave at 100° C. for 2 h. The solution was concentrated, residue partitioned between DCM and aq. NaHCO₃. The organic layer was separated, dried (Na₂SO₄), filtered, concentrated and dried on high vacuum.

Step 3:
The above crude amine and 4-(3-(2,4-dihydroxy-5-isopropylphenyl)-5-(ethylcarbamoyl)-4H-1,2,4-triazol-4-yl) benzoic acid (0.5 mmol) were dissolved in DMF (5 mL), treated with HATU (0.6 mmol) and DIPEA (1.5 mmol). The reaction mixture was stirred at room temperature overnight, concentrated. The residue was dissolved in ethyl acetate, washed with water, dried (Na₂SO₄), filtered, concentrated. The crude product was purified by ISCO using DCM/MeOH as eluent to afford the 5-(2,4-dihydroxy-5-isopropylphenyl)-N-ethyl-4-(4-(methyl(2-((3aR,4R,6R,7aS)-2,2,5,5-tetramethylhexahydro-4,6-methanobenzo[d][1,3]dioxol-3a-yl) ethyl)carbamoyl)phenyl)-4H-1,2,4-triazole-3-carboxamide.

Step 4:
The above 5-(2,4-dihydroxy-5-isopropylphenyl)-N-ethyl-4-(4-(methyl(2-((3aR,4R,6R,7aS)-2,2,5,5-tetramethylhexahydro-4,6-methanobenzo[d][1,3]dioxol-3a-yl)ethyl)carbamoyl)phenyl)-4H-1,2,4-triazole-3-carboxamide (0.23 mmol) was dissolved in THF (1 mL) and treated with TFA/H₂O (1/1, 5 mL). The mixture was heated at 50° C. for 3 h, then concentrated. The residue was dissolved in ethyl acetate, washed with aq. NaHCO₃, dried (Na₂SO₄), filtered, concentrated. The crude product was purified by ISCO using DCM/MeOH as eluent to afford the 5-(2,4-dihydroxy-5-isopropylphenyl)-4-(4-((2-((1R,2R,3S,5R)-2,3-dihydroxy-6,6-di methylbicyclo[3.1.1]heptan-2-yl)ethyl)(methyl)carbamoyl)phenyl)-N-ethyl-4H-1,2,4-triazole-3-carboxamide.

Step 5:
A round-bottomed flask was charged with 5-(2,4-dihydroxy-5-isopropylphenyl)-4-(4-((2-((1R,2R,3S,5R)-2,3-dihydroxy-6,6-di methylbicyclo[3.1.1]heptan-2-yl)ethyl)(methyl)carbamoyl)phenyl)-N-ethyl-4H-1,2,4-triazole-3-carboxamide (0.076 mmol), Bortezomib (0.091 mmol), DMF (1 mL) and 4 Å molecular sieves (100 mg). The mixture was stirred at 50° C. for 15 h then filtered. The filtrate was concentrated under reduced pressure and the resulting residue was purified by silica gel chromatography (CH₂Cl₂/MeOH) then by reverse phase chromatography (ACN/H₂O with HCOOH) to afford the title product as a white solid. ESMS calcd for $C_{52}H_{64}BN_9O_8$: 953.50. found: 954.1 (M+H⁺).

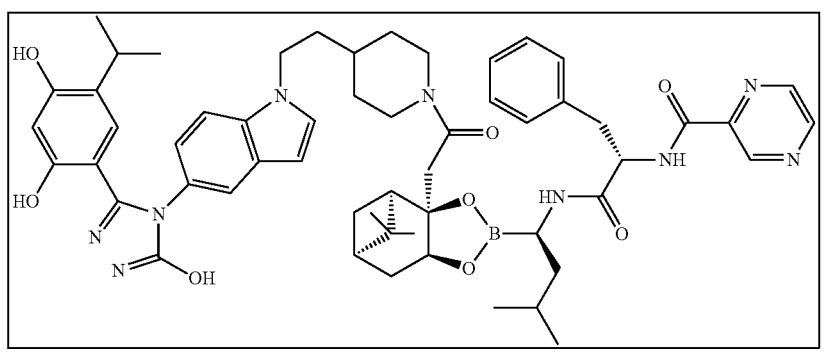

SDC-TRAP-0245

N—((S)-1-(((R)-1-((3aR,4R,6R,7aS)-3a-(2-(4-(2-(5-(3-(2,4-dihydroxy-5-iso propylphenyl)-5-hydroxy-4H-1,2,4-triazol-4-yl)-1H-indol-1-yl)ethyl)piperidin-1-yl)-2-oxoethyl)-5,5-dimethylhexahydro-4,6-methanobenzo[d][1,3,2]dioxaborol-2-yl)-3-methylbutyl)amino)-1-oxo-3-phenylpropan-2-yl) pyrazine-2-carboxamide 6-methanobenzo[d][1,3]dioxol-3a-yl)ethanone as a white solid.

Step 2:

The above 1-(4-(2-(5-(3-(2,4-dihydroxy-5-isopropylphenyl)-5-hydroxy-4H-1,2,4-triazol-4-yl)-1H-indol-1-yl)ethyl)piperidin-1-yl)-2-((3aR,4R,6R,7 aS)-2,2,5,5-tetramethyl-hexahydro-4,6-methanobenzo[d][1,3]dioxol-3a-yl)ethanone

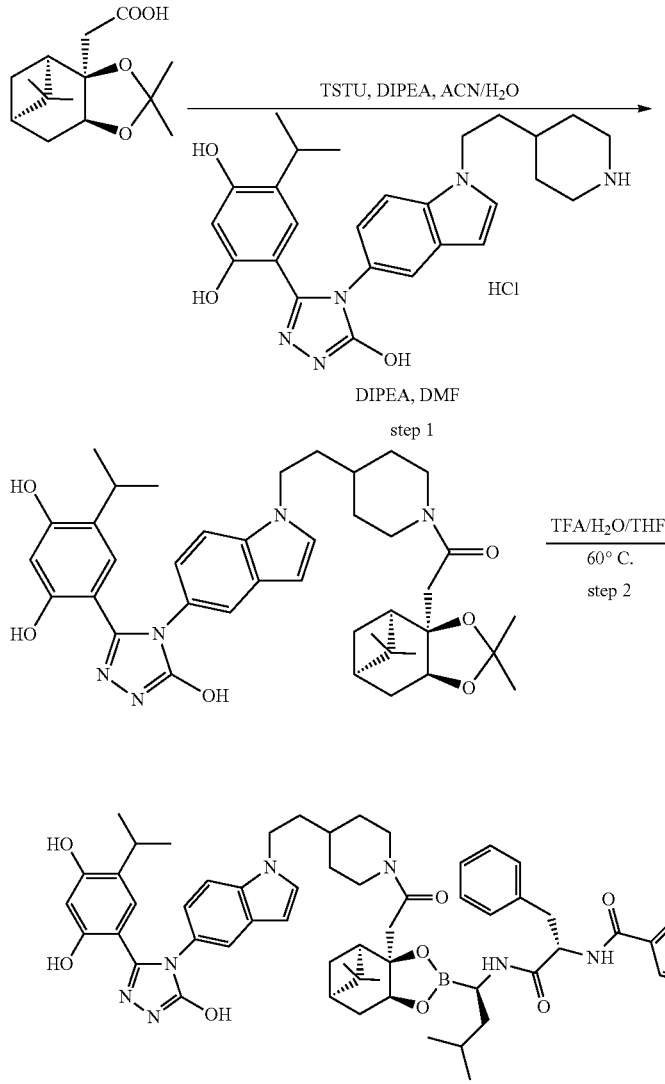

Step 1:

To a mixture of 2-((3aR,4R,6R,7 aS)-2,2,5,5-tetramethylhexahydro-4,6-methanobenzo[d][1,3]dioxol-3a-yl)acetic acid (0.5 mmol) and TSTU 90.75 mmol) in 20% H2O in CH3CN (2.8 mL) was added DIPEA (1.5 mmol). The mixture was stirred at room temperature for 1 h, then treated with a mixture of 4-(5-hydroxy-4-(1-(2-(piperidin-4-yl)ethyl)-1H-indol-5-yl)-4H-1,2,4-triazol-3-yl)-6-isopropyl-benzene-1,3-diol hydrochloride (0.62 mmol) and DIPEA (1.5 mmol) in DMF 92.8 mL). The reaction mixture was stirred at room temperature overnight, concentrated. The residue was dissolved in ethyl acetate, washed with water, dried (Na2SO4), filtered, concentrated. The crude product was purified by ISCO using DCM/MeOH as eluent to afford the 1-(4-(2-(5-(3-(2,4-dihydroxy-5-isopropylphenyl)-5-hydroxy-4H-1,2,4-triazol-4-yl)-1H-indol-1-yl)ethyl)piperidin-1-yl)-2-((3aR,4R,6R,7 aS)-2,2,5,5-tetramethylhexahydro-4,6-

(0.23 mmol) was dissolved in THF (3 mL) and treated with TFA/H2O (1/1.4 mL). The mixture was heated at 60° C. for 4 h, then concentrated. The residue was dissolved in ethyl acetate, washed with water, dried (Na2SO4), filtered, concentrated. The crude product was purified by ISCO using DCM/MeOH as eluent to afford the 1-(4-(2-(5-(3-(2,4-dihydroxy-5-isopropylphenyl)-5-hydroxy-4H-1,2,4-triazol-4-yl)-1H-indol-1-yl)ethyl)piperidin-1-yl)-2-((1R,2R,3S,5R)-2,3-dihydroxy-6,6-dimethylbicyclo[3.1.1]heptan-2-yl) ethanone as a white solid.

Step 3:

A round-bottomed flask was charged with 1-(4-(2-(5-(3-(2,4-dihydroxy-5-isopropylphenyl)-5-hydroxy-4H-1,2,4-triazol-4-yl)-1H-indol-1-yl)ethyl)piperidin-1-yl)-2-((1R,2R,3S,5R)-2,3-dihydroxy-6,6-dimethylbicyclo[3.1.1]heptan-2-yl)ethanone (0.079 mmol), Bortezomib (0.1 mmol), DMF (1 mL) and 4 Å molecular sieves (100 mg). The mixture was stirred at 50° C. for 15 h then filtered. The filtrate was concentrated under reduced pressure and the resulting residue was purified by silica gel chromatography (CH$_2$Cl$_2$/MeOH) then by reverse phase chromatography (ACN/H$_2$O with HCOOH) to afford the title product as a white solid.

ESMS calcd for C$_{56}$H$_{68}$BN$_9$O$_8$: 1005.53. found: 1006.1 (M+H$^+$).

The compound 9-amino-2,3-dimethylnonane-2,3-diol was prepared according to the procedure referenced in WO 2011/146638.

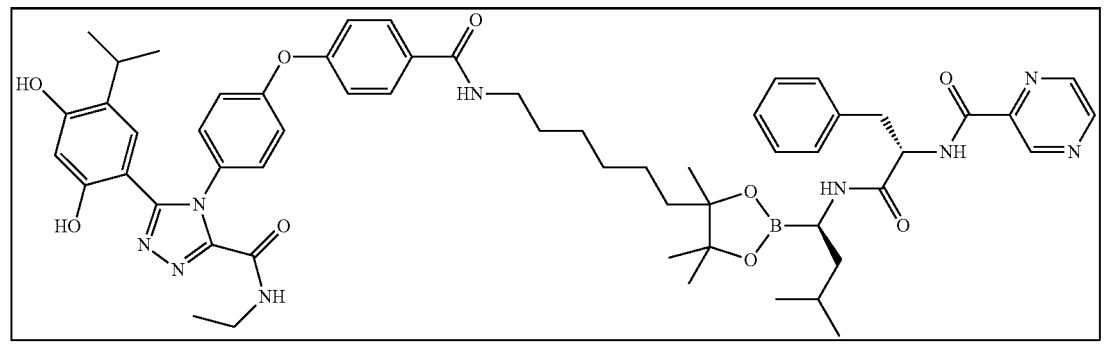

SDC-TRAP-0246

N-((2S)-1-(((1R)-1-(4-(6-(4-(4-(3-(2,4-dihydroxy-5-isopropylphenyl)-5-(ethylcarbamoyl)-4H-1,2,4-triazol-4-yl)phenoxy)benzamido)hexyl)-4,5,5-trimethyl-1,3,2-dioxaborolan-2-yl)-3-methylbutyl)amino)-1-oxo-3-phenylpropan-2-yl)pyrazine-2-carboxamide

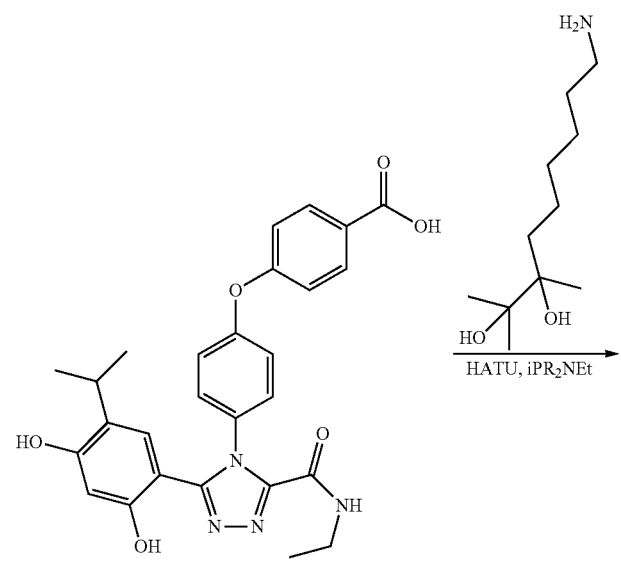

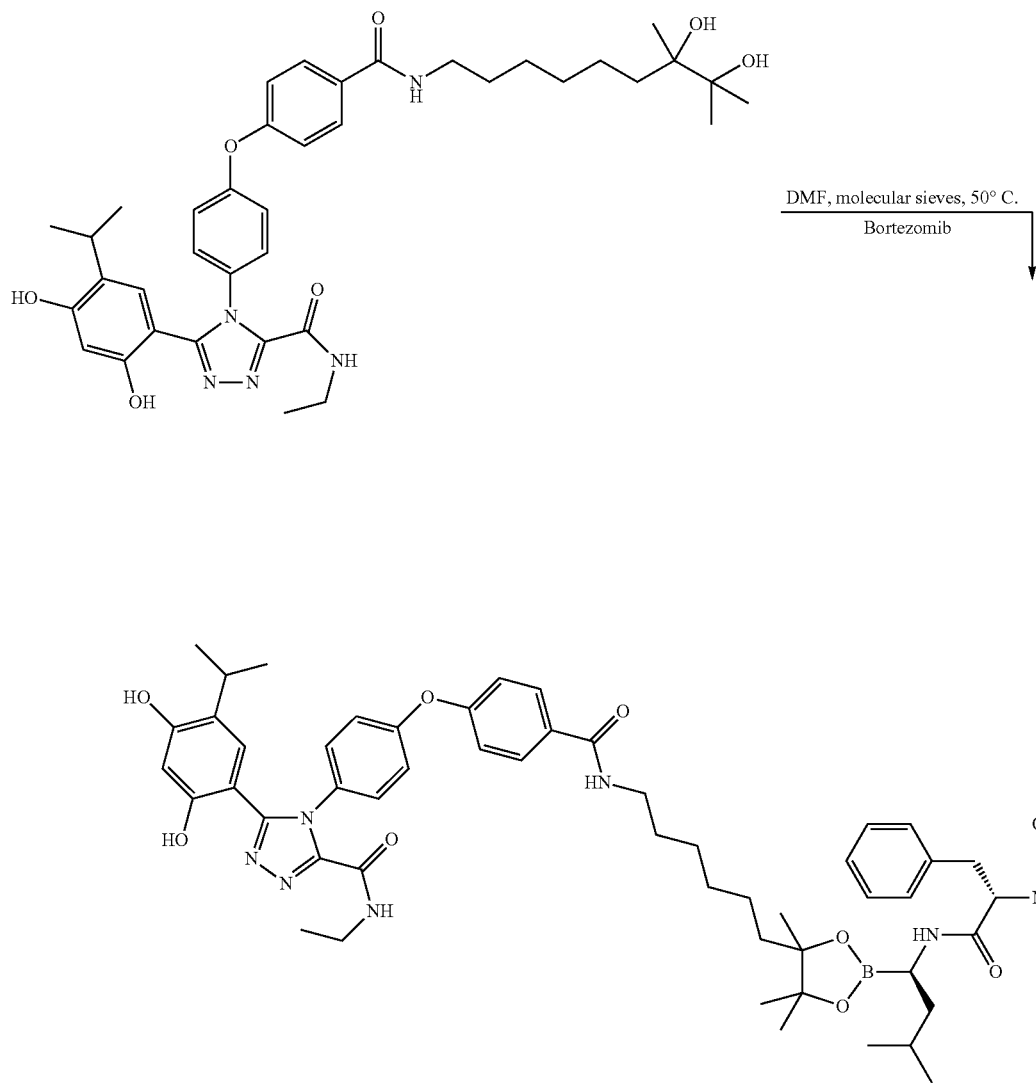

4-(4-(3-(2,4-dihydroxy-5-isopropylphenyl)-5-(ethylcarbamoyl)-4H-1,2,4-triazol-4-yl)phenoxy)benzoic acid (0.20 mmol) was dissolved in DMF (1 mL), followed by the addition of 9-amino-2,3-dimethylnonane-2,3-diol (0.26 mmol), HATU (0.30 mmol) and diisopropyl ethylamine (0.60 mmol). The solution was stirred at 23° C. for 5.5 h. The solution was concentrated under reduced pressure, and the resulting residue was purified by silica gel chromatography (CH$_2$Cl$_2$/MeOH) to afford 5-(2,4-dihydroxy-5-isopropylphenyl)-4-(4-(4-((7,8-dihydroxy-7,8-dimethylnonyl)carbamoyl)phenoxy)phenyl)-N-ethyl-4H-1,2,4-triazole-3-carboxamide as a white solid.

A round-bottomed flask was charged with 5-(2,4-dihydroxy-5-isopropylphenyl)-4-(4-(4-((7,8-dihydroxy-7,8-dimethylnonyl)carbamoyl)phenoxy)phenyl)-N-ethyl-4H-1,2,4-triazole-3-carboxamide (0.11 mmol), Bortezomib (0.09 mmol), DMF (1 mL) and 4 Å molecular sieves (106 mg). The mixture was stirred in a 50° C. oil bath for 15 h, then the solvent was removed under reduced pressure. The resulting residue was purified by silica gel chromatography (CH$_2$Cl$_2$/MeOH) to afford SDC-TRAP-0246 as a white solid.

$^1$H NMR (400 MHz, DMSO-d6), δ 10.47 (s, 1H), 9.80 (s, 1H), 9.11 (dd, J=1.2 Hz, 1H), 8.97 (dd, J=6.0, 6.0 Hz, 1H), 8.90-8.85 (m, 2H), 8.78-8.72 (m, 2H), 8.41-8.39 (m, 1H), 7.89 (d, J=8.8 Hz, 2H), 7.38 (d, J=8.8 Hz, 2H), 7.25-7.19 (m, 4H), 7.17-7.15 (m, 1H), 7.10-7.05 (m, 4H), 6.67 (s, 1H), 6.35 (s, 1H), 4.86 (ddd, J=7.2, 7.2, 7.2 Hz, 1H), 3.24-3.17 (m, 4H), 3.12-3.09 (m, 2H), 2.97 (ddd, J=6.8, 6.8, 6.8 Hz, 1H), 2.64-2.57 (m, 1H), 1.56-1.17 (m, 13H), 1.12 (s, 3H), 1.10 (s, 3H), 1.07 (s, 3H), 1.05 (d, J=6.8 Hz, 6H), 0.92 (d, J=6.8 Hz, 6H), 0.81 (t, J=6.0 Hz, 3H) ppm; ESMS calcd for C$_{57}$H$_{70}$BN$_9$O$_9$: 1035.5. found: 1036.0 (M+H$^+$).

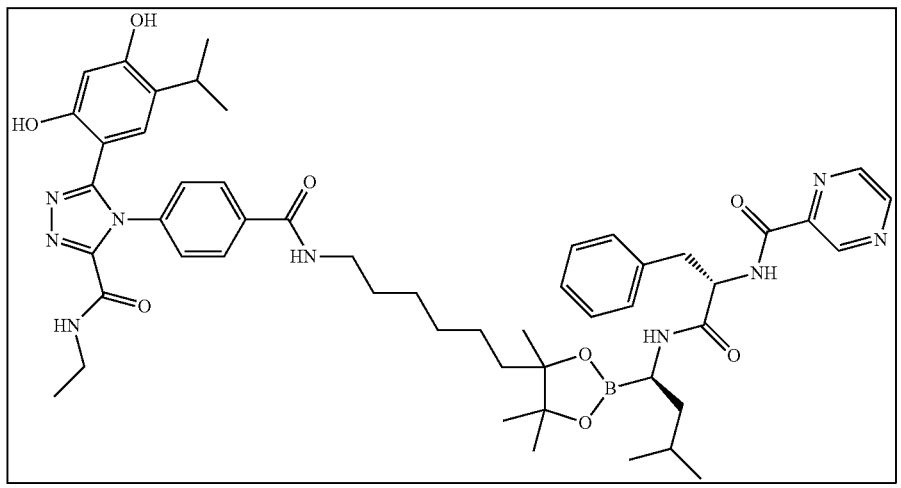

SDC-TRAP-0247

N-((2S)-1-(((1R)-1-(4-(6-(4-(3-(2,4-dihydroxy-5-isopropylphenyl)-5-(ethylcarbamoyl)-4H-1,2,4-triazol-4-yl)benzamido)hexyl)-4,5,5-trimethyl-1,3,2-dioxaborolan-2-yl)-3-methylbutyl)amino)-1-oxo-3-phenylpropan-2-yl)pyrazine-2-carboxamide

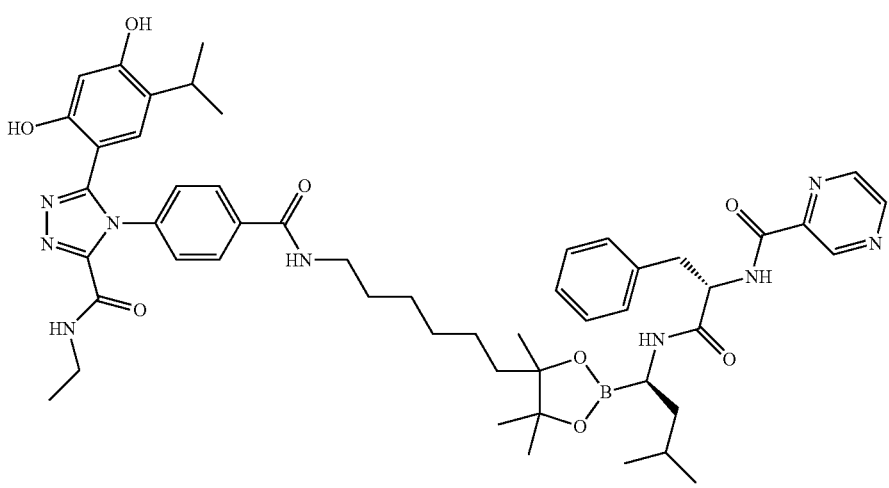 [SMILES: CCNC(=O)c1nnc(-c2cc(C(C)C)c(O)cc2O)n1-c1ccc(C(=O)NCCCCCCC2(C)OB([C@H](CC(C)C)NC(=O)[C@H](Cc3ccccc3)NC(=O)c3cnccn3)OC2(C)C)cc1]

Preparation of SDC-TRAP-0247 followed a similar procedure as for SDC-TRAP-0246, starting from 4-(3-(2,4-dihydroxy-5-isopropylphenyl)-5-(ethylcarbamoyl)-4H-1,2,4-triazol-4-yl)benzoic acid.

ESMS calcd for $C_{51}H_{66}BN_9O_8$: 943.5. found: 944.2 (M+H$^+$).

97
SDC-TRAP-0248
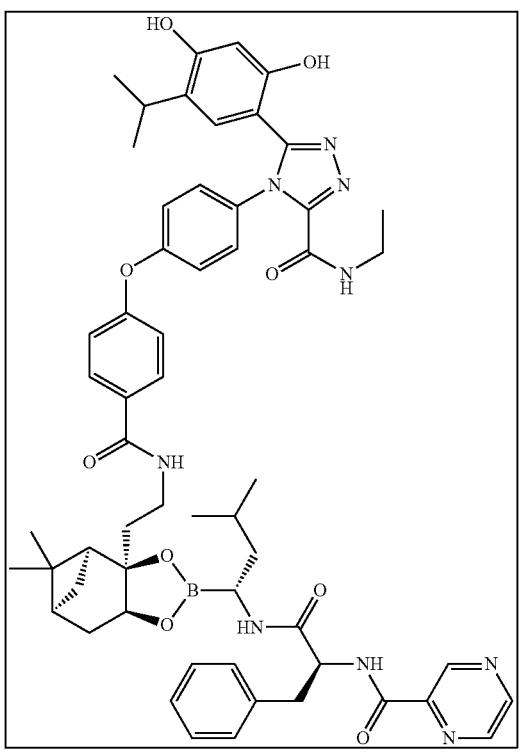
98
N—((S)-1-(((R)-1-((3aR,4S,6S,7aS)-3a-(2-(4-(4-(3-(2,4-dihydroxy-5-isopropylphenyl)-5-(ethylcarbamoyl)-4H-1,2,4-triazol-4-yl)phenoxy)benzamido)ethyl)-5,5-dimethylhexahydro-4,6-methanobenzo[d][1,3,2]dioxaborol-2-yl)-3-methylbutyl)amino)-1-oxo-3-phenylpropan-2-yl)pyrazine-2-carboxamide
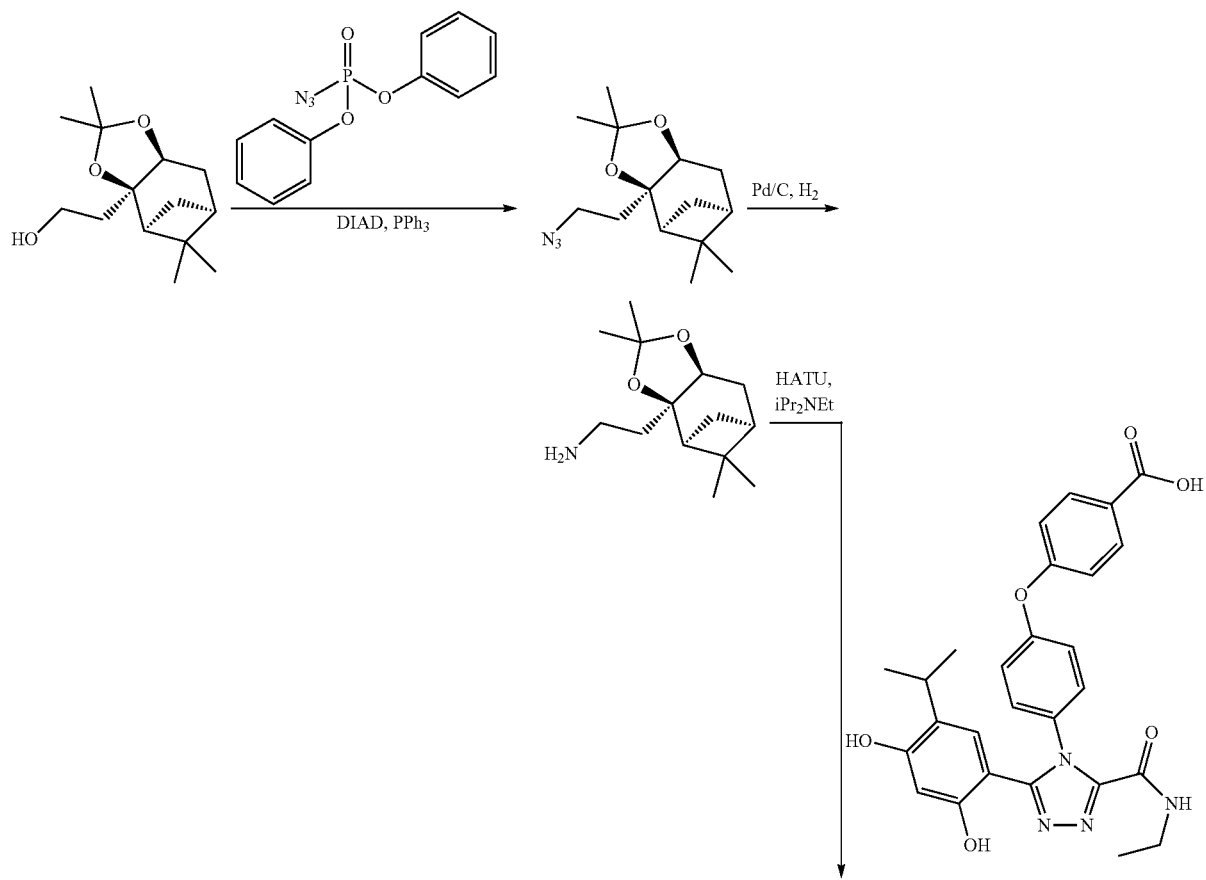

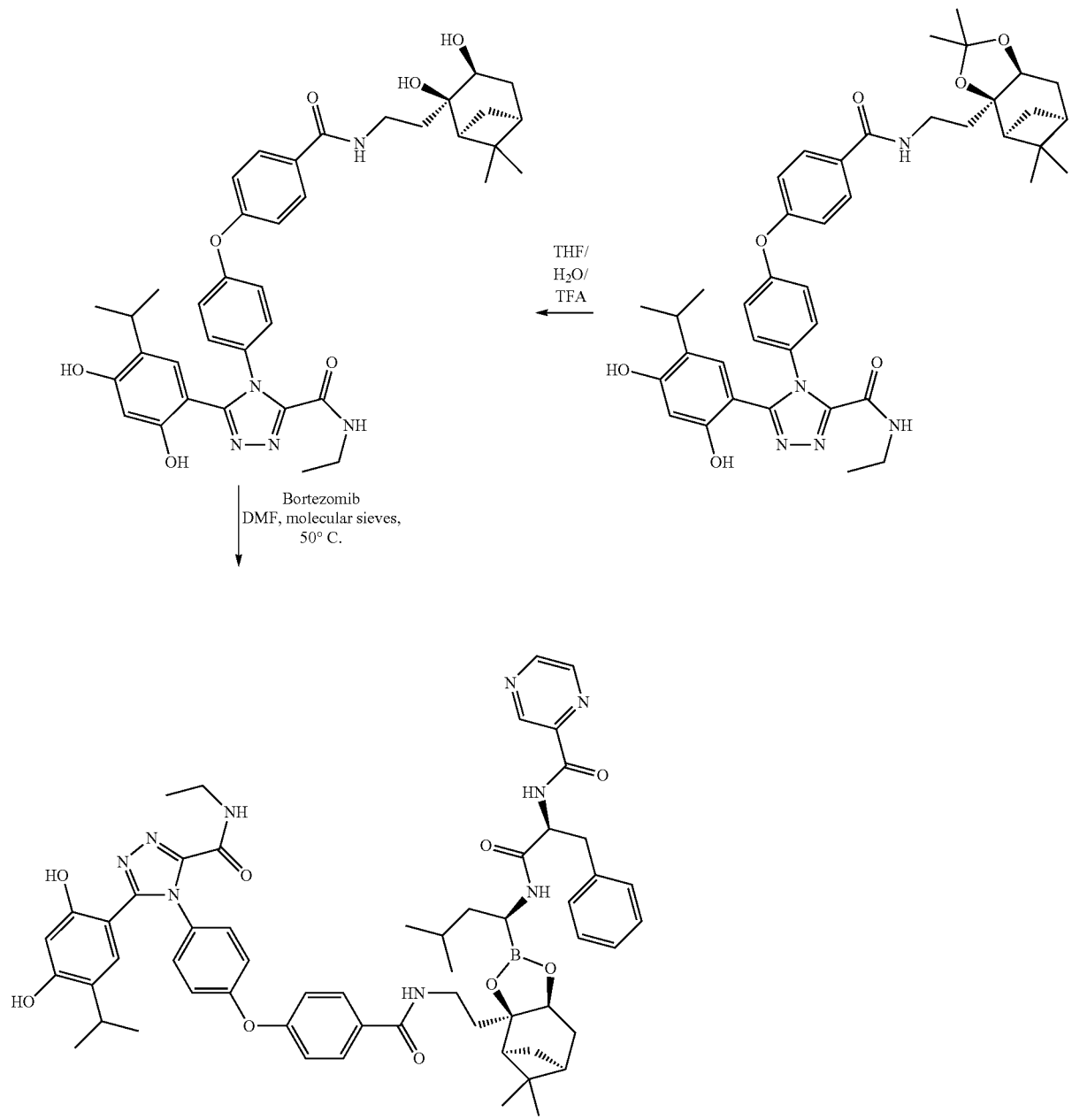

2-((3aR,4S,6S,7aS)-2,2,5,5-tetramethylhexahydro-4,6-methanobenzo[d][1,3]dioxol-3a-yl)ethanol (0.88 mmol) was dissolved in THF (5.5 mL), and cooled to 0° C. To the cooled solution was added triphenylphosphine (2.64 mmol), diisopropyl azodicarboxylate (2.64 mmol) and diphenylphosphoryl azide (2.64 mmol), followed by stirring at the same temperature for 3.5 h. The mixture was diluted with saturated aqueous NaHCO$_3$ (20 mL), and warmed to room temperature. The mixture was extracted with EtOAc (10 m×2). The combined organic layer was dried over residue was subjected to silica gel chromatography purification (EtOAc/Hexanes) to yield (3aR,4S,6S,7aS)-3a-(2-azidoethyl)-2,2,5,5-tetramethylhexahydro-4,6-methanobenzo[d][1,3]dioxole.

A round-bottomed flask was charged with (3aR,4S,6S,7aS)-3a-(2-azidoethyl)-2,2,5,5-tetramethylhexahydro-4,6-methanobenzo[d][1,3]dioxole (0.60 mmol), MeOH (1 mL) and palladium on carbon (10 wt. % loading, 0.03 mmol). The flask was flushed with hydrogen and kept under hydrogen atmosphere. After stirring for 13.5 h, the reaction mixture was filtered through a filter paper, and the filtrate was concentrated under reduced pressure to yield 2-((3aR, 4S,6S,7aS)-2,2,5,5-tetramethylhexahydro-4,6-methanobenzo[d][1,3]dioxol-3a-yl)ethanamine.

4-(4-(3-(2,4-dihydroxy-5-isopropylphenyl)-5-(ethylcarbamoyl)-4H-1,2,4-triazol-4-yl)phenoxy)benzoic acid (0.10 mmol) was dissolved in DMF, followed by the addition of 2-((3aR,4S,6S,7aS)-2,2,5,5-tetramethylhexahydro-4,6-methanobenzo[d][1,3]dioxol-3a-yl)ethanamine (0.60 mmol), HATU (0.50 mmol) and diisopropyl ethylamine (0.30 mmol). The solution was stirred at 23° C. for 4 h. The solution was concentrated under reduced pressure, and the resulting residue was purified by silica gel chromatography (CH$_2$Cl$_2$/MeOH) to afford 5-(2,4-dihydroxy-5-isopropylphenyl)-N-ethyl-4-(4-(4-((2-((3aR,4S,6S,7aS)-2,2,5,5-tetramethylhexahydro-4,6-methanobenzo[d][1,3]dioxol-3a-yl)ethyl)carbamoyl)phenoxy)phenyl)-4H-1,2,4-triazole-3-carboxamide.

5-(2,4-dihydroxy-5-isopropylphenyl)-N-ethyl-4-(4-(4-((2-((3aR,4S,6S,7aS)-2,2,5,5-tetramethylhexahydro-4,6-methanobenzo[d][1,3]dioxol-3a-yl)ethyl)carbamoyl)phenoxy)phenyl)-4H-1,2,4-triazole-3-carboxamide (0.06 mmol) was dissolved in a solution of THF/H$_2$O/TFA (1:1:1 v/v/v; 2 mL) and stirred in a 60° C. oil bath for 2 h, then concentrated under reduced pressure. The crude mixture was subjected to silica gel chromatography purification (CH$_2$Cl$_2$/MeOH) to yield 5-(2,4-dihydroxy-5-isopropylphenyl)-4-(4-(4-((2-((1S,2R,3S,5S)-2,3-dihydroxy-6,6-dimethylbicyclo[3.1.1]heptan-2-yl)ethyl)carbamoyl)phenoxy)phenyl)-N-ethyl-4H-1,2,4-triazole-3-carboxamide.

A round-bottomed flask was charged 5-(2,4-dihydroxy-5-isopropylphenyl)-4-(4-(4-((2-((1 S,2R,3S,5S)-2,3-dihydroxy-6,6-dimethylbicyclo[3.1.1]heptan-2-yl)ethyl)carbamoyl)phenoxy)phenyl)-N-ethyl-4H-1,2,4-triazole-3-carboxamide (0.04 mmol), Bortezomib (0.05 mmol), DMF (1 mL) and 4 Å molecular sieves (123 mg). The mixture was stirred in a 50° C. oil bath for 12 h, then the solvent was removed under reduced pressure. The resulting residue was purified by silica gel chromatography (CH$_2$Cl$_2$ containing 2% Et$_3$N/MeOH) followed by reverse-phase C18 chromatography (H$_2$O/MeCN), followed by lyophilizing the desired fractions to yield SDC-TRAP-0248 as a white solid.

$^1$H NMR (400 MHz, CD$_3$CN), δ 9.07 (d, J=1.6 Hz, 1H), 8.65 (d, J=2.4 Hz, 1H), 8.42 (ddd, J=1.6, 1.6, 1.6 Hz, 1H), 8.14 (d, J=8.4 Hz, 1H), 7.75 (d, J=8.8 Hz, 2H), 7.64-7.59 (m, 2H), 7.55-7.52 (m, 2H), 7.33-7.29 (m, 2H), 7.21-7.10 (m, 4H), 7.07-7.00 (m, 4H), 6.47 (s, 1H), 6.35 (s, 1H), 4.80-4.75 (m, 2H), 4.25 (dd, J=8.8, 1.6 Hz, 1H), 3.88 (d, J=5.6 Hz, 1H), 3.44-3.40 (m, 2H), 3.21 (ddd, J=13.6, 7.2, 7.2 Hz, 2H), 3.05 (ddd, J=13.6, 6.0, 6.0 Hz, 2H), 2.88-2.81 (m, 2H), 1.81-1.21 (m, 11H), 1.05 (t, J=7.2 Hz, 3H), 0.89 (d, J=6.8 Hz, 6H), 0.85 (s, 3H), 0.84 (s, 3H), 0.74 (d, J=6.8 Hz, 6H); ESMS calcd for C$_{57}$H$_{66}$BN$_9$O$_9$: 1031.5. found: 1032.2 (M+H$^+$).

SDC-TRAP-0249

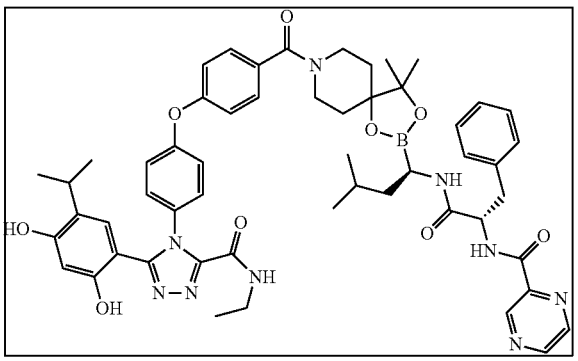

The compound 4-(2-hydroxypropan-2-yl)piperidin-4-ol hydrochloride was prepared according to the scheme and procedure below.

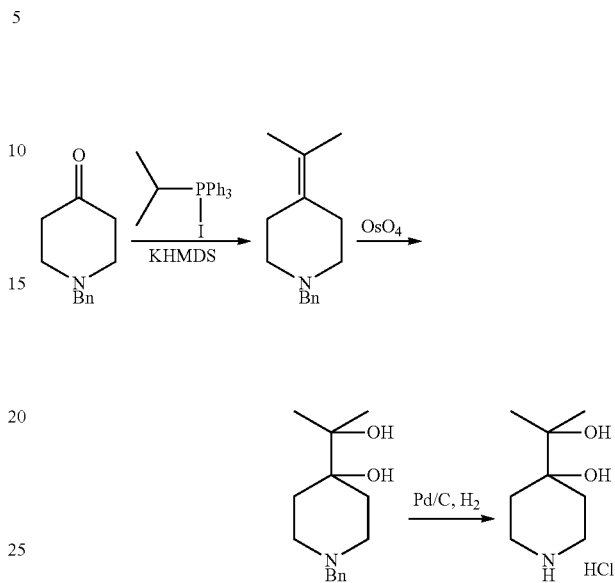

To a solution of iodo(isopropyl)triphenylphosphorane (90 g, 208 mmol) in toluene (400 mL) was added KHMDS (192 mL, 208 mmol) at room temperature. The mixture was stirred at room temperature for 10 min. A solution of 1-benzylpiperidin-4-one (20 g, 104 mmol) in toluene (250 mL) was added. The mixture was refluxed for 2 h, then cooled to room temperature and diluted with EtOAc (250 mL). The mixture was washed with H$_2$O (100 mL), dried and concentrated under reduced pressure. The residue was purified by SGC to yield 1-benzyl-4-(propan-2-ylidene)piperidine.

A solution of NMO (8.3 g, 96.8 mmol) in acetone (120 mL) and water (10 mL) was added OsO$_4$ (94.5 mg, 0.37 mmol) under N$_2$ atmosphere, then 1-benzyl-4-(propan-2-ylidene)piperidine (8 g, 37.2 mmol) was added. The mixture was refluxed overnight, then acetone was removed under reduced pressure. The resulting mixture was extracted with EtOAc (×3), dried and concentrated under reduced pressure. The residue was purified by SGC to yield 1-benzyl-4-(2-hydroxypropan-2-yl)piperidin-4-ol.

To a solution of 1-benzyl-4-(2-hydroxypropan-2-yl)piperidin-4-ol (3.85 g, 16 mmol) in MeOH (65 mL) was added 10% Pd/C (0.8 g). The mixture was stirred at room temperature under H$_2$ at 1 Mpa overnight concentrated HCl (1.5 mL) was added. The mixture was stirred at 2 Mpa overnight. Additional 10% Pd/C (0.3 g) and concentrated HCl (2 mL) were added. The mixture was stirred at 4 Mpa overnight, then filtered. The filtrate was concentrated under reduced pressure to yield 4-(2-hydroxypropan-2-yl)piperidin-4-ol hydrochloride.

N—((S)-1-(((R)-1-(8-(4-(4-(3-(2,4-dihydroxy-5-isopropylphenyl)-5-(ethylcarbamoyl)-4H-1,2,4-triazol-4-yl)phenoxy)benzoyl)-4,4-dimethyl-1,3-dioxa-8-aza-2-boraspiro[4.5]decan-2-yl)-3-methylbutyl)amino)-1-oxo-3-phenylpropan-2-yl)pyrazine-2-carboxamide

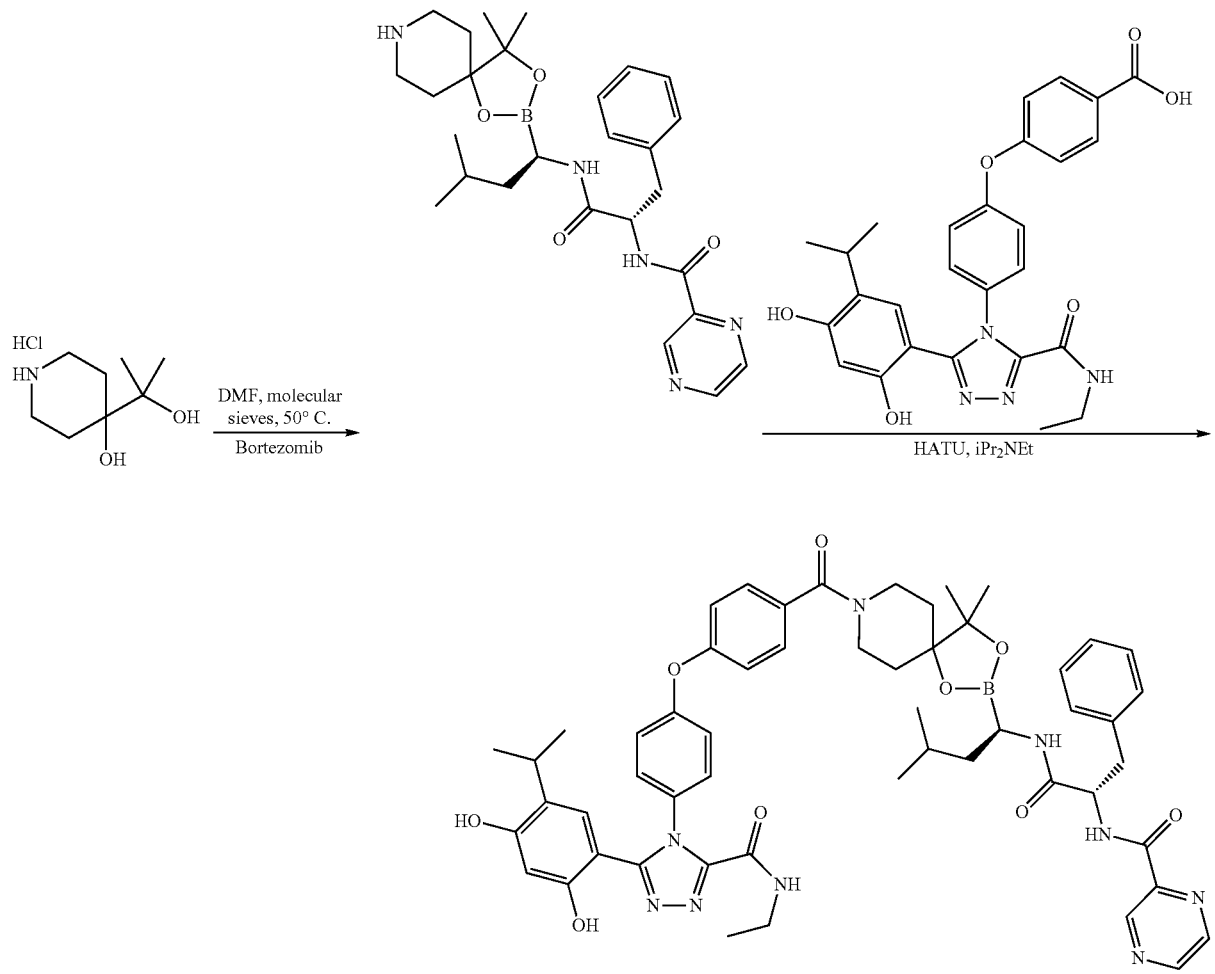

A round-bottomed flask was charged 4-(2-hydroxypropan-2-yl)piperidin-4-ol hydrochloride (0.30 mmol), Bortezomib (0.35 mmol), DMF (1 mL) and 4 Å molecular sieves (110 mg). The mixture was stirred in a 50° C. oil bath for 3 h, then added 4-(4-(3-(2,4-dihydroxy-5-isopropylphenyl)-5-(ethylcarbamoyl)-4H-1,2,4-triazol-4-yl)phenoxy)benzoic acid (0.30 mmol), HATU (0.45 mmol) and diisopropyl ethylamine (0.90 mmol). The solution was stirred at 23° C. for 2 h, then concentrated under reduced pressure. The resulting residue was subjected to silica gel chromatography purification (CH$_2$Cl$_2$/MeOH) to afford SDC-TRAP-0249 as a white solid.

$^1$H NMR (400 MHz, CDCl$_3$), δ 11.6 (s, 1H), 9.33 (s, 1H), 8.75 (s, 1H), 8.58-8.47 (m, 1H), 8.33 (s, 1H), 7.45 (d, J=8.8 Hz, 2H), 7.41-7.35 (m, 2H), 7.30-7.23 (m, 6H), 7.13-7.10 (m, 4H), 6.51 (s, 1H), 6.43 (s, 1H), 4.92-4.87 (m, 1H), 4.73-4.61 (m, 1H), 3.77-3.68 (m, 1H), 3.41 (ddd, J=13.6, 7.2, 7.2 Hz, 2H), 3.20 (ddd, J=13.6, 6.4, 6.4 Hz, 2H), 2.97 (dq, J=13.6, 6.8 Hz, 1H), 2.87-2.78 (m, 1H), 1.95-1.52 (m, 10H), 1.25 (s, 3H), 1.24 (t, J=7.2 Hz, 3H), 1.22 (s, 3H), 0.84 (d, J=6.8 Hz, 6H), 0.80 (d, J=6.0 Hz, 6H); ESMS calcd for C$_{54}$H$_{62}$BN$_9$O$_9$: 991.5. found: 992.1 (M+H$^+$).

SDC-TRAP-0250

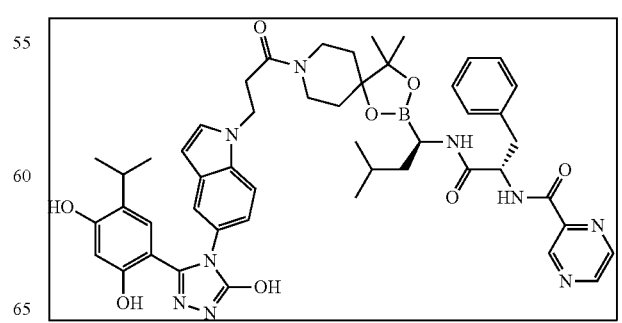

N—((S)-1-(((R)-1-(8-(3-(5-(3-(2,4-dihydroxy-5-isopropylphenyl)-5-hydroxy-4H-1,2,4-triazol-4-yl)-1H-indol-1-yl)propanoyl)-4,4-dimethyl-1,3-dioxa-8-aza-2-boraspiro[4.5]decan-2-yl)-3-methylbutyl)amino)-1-oxo-3-phenylpropan-2-yl)pyrazine-2-carboxamide N—((S)-1-(((R)-1-(8-(4-(3-(2,4-dihydroxy-5-isopropylphenyl)-5-(ethylcarbamoyl)-4H-1,2,4-triazol-4-yl)benzoyl)-4,4-dimethyl-1,3-dioxa-8-aza-2-boraspiro[4.5]decan-2-yl)-3-methylbutyl)amino)-1-oxo-3-phenylpropan-2-yl)pyrazine-2-carboxamide

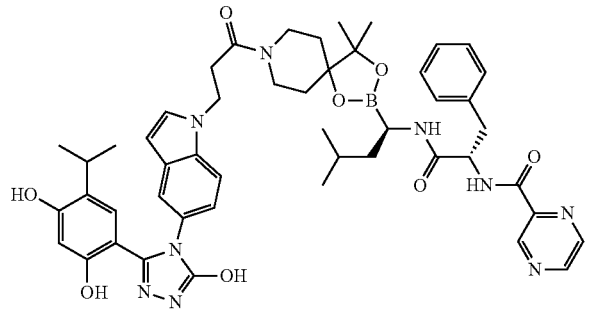 [SMILES: CC(C)C[C@H](NC(=O)[C@H](Cc1ccccc1)NC(=O)c1cnccn1)B1OC(C)(C)C2(CCN(C(=O)CCn3ccc4cc(-n5c(O)nnc5-c5cc(C(C)C)c(O)cc5O)ccc43)CC2)O1]

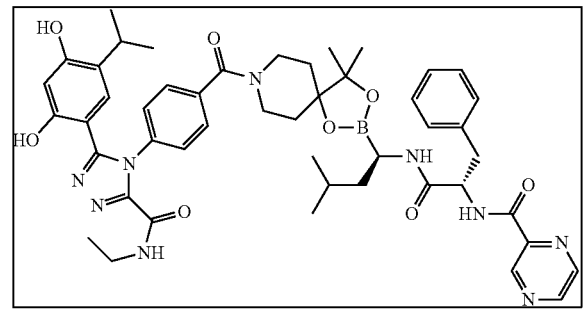

Preparation of SDC-TRAP-0250 followed a similar procedure as for SDC-TRAP-0249, starting from 3-(5-(3-(2,4-dihydroxy-5-isopropylphenyl)-5-hydroxy-4H-1,2,4-triazol-4-yl)-1H-indol-1-yl)propanoic acid instead of 4-(4-(3-(2,4-dihydroxy-5-isopropylphenyl)-5-(ethylcarbamoyl)-4H-1,2,4-triazol-4-yl)phenoxy)benzoic acid.

ESMS calcd for $C_{49}H_{58}BN_9O_8$: 911.5. found: 912.1 (M+H$^+$).

SDC-TRAP-0251

Preparation of SDC-TRAP-0251 followed a similar procedure as for SDC-TRAP-0249, starting from 4-(3-(2,4-dihydroxy-5-isopropylphenyl)-5-(ethylcarbamoyl)-4H-1,2,4-triazol-4-yl)benzoic acid instead of 4-(4-(3-(2,4-dihydroxy-5-isopropylphenyl)-5-(ethylcarbamoyl)-4H-1,2,4-triazol-4-yl)phenoxy)benzoic acid.

ESMS calcd for $C_{48}H_{58}BN_9O_8$: 899.5. found: 900.0 (M+H$^+$).

SDC-TRAP-0252

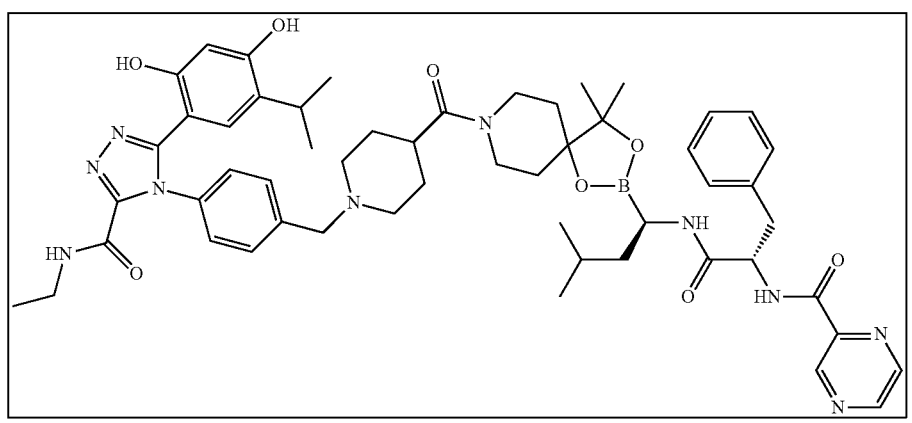

N—((S)-1-(((R)-1-(8-(1-(4-(3-(2,4-dihydroxy-5-isopropylphenyl)-5-(ethylcarbamoyl)-4H-1,2,4-triazol-4-yl)benzyl)piperidine-4-carbonyl)-4,4-dimethyl-1,3-dioxa-8-aza-2-boraspiro[4.5]decan-2-yl)-3-methylbutyl)amino)-1-oxo-3-phenylpropan-2-yl)pyrazine-2-carboxamide

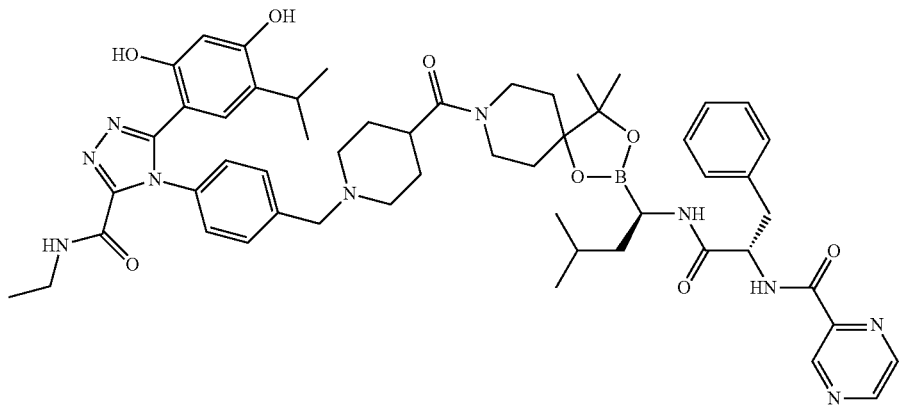 [SMILES: CCNC(=O)c1nnc(-c2cc(C(C)C)c(O)cc2O)n1-c1ccc(CN2CCC(C(=O)N3CCC4(CC3)OB([C@H](CC(C)C)NC(=O)[C@H](Cc3ccccc3)NC(=O)c3cnccn3)OC4(C)C)CC2)cc1]

Preparation of SDC-TRAP-0252 followed a similar procedure as for SDC-TRAP-0249, starting from 1-(4-(3-(2,4-dihydroxy-5-isopropylphenyl)-5-(ethylcarbamoyl)-4H-1,2,4-triazol-4-yl)benzyl)piperidine-4-carboxylic acid instead of 4-(4-(3-(2,4-dihydroxy-5-isopropylphenyl)-5-(ethylcarbamoyl)-4H-1,2,4-triazol-4-yl)phenoxy)benzoic acid.

ESMS calcd for $C_{54}H_{69}BN_{10}O_8$: 996.5. found: 997.0 (M+H$^+$).

The conjugate synthesis schemes are exemplary. Other synthetic methods, linkers, and binding moieties can be linked to the above effector molecules.

Example 3—The Design of Other HSP90-Inhibitor Proteasome-Inhibitor Conjugates: Ixazomib Ixazomib is a proteasome inhibitor that is being developed for various indications. The drug is in Phase III trials and chemically it is a boronate ester of citric acid, which readily gets cleaved in the systemic circulation. Therefore, the reasonable way to make an SDC-TRAP of ixazomib is with the active component where the boronic acid can be stabilized to withstand rapid metabolism in plasma by making esters of sterically hindered diols. The following are representative designs:

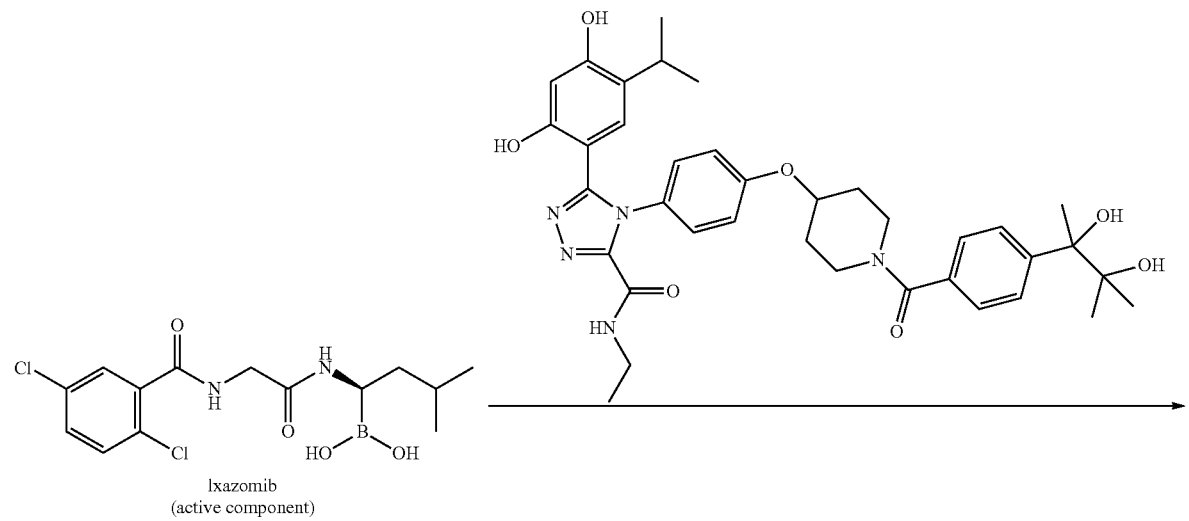

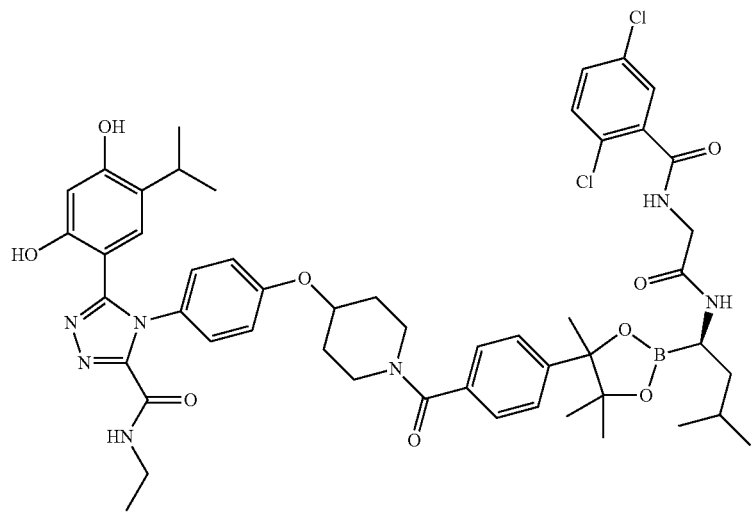
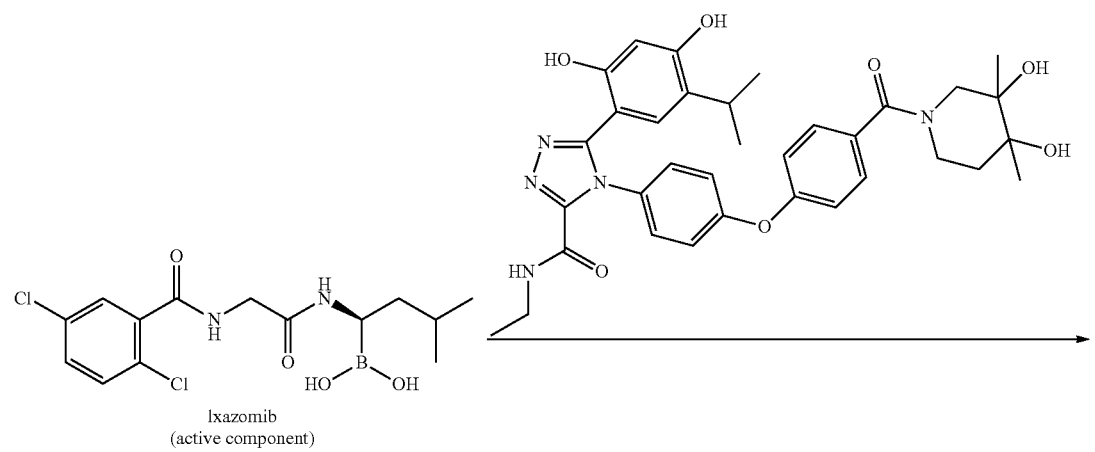
Ixazomib
(active component)
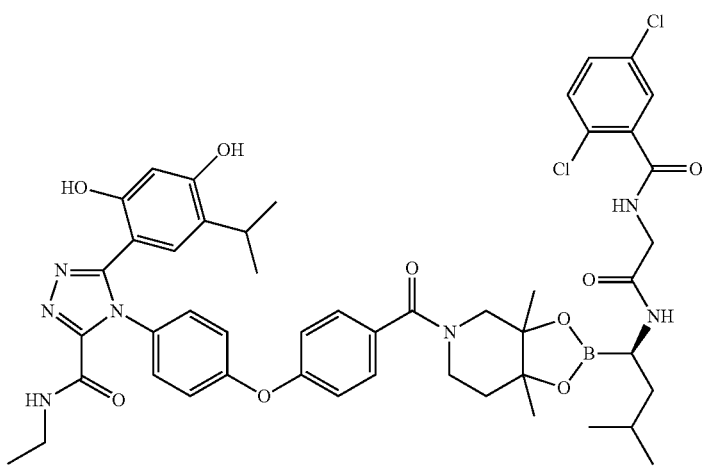

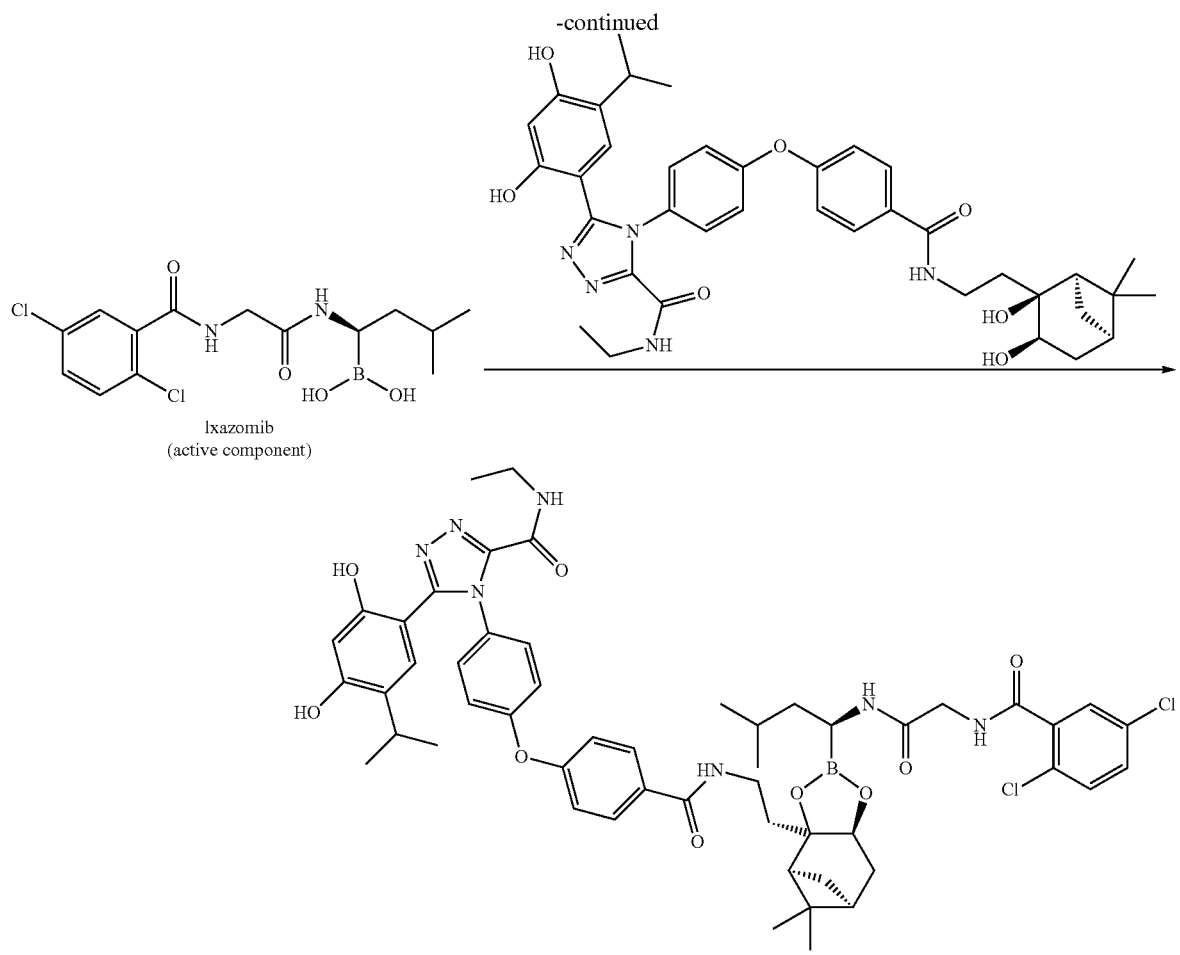

Ixazomib
(active component)

Example 4—The Design of Other HSP90-Inhibitor Proteasome-Inhibitor Conjugates: Delanzomib Delanzomib is a boronic acid analog of Velcade that showed similar or better in vitro activity compared to Velcade in terms of proteasome inhibition in human cells and cytotoxicity for tumor cells. It is a potent, selective and orally active second-generation proteasome inhibitor. It is currently at phase II clinical trial for treatment of Multiple myeloma. Additional early clinical studies had been under way at Ethical Oncology Science (EOS), licensee of the compound, for the treatment of solid tumors and non-Hodgkin's lymphoma (NHL). Unlike Velcade, Delanzomib has a hydroxyl "handle" that can conjugate to our Hsp90i through a carbamate or ester linker. Below are representative designs:

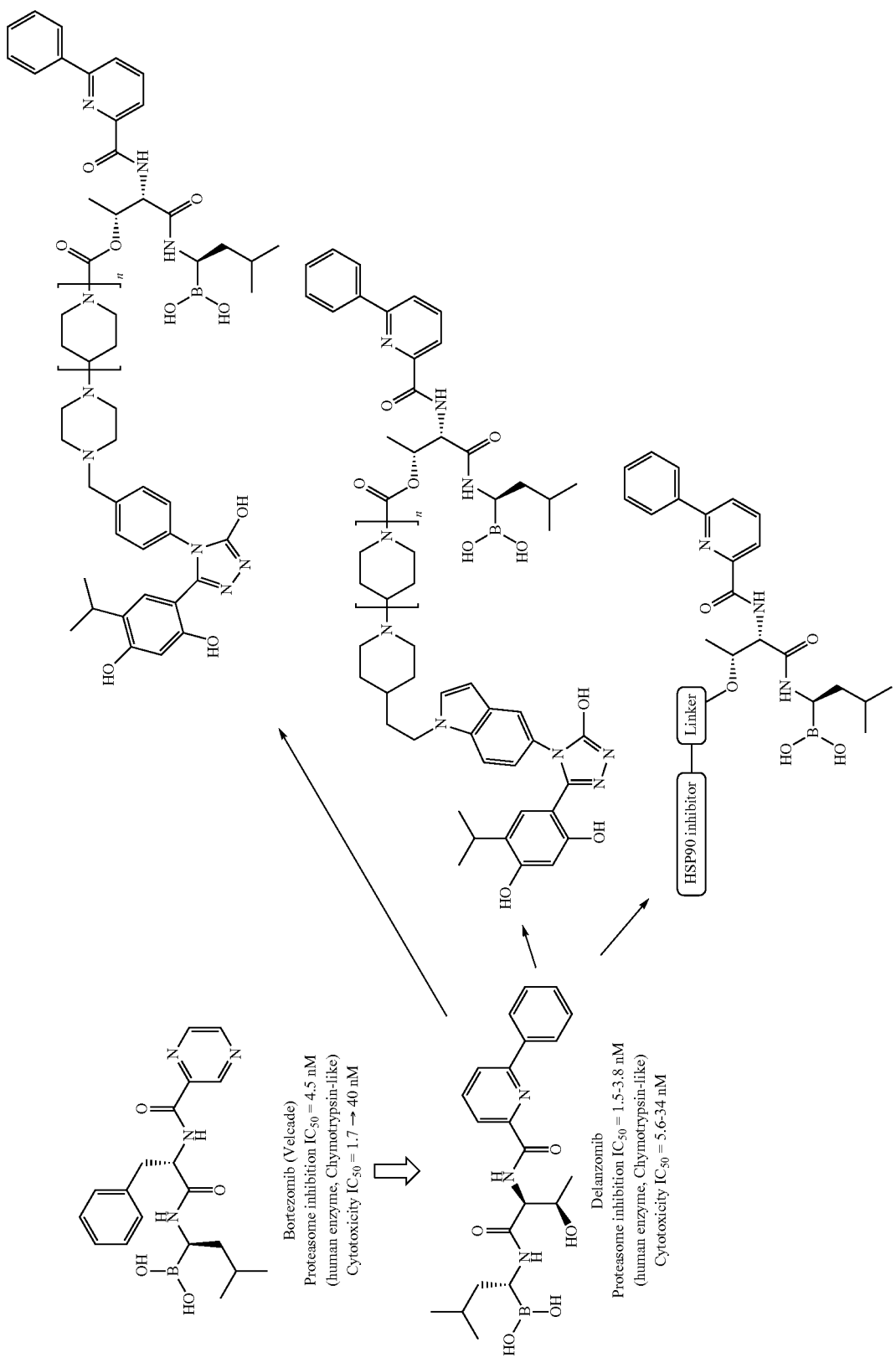

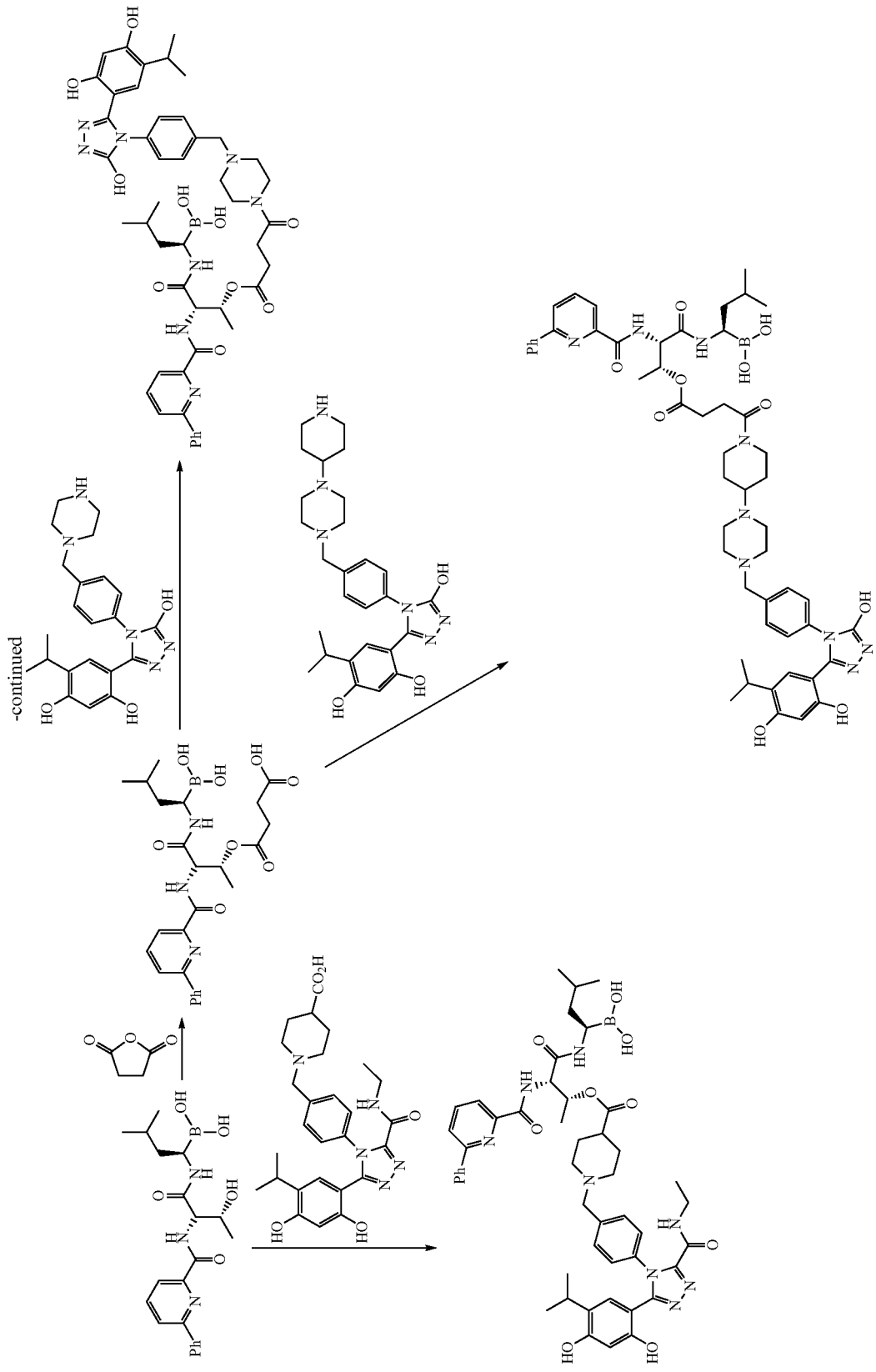

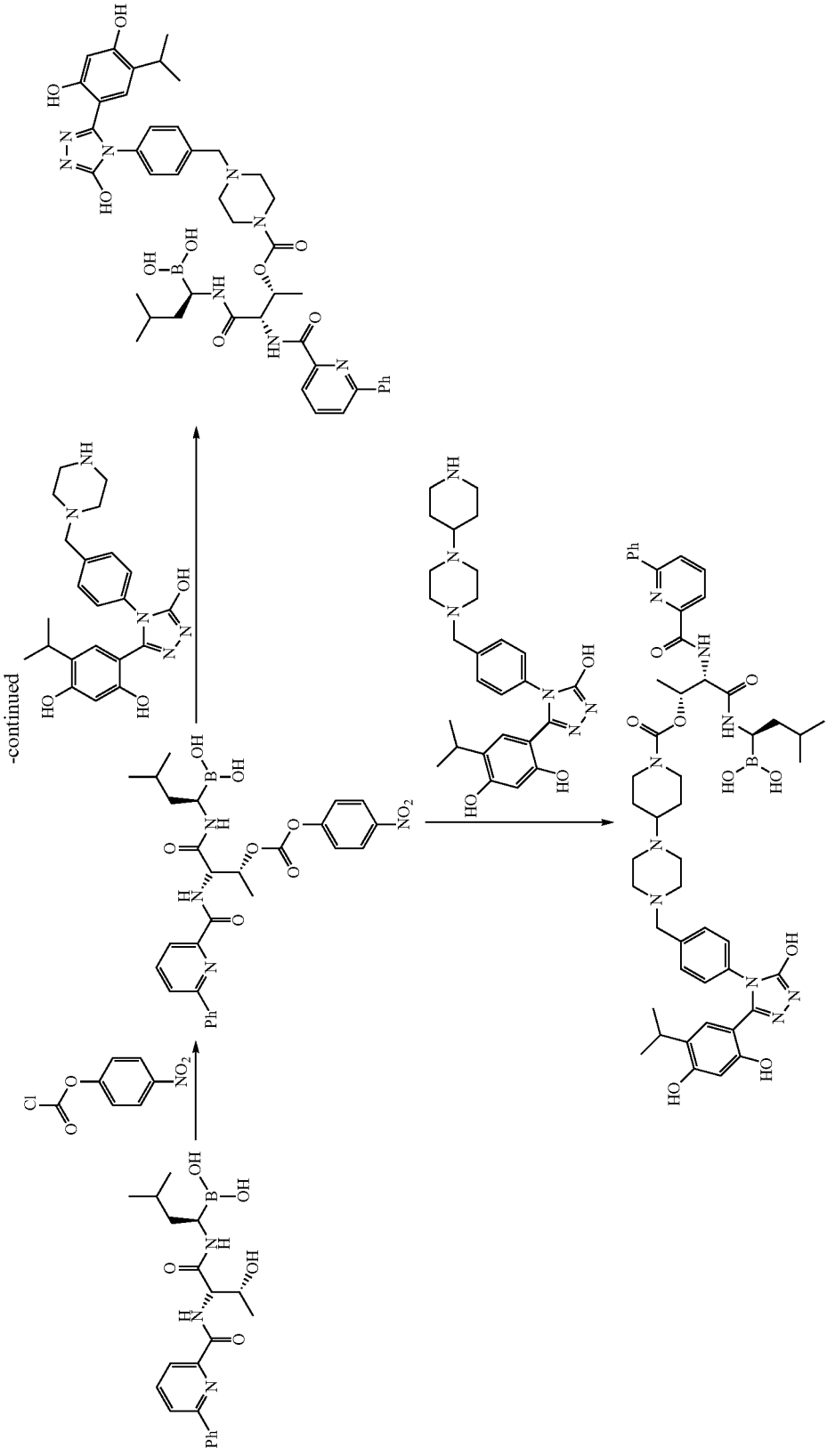

An alternate design of HSP90-inhibitor bortezomib conjugates is through an introduction of a handle (alcohol or amine functional group) moiety to serve as a conjugation site of the HSP90 inhibitor portion. In this case, the drug is no more bortezomib, but an analogue. The alcohol or amine functional group will be introduced either at the end of the molecule (modifying the pyrazine unit) or incorporating a tyrosine unit instead of a phenylalanine in bortezomib. The sites were chosen based on available SAR data, which indicate that such a modification should not interfere with the proteasomal inhibition activity upon release of the payload. The following are representative designs:

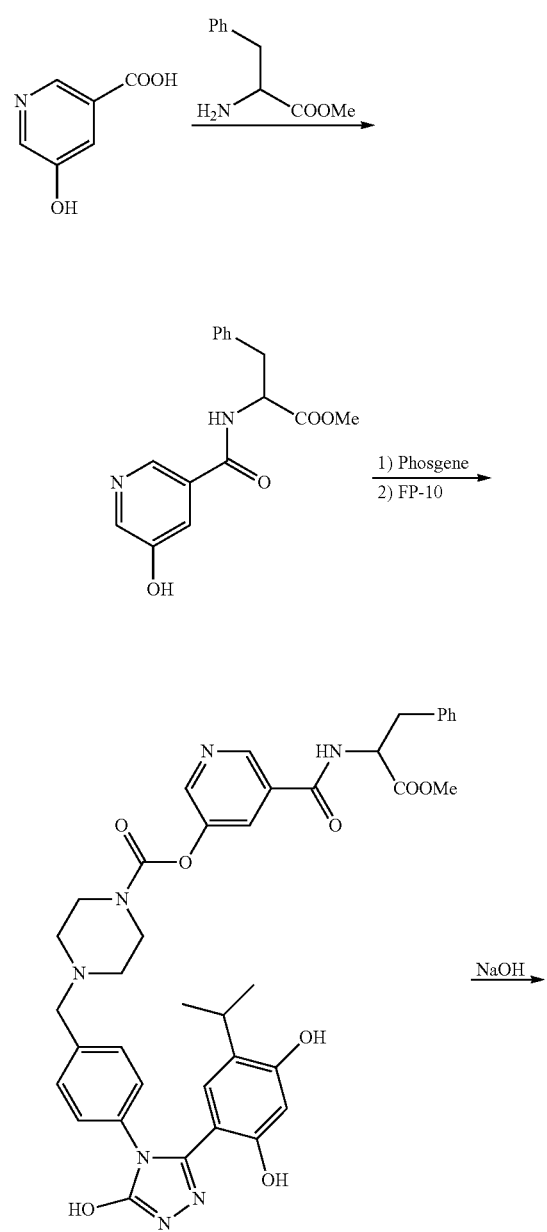

-continued

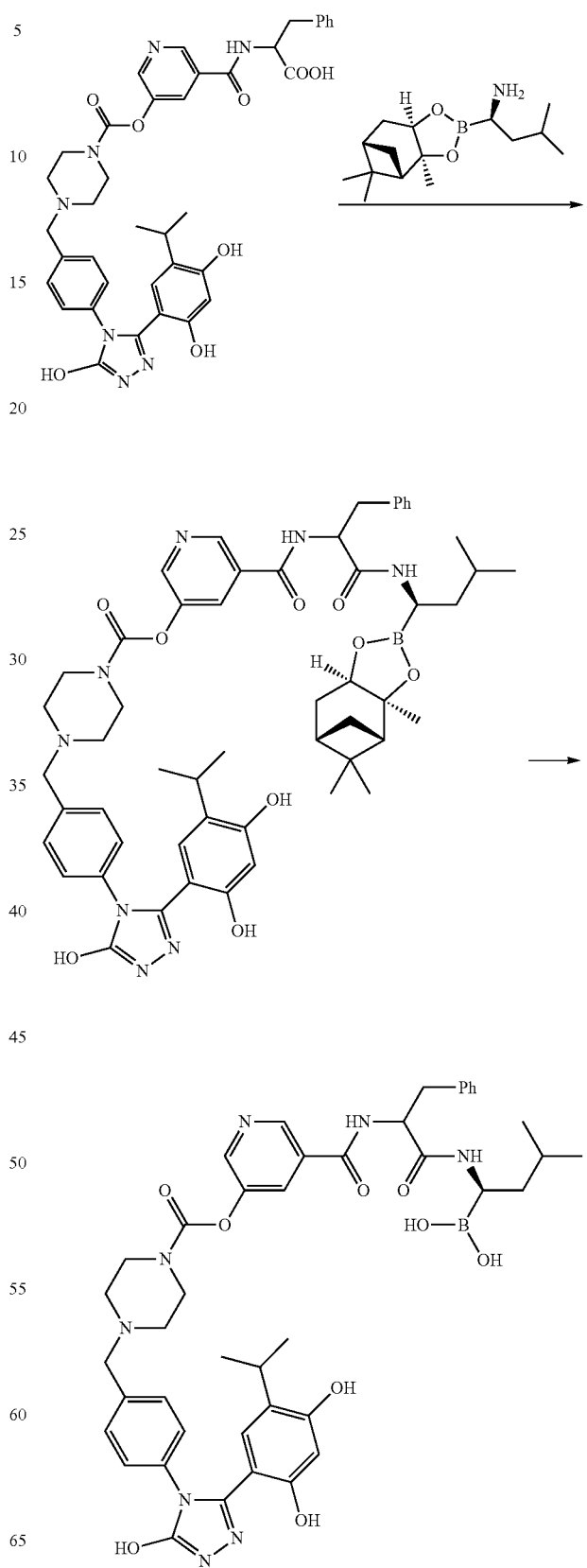

-continued

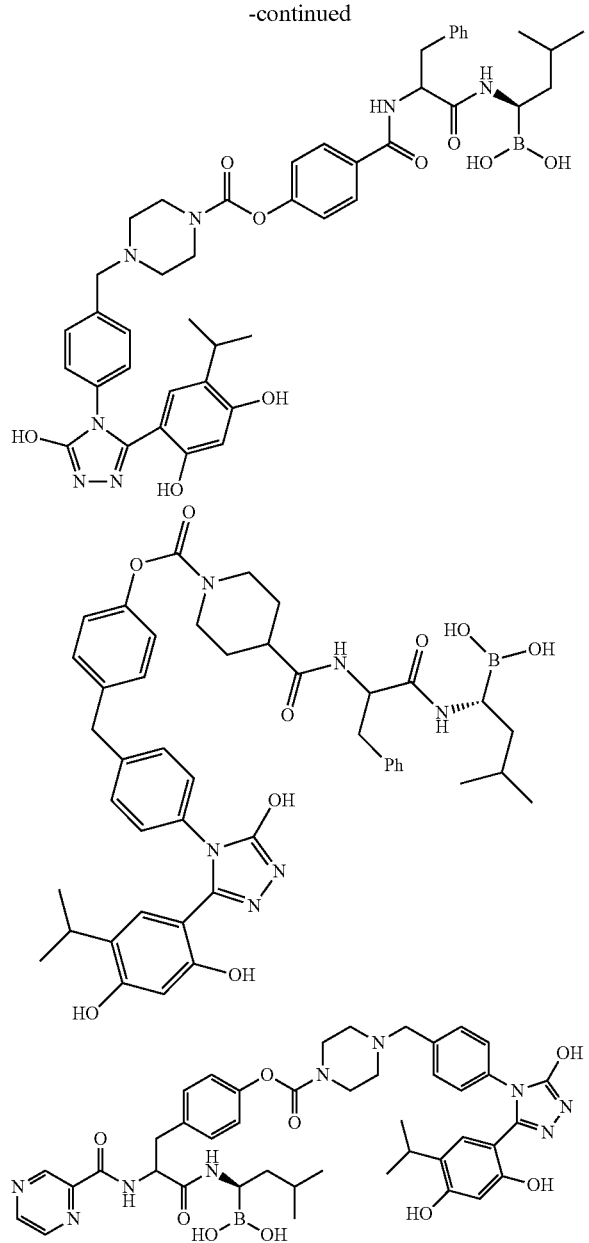

Example 5—Assessing Stability of SDC-TRAPs in Mouse Plasma

SDC-TRAPs were incubated in mouse plasma for 1 h at 37° C. and assayed for integrity at 0, 0.25, 0.5 and 1 h to assess the stability of the SDC-TRAP, e.g., as compared to the effector and targeting compounds. Compound stability was determined using a flow cytometer (FACS) machine.

Stability data of the HSP90-inhibitor bortezomib conjugates in mouse plasma.

The data collected at one hour are presented in the table below.

| Compound ID | % Remaining (1 h) |
|---|---|
| SDC-TRAP-0248 | 54.8 |
| SDC-TRAP-0244 | 62.9 |

-continued

| Compound ID | % Remaining (1 h) |
|---|---|
| SDC-TRAP-0237 | 84.2 |
| SDC-TRAP-0236 | 25.5 |
| SDC-TRAP-0246 | 63.6 |
| SDC-TRAP-0238 | 24.0 |
| SDC-TRAP-0239 | 35.8 |
| SDC-TRAP-0249 | 8.93 |
| SDC-TRAP-0250 | 27.0 |
| SDC-TRAP-0247 | 11.8 |
| SDC-TRAP-0251 | 13.4 |
| SDC-TRAP-0252 | 34 |
| SDC-TRAP-0240 | 84.0 |
| SDC-TRAP-0245 | 44.2 |
| SDC-TRAP-0242 | Not determined |
| SDC-TRAP-0243 | Not determined |
| SDC-TRAP-0241 | Not determined |

Figure 3:
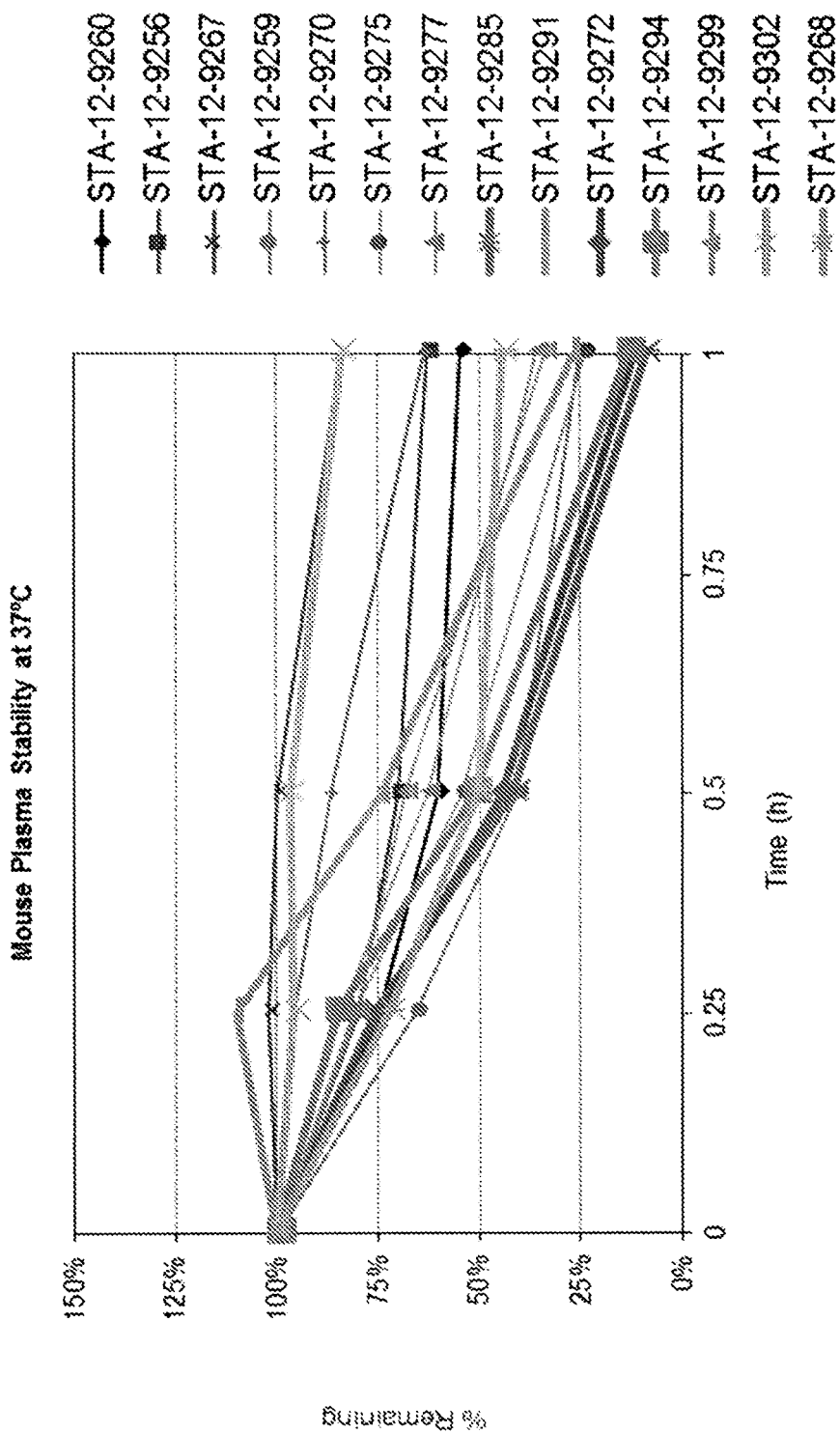
FIG. 3 shows stability of SDC-TRAPs in mouse plasma.

Data taken at times 0, 15 minutes, 30 minutes and 1 hour are presented in FIG. 3.

Example 6—HER2 Degradation Assay with BT-474 Cell Line

This example illustrates how a HER2 degradation assay may be used as a test to determine and select Hsp90-targeting moieties suitable for use in SDC-TRAPs of the invention, and further illustrates the ability of SDC-TRAPs to target cells preferentially expressing Hsp90. Such a test may further be used to determine the Hsp90 binding ability of SDC-TRAPs of the invention, as well as through competitive binding assays and cell-based Hsp90 client protein degradation assays known in the art.

Degradation of HER2 in Cells after Treatment with an SDC-TRAP of the invention.

HER2 has emerged as a key target for anticancer drugs due to its intrinsic involvement in the phosphatidylinositol-3-kinase-Akt/protein kinase B (PI3 K-Akt) and the mitogen-activated protein kinase (MAPK) pathways, both of which suppress apoptosis and promote tumor cell survival, gene transcription, angiogenesis, cellular proliferation, migration, mitosis, and differentiation. The degradation of HER2 is a measure of efficacy of anticancer therapeutics that target Hsp90. Accordingly, the SDC-TRAP molecules of the invention that comprise a binding moiety that binds Hsp90 were tested in the following HER2 degradation assay.

BT-474 cells (human breast cancer cell line ATCC HTB-20) were obtained from ATCC and seeded into 12-well tissue culture plates at $0.2 \times 10^6 / 1.8$ mL/well. The cells were incubated for more than 6 hours at 37° C. in DMEM+10% FBS, +1% P/S, +1.5 g/L sodium bicarbonate. Each test compound was titrated in 4-fold dilutions from 5 µM to 78 nM with DMSO and 200 µL of the titration was added to each well of the cell plate. The DMSO final concentration was 0.2%. Cells were incubated overnight at 37° C. in 5% $CO_2$.

Media was decanted from the plate, cells were washed 1× in PBS. 400 µL trypsin (EDTA) per well was added, and the cells were incubated for 2 to 3 minutes. Cells were collected into FACS tubes containing 1 ml culture medium to neutralize the trypsin and were centrifuged for 5 minutes at 1200 rpm. Supernatant was decanted and the cells were resuspended in 5 µL FITC (anti HER2/nu)/200 µL staining buffer (1×PBS+1% FBS+0.05% Sodium Azide)/tube. Controls were 5 µL IgG isotype control and staining buffer only. Tubes were incubated for 30 minutes in the dark at room temperature. 1 mL staining buffer was added to each tube and the tubes were centrifuged for 6 minutes at 1200 rpm.

The supernatant was decanted and 300 μL staining buffer was added to each tube, which was stored at 4° C. for FACS (cytometer) analysis. The cytometer readout was normalized and the potency of each compound was evaluated with $IC_{50}$ calculated with XLfit™ software.

Her2 degradation assay activity data for the HSP90-inhibitor bortezomib conjugates.

| Compound ID | Her2 degradation assay activity ($IC_{50}$, nM) |
| --- | --- |
| SDC-TRAP-0248 | 37 |
| SDC-TRAP-0244 | 100 |
| SDC-TRAP-0237 | >5000 |
| SDC-TRAP-0236 | 710 |
| SDC-TRAP-0246 | 110 |
| SDC-TRAP-0238 | >5000 |
| SDC-TRAP-0239 | >5000 |
| SDC-TRAP-0249 | 36 |
| SDC-TRAP-0250 | 2118 |
| SDC-TRAP-0247 | 36 |
| SDC-TRAP-0251 | >5000 |
| SDC-TRAP-0252 | Not determined |
| SDC-TRAP-0240 | >5000 |
| SDC-TRAP-0245 | 106, 128 |
| SDC-TRAP-0242 | 407 |
| SDC-TRAP-0243 | Not determined |
| SDC-TRAP-0241 | Not determined |

Example 7—Tissue Distribution and Metabolism of an Exemplary Hsp90 Binding Moiety The ability of Hsp90-targeting moieties to penetrate solid tumors and exhibit rapid clearance from normal tissues for reduced toxicity is illustrated in the following tissue distribution study with a compound, ganetespib, which may be used as an Hsp90 binding moiety.

Tissue distribution of ganetespib in female CD-1 nu/nu mice bearing RERF human NSCLC xenografts
Objectives:
To confirm the distribution of ganetespib in blood, livers, kidneys, brains, hearts, lungs and tumors after IV administration of ganetespib to female CD-1 nu/nu mice bearing RERF human NSCLC xenografts, and to examine metabolic profiles of ganetespib in plasma, red blood cells, and above tissues.
Study Outline:
Test Articles: ganetespib
Animals: female CD-1 nu/nu mice bearing RERF human NSCLC xenografts (N=3/group)
Route: IV
Dosage: 50 mg/kg
Dose level: 10 mL/kg
Formulation: 10% DMSO, 18% Cremophor RH40, 3.6% dextrose solution (DRD)
Bleeding time points: 5 min, 6, 24 hr
Collected tissues: blood (plasma and red blood cells (RBC)), liver, kidneys, brain, heart, lung, tumor
Method
Sample Preparation
Plasma and RBC
Protein precipitation: 50 μL of 10 times diluted plasma or RBC+150 μL ACN (10 mM $NH_4OAc$), vortexed and centrifuged at 10000 rpm for 8 min; 150 μL supernatant+150 μL water (10 mM $NH_4OAc$)
Other Tissues
Protein precipitation: 100 μL homogenized tissue (1:3 tissue: PBS buffer)+100 μL ACN (10 mM $NH_4OAc$), vortexed and centrifuged at 10000 rpm for 8 min Bioanalysis
HPLC (ChemStation)
Column: Agilent Zorbax Eclipse XDB-C18, 4.6×150 mm, 5 μm
Mobile phase: A: water containing 10 mM $NH_4OAc$; B: 95% ACN containing 10 mM $NH_4OAc$
Gradient: 95/5 A/B to 5/95 A/B in 10 min, total run time 15 min
Flow rate: 1 mL/min
Column temp.: 40° C.
Wavelength: 254 nm
Injection volume: 100 μL
Calibration curve range:
Plasma: 1-50 μM (linear regression; $R^2$=0.9901); LLOQ=1 μM
RBC: 1-50 μM (linear regression; $R^2$=0.9987); LLOQ=1 μM
Kidney: 1-100 μM (linear regression; $R^2$=1.0000); LLOQ=1 μM
Lung: 1-100 μM (linear regression; $R^2$=1.0000); LLOQ=1 μM
Heart: 1-100 μM (linear regression; $R^2$=0.9998); LLOQ=1 μM
Liver: 1-100 μM (linear regression; $R^2$=1.0000); LLOQ=1 μM
Tumor: 0.1-10 μM (linear regression; $R^2$=1.0000); LLOQ=0.1 μM
LC-MS/MS (Q-Trap4000)
Polarity: positive (ESI)
Column: Phenomenex Synergi, 2.1×50 mm, 4 μm
Mobile phase: A: water containing 0.1% HCOOH; B: ACN containing 0.1% HCOOH
Gradient: 60/40 A/B to 5/95 A/B in 0.5 min, total run time 4 min
Flow rate: 0.5 mL/min
Column temp.: room temperature
Injection volume: 20 μL
Calibration curve range:
Plasma: 2.5-500 nM (linear regression; $R^2$=0.9994); LLOQ=2.5 nM
RBC: 2.5-500 nM (linear regression; $R^2$=0.9998); LLOQ=2.5 nM
Kidney: 2.5-500 nM (linear regression; $R^2$=0.9993); LLOQ=2.5 nM
Lung: 2.5-500 nM (linear regression; $R^2$=0.9993); LLOQ=2.5 nM
Heart: 2.5-500 nM (linear regression; $R^2$=0.9997); LLOQ=2.5 nM
Liver: 2.5-500 nM (linear regression; $R^2$=1.0000); LLOQ=2.5 nM
0.5-5 μM (linear regression; $R^2$=0.9970); LLOQ=0.5 μM
Brain: 2.5-500 nM (linear regression; $R^2$=0.9998); LLOQ=2.5 nM
0.5-5 μM (linear regression; $R^2$=0.9992); LLOQ=0.5 μM
Results
Formulations
The dosing solution was confirmed to have about 98.1% accuracy by HPLC.
Tissue Distribution
The concentrations of ganetespib in plasma, RBC and the tissues are summarized in FIG. 1 at each time point.
The mean plasma concentration of ganetespib at 5 min after IV injection was 160 μM, highest among all the tissues studied. Thereafter, the plasma ganetespib concentration declined quickly and at 6 hr, it was 0.12 μM. At 24 hr, it was below the lower limit of quantitation (LLOQ, <2.5 nM).

After IV injection, ganetespib was widely distributed to the normal tissues analyzed. At 5 min, the highest concentration of ganetespib among the tissues was observed in kidney (57.8 µM), followed by liver (46.3 µM) and heart (36.2 µM). In brain, 0.53 µM of ganetespib was detected at 5 min, which was the lowest among the tissues. In all the normal tissues, the concentrations of ganetespib decreased quickly.

Although the concentration of ganetespib in tumor at 5 min (2.35 M) was lower than that in plasma and most of the other tissues studied, it remained relatively constant up to 24 hr (0.85 µM at 24 hr). However, the in vitro $IC_{50}$ values of ganetespib are small, and the tumor concentration of ganetespib at 24 hr was significantly higher than $IC_{50}$ of in vitro HER2 assays (~30 nM). Thus, the prolonged efficacy is expected even after ganetespib was cleared from the blood stream.

The mean concentration of ganetespib in plasma was about 10 times higher than that in RBC at 5 min time point, indicating that ganetespib tends to stay in plasma rather than in RBCs.

Conclusion

Ganetespib appeared to persist longer in tumor than in plasma or any other tissues studied. The results from this study suggest that ganetespib also has a higher binding affinity to Hsp90 from tumor cells than Hsp90 from normal cells, and that it is possible for ganetespib to modulate relative protein concentrations of Hsp90 and its client proteins selectively in tumors. The plasma concentrations of ganetespib did not correlate to the concentrations in tumor.

Summary

Ganetespib was widely distributed to various tissues. The compound was accumulated in tumor relative to the plasma and other tissues, indicating the higher binding affinity of this compound to Hsp90 in tumor than Hsp90 in other tissues. The metabolite M2, which was previously thought to be human-specific, was also detected in mouse liver, kidney, heart and lung, but not in plasma. M2 does not seem to be excreted into blood stream in mice and possibly in other species as well.

Example 8—Cytotoxicity Assay

Cell Lines.

Human H3122 NSCLC cells are obtained and grown in RPMI in the presence of fetal bovine serum (10%), 2 mM L-glutamine and antibiotics (100 IU/ml penicillin and 100 µg/ml streptomycin, Sigma Aldrich.) Cells are maintained at 37° C., 5% $CO_2$ atmosphere.

Cell Viability Assays.

Cell viability is measured using the CellTiter-Glo® assay (Promega). In brief, cells are plated in 96-well plates in triplicate at optimal seeding density (determined empirically) and incubated at 37° C., 5% $CO_2$ atmosphere for 24 hr prior to the addition of drug or vehicle (0.3% DMSO) to the culture medium. At the end of the assay, CellTiter-Glo® is added to the wells per manufacturer's recommendation, shaken for two minutes and incubated for 10 minutes at room temperature. Luminescence (0.1 sec) is measured with a Victor II microplate reader (Perkin Elmer®) and the resulting data are used to calculate cell viability, normalized to vehicle control.

TABLE 1

Concentrations of ganetespib in tissues:

| Test Articles | ganetespib |
|---|---|

Structure

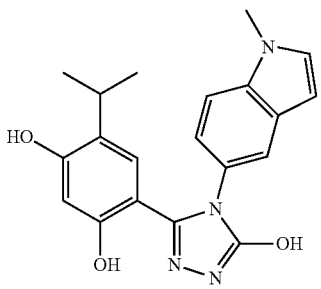 [SMILES: CC(C)c1cc(-c2nnc(O)n2-c2ccc3c(ccn3C)c2)c(O)cc1O]

| Species | CD-1-nu/nu female mice |
|---|---|
| Tumor | RERF human NSCLC |
| Route | IV |
| Dosage | 50 mg/kg |
| Formulation | DRD |

| Time | plasma (µg/mL) | RBC (µg/mL) | tumor (µg/g) | liver (µg/g) | kidneys (µg/g) | brain (µg/g) | heart (µg/g) | lung (µg/g) |
|---|---|---|---|---|---|---|---|---|
| 5 min | 58.4 | 6.00 | 0.86 | 16.9 | 21.1 | 0.19 | 13.2 | 9.24 |
| 6 hr | 0.04 | No data | 0.29 | 0.14 | 0.06 | 0.07 | 0.05 | 0.05 |
| 24 hr | <LLOQ | 0.003 | 0.31 | 0.005 | 0.01 | 0.04 | 0.00 | 0.00 |

| Time | plasma (µM) | RBC (µM) | tumor (µM) | liver (µM) | kidneys (µM) | brain (µM) | heart (µM) | lung (µM) |
|---|---|---|---|---|---|---|---|---|
| 5 min | 160 | 16.5 | 2.35 | 46.3 | 57.8 | 0.53 | 36.2 | 25.4 |
| 6 hr | 0.12 | N/A | 0.80 | 0.39 | 0.15 | 0.18 | 0.13 | 0.14 |
| 24 hr | <LLOQ | 0.007 | 0.85 | 0.01 | 0.02 | 0.12 | 0.00 | 0.005 |

Cells as described above are treated with exemplary SDC-TRAPs and their viability is determined as above as well. These assays demonstrate that the SDC-TRAP effector and targeting components maintain the cytotoxic activity against cancer cells in the conjugate.

Example 9—Assessing Anti-Tumor Activity of SDC-TRAPS in Xenogeneic Human Tumor Mouse Model Xenogeneic human tumor mouse models are well known in the art in which human tumors are implanted in immunocompetent mice. Various agents are tested for their efficacy in promoting tumor shrinkage. Human tumor cell lines for use in such models include, but are not limited to HCT-116 colon cancer model and MCF-7 breast cancer model. It is understood that other cell lines are known in the art and can be selected for use based on, at least, the drug in the drug conjugate and/or the targeting moiety in the drug conjugate. An exemplary study is provided for non-specified SDC-TRAP-A and SDC-TRAP-B which include effector A and effector B, respectively, in combination with the same binding domain. It is understood that variations of the experimental design can be readily envisioned to analyze the efficacy of SDC-TRAPs.

A xenograft tumor model is used to evaluate the anti-tumor efficacy of SDC-TRAP-A and SDC-TRAP-B. The tumor model is established by transplanting equivalent numbers of human tumor cells, e.g., HCT-116 cells, into mice and testing the effect of the SDC-TRAPs on tumor volume and change in tumor volume.

Tumor cells of interest, e.g. HCT 116 human colorectal adenocarcinoma tumor cells are purchased from ATCC. The cells are maintained in vitro as a monolayer culture in McCoy's 5a Medium. Fetal bovine serum is added to the medium. The final concentration of fetal bovine serum is 10%. Cells are cultured at 37° C. and 5% $CO_2$. The tumor cells are routinely sub-cultured twice weekly by trypsin-EDTA treatment. Cells in an exponential growth phase are harvested and counted for tumor inoculation.

100 18-22 g, 5-7 week old, female BALB/cA nude mice are inoculated with an appropriate tumor cell line of interest, e.g. HCT 116 cells ($2.0 \times 10^6$, 1:1 with Matrigel), subcutaneously on the back of each animal (0.1 mL/mouse). When the average tumor volume reaches about 150-250 $mm^3$, 60 of the inoculated mice are selected based on tumor growth and randomly grouped into 6 treatment groups (10 mice per group) according to the following table. Mice that are not put on treatment are euthanized. Animals are sourced through Shanghai SINO-British SIPPR/BK Lab Animal Ltd, Shanghai, China. Mice are treated as set forth in the table below:

Exemplary Treatment Groups

Dose Preparation & Treatment Schedule

The dosing solutions of SDC-TRAP-A, SDC-TRAP-B, unconjugated effector moiety, and unconjugated binding moiety (e.g., ganetespib) are prepared according to an appropriate formulation protocol and administered using routine methods.

Evaluation of Anti-Tumor Activity

During the treatment period, the implanted tumors are measured by caliper twice per week. The tumors are measured for the maximum width (X) and length (Y) and the tumor volumes (V) are calculated using the formula: $V=(X^2Y)/2$. The differences in the tumor volume between the control and treatment groups are analyzed for significance using the unpaired two-tailed Student's t-test. $P<0.05$ is considered to be statistically significant. The animal body weights are also weighed and recorded twice per week. The changes in tumor volume and body weight in the days following compound treatment are determined. The effects of the SDC-TRAPs are compared to each other, to the effector and binding moiety that are used to generate that SDC-TRAPs, and untreated control to identify an SDC-TRAP with improved efficacy in inhibiting tumor growth without adverse effects (e.g., excessive weight loss).

Example 10—Determination of $IC_{50}$ by Assessing the Effects of Various SDC-TRAPs on Tumor Shrinkage An appropriate cell line, e.g., H3122 cells, are seeded into in 96-well plates at 7,500 cells/90 µL/well, and are incubated for 24 hours. SDC-TRAPs, plus a binding moiety alone (e.g., ganetespib) as a control, are serially diluted in dimethylsulfoxide (DMSO) (e.g., 3000 nM, 1000 nM, 333.3 nM, 111.1 nM, 37.0 nM, 12.3 nM) into each of six wells of each 96-well plate. To each well of a first set of duplicate plates, 145 µL of media is added, and the cells are incubated. The wells of a second set of duplicate plates (pulsed plates) are incubated for 1 hour, then the wells are rinsed 2× with fresh media to remove the conjugate, and 145 µL of media is then added to each washed well. $IC_{50}$ is determined visually under a microscope after 48 hours and 72 hours drug-exposure. Also at the 72 hour time point, 50 µL of the cell culture supernatant is mixed with 50 µL of CellTiter-Glo® and the luminescence is determined, from which an $IC_{50}$ for each conjugate is calculated.

Example 11—$IC_{50}$ of Continuous and Pulsed Exposure to SDC-TRAPs $IC_{50}$ toxicity is determined for 72 hour continuous exposure to SDC-TRAPs run in triplicate, and for duplicate pulse

| Groups | Animal Number | Treatment | Dosage (mg/kg) | Dosage Conc. (mg/mL) | Dosage Vol. (mL/kg) | Route of Adm. | Dosing Schedule |
|---|---|---|---|---|---|---|---|
| 1 | 10 | Vehicle | NA | NA | 10 | IV | Q7D x 3 |
| 2 | 10 | SDC-TRAP-A | 200 | 20 | 10 | IV | Q7D x 3 |
| 3 | 10 | SDC-TRAP-A | 100 | 10 | 10 | IV | Q7D x 3 |
| 4 | 10 | SDC-TRAP-B | 94 | 9.4 | 10 | IV | Q7D x 3 |
| 5 | 10 | Unconjugated effector-A | 67 | 6.7 | 10 | IV | Q7D x 3 |
| 6 | 10 | Unconjugated effector-B | 67 | 6.7 | 10 | IV | Q7D x 3 |
| 7 |  | Unconjugated binding | 100 | 10 | 10 | IV | Q7D x 3 | exposure (1 hour "pulse" exposure to conjugate compound, followed by 72 hour incubation in conjugate-free media) using H3211 cells, according to the protocol set forth in Example 12.

Example 12—Hsp90$\alpha$ Binding Assay Protocol

An Hsp90$\alpha$ fluorescence assay kit from BPS Bioscience (Cat #50294) containing Hsp90 recombinant enzyme, FITC-labeled geldanamycin, assay buffer and a low binding 384-well plate is used to assay Hsp90$\alpha$ binding. Dithiothreitol (DTT) (Cat #D0643) and bovine serum albumin (BSA) (Cat #A2153) are obtained from Sigma-Aldrich. Fluorescence polarization is measured using a PHERAstar® microplate reader (BMG LABTECH GmbH, Ortenberg, Germany.)

The SDC-TRAP and control compounds are diluted to 1 mM in DMSO and loaded into a compound dilution plate to make 3-fold dilutions yielding a total of 8 concentrations. 1 µL of compound is transferred from the dilution plate to the low binding assay plate provided in the assay kit. 5 mL of Hsp90$\alpha$ binding solution is prepared having a final concentration of 7 ng/µL Hsp90$\alpha$, 5 nM FITC-labeled geldanamycin, 2 mM DTT and 0.1 mg/mL BSA. 49 µL of binding solution is added to each microplate well, incubated at room temperature for 1 hour, then read using the PHERAstar® microplate reader. The high control sample contains no compound plus Hsp90$\alpha$; the low control sample contains no compound and no Hsp90$\alpha$. Percent inhibition is calculated using high control as 100% and low control as 0% inhibition. The $IC_{50}$ is calculated using GraphPad Prism® 4 software.

Example 13—Cytotoxicity Assay with Cancer Cell Lines

Cytotoxicity of SDC-TRAP molecules is determined in multiple cancer cell line such as the three exemplary cancer cell lines provided herein. 5000 cells/100 µL/well of human breast cancer cell line BT-474 (ATCC #HTB-20) and human urinary bladder cancer cell line SW780 (ATCC#CRL-2169) and 5000 cells/well of human urinary bladder cancer cell line RT-112 are seeded into 96-well flat-bottom tissue cultures plates and incubated overnight at 37° C. in 5% $CO_2$. BT-474 and SW780 cells are cultured in DMEM+10% FBS, +1% P/S, +1.5 g/L sodium bicarbonate; RT-112 cells are cultured in EMEM+10% FBS, +1% P/S. SDC-TRAP-0178 is titrated by 10-fold dilutions from 10 µM to 10 nM and added to the plate at 10 µL/well. Final concentration of DMSO in the cell plate is 0.25%. The plates are incubated for 72 hours at 37° C. in 5% $CO_2$. 80 µL of CellTiter-Glo is added to each well, followed by room temperature incubation in the dark for 15 minutes. Cell is determined by luminescence. $IC_{50}$ is calculated using XLFIT software.

Example 14—Tissue Distribution Extraction Procedure for SDC-TRAP Tumor Samples

SDC-TRAP molecules have the ability to be specifically targeted to desired cells. For example, SDC-TRAP molecules can be targeted to tumors and tumor cells in order to treat cancer. This example sets forth a protocol to extract the SDC-TRAP molecules of the invention from tumor samples.

A 150 ng/mL solution of an SDC-TRAP in methanol is prepared using an internal spiking solution (500 µg/mL SDC-TRAP-0002 in DMSO). Using the 10 mM stock solutions of the SDC-TRAP molecule and its Hsp90i binding moiety and effector moiety in DMSO, spiking solutions are prepared at 0.025, 0.05, 0.1, 0.5, 1, 5, 10, 50, 100, 250, and 500 µM in DMSO. 5 µL of each spiking solution is added to a 96-deep well plate.

Quality control standards are prepared from 5 µL of 0.1, 1, and 10 µM calibration standard spiking solution added in triplicate into 96-deep well plate and adding 50 µL of matrix (plasma or homogenized tumor).

To prepare test samples, test plasma is diluted as needed using blank plasma. Tumor samples are pulverized in liquid nitrogen, weighed, and homogenized in PBS at 5× volume to sample weight. 50 µL of unknown plasma or homogenized tumor sample is mixed with 5 µL of DMSO. The samples are extracted by precipitating calibration standards, QC standards, and unknown samples with 200 µL of internal standard solution. The samples are mixed by vortex at room temperature for approximately 1.5 minutes, then centrifuge at 2-8° C. 150 µL of supernatant is collected and 25 µL of water added. Samples are mixed and analyzed by LC-MS/MS.

Example 15—Plasma Stability Protocol for SDC-TRAP Compounds

An exemplary assay to analyze plasma stability of SDC-TRAPs is provided. 150 ng/mL solution of SDC-TRAP-0002 in methanol is prepared using the internal standard spiking solution. This solution is used to precipitate all plasma samples in the study. 200 µL is pipetted into a 96 deepwell plate over dry ice. 10 µL of 1 mM stock in DMSO is added to a 1.5 mL microfuge tube, then 990 µL of plasma. Samples are mixed by vortex, then 50 µL of each sample is added in triplicate to a 96-well plate containing internal standard solution. This was designated the 0 hour time point sample. 250 µL of the remaining plasma sample is added to each of four 96 deepwell plates—one per time point. Samples are incubated at 37° C. with gentle shaking for 0.25, 0.5, and 1 hour. After each time point, one plate of each sample is removed from the shaker and placed on wet ice for approximately 2 minutes. 50 µL plasma aliquots (in triplicate) are added to the deepwell plate containing internal standard solution. After the last time point is extracted, the 96 deepwell plate is vortexed, then centrifuged at 2-8° C. 150 µL of supernatant is collected and 25 µL of water was added. Samples are mixed and analyzed by LC-MS/MS.

Example 16—Identification and Use of SDC-TRAP for Prevention and Treatment of Skin Cancers and Actinic Keratosis Skin cancers (neoplasms) are named after the type of skin cell from which they arise. Skin cancers include basal cell carcinoma, squamous cell carcinoma, malignant melanomas, and Bowen's disease. Actinic keratosis can be, but is not always, a precursor to squamous cell carcinoma.

Drugs used for the treatment of skin cancer are selected based on the type and severity of the skin cancer. Superficial, non-melanoma skin cancers can be treated with topical agents, either alone or in combination with surgery or other therapeutic interventions. Such agents include, but are not limited to, retinoids, 5-fluorouracil, diclofenac, ingenol mebutate, and imiquimod. Topical delivery permits administration of the chemotherapeutic agent directly to the site of the tumor or skin lesion. However, the delivery of active agents into the skin can be challenging. Moreover, many topical therapeutic agents can be irritating to the skin, resulting in scar formation, further inhibiting the delivery of the active agent to the site.

Imiquimod 3-(2-methylpropyl)-3,5,8-triazatricyclo[7.4.0.02,6]trideca-1(9),2(6),4,7,10,12-hexaen-7-amine) is a patient-applied cream used to treat certain diseases of the skin, including skin cancers (basal cell carcinoma, Bowen's disease, superficial squamous cell carcinoma, some superficial malignant melanomas, and actinic keratosis) as well as genital warts (condylomata acuminata). Imiquimod and its analogs activate the immune system by activating immune cells through the toll-like receptor 7 (TLR7), commonly involved in pathogen recognition. Imiquimod can be used in combination with one or more drugs used for the treatment of skin diseases to make an SDC-TRAP molecule.

An imiquimod SDC-TRAP molecule can be formed, for example, using any known linker, such as those provided herein, with the desired effector molecule. The specific linker and conjugation method used will depend, for example, on the chemical nature of the effector molecule.

Assays to determine the cytotoxicity of the imiquimod SDC-TRAP molecules are performed using methods similar to those provided in Example 4. Cell viability assays are performed on non-transformed cells, preferably skin cells, to identify SDC-TRAPs with acceptable toxicities, preferably compounds with toxicity that is not greater than either of the parent compounds. Cytotoxicity and skin irritation assays are also performed, for example, on pig skin, which is frequently used as a model for human skin in toxicity/irritation assays, using routine methods.

Imiquimod SDC-TRAP molecules are also tested to confirm that their efficacy is not inhibited by the formation of the conjugate. A number of skin cancer cell lines are well known in the art. Dose response curves are generated to demonstrate the efficacy of imiquimod SDC-TRAP molecules in killing cancer cells. Preferably, the imiquimod SDC-TRAP molecules are more effective at killing skin cancer cells than imiquimod or the effector molecule alone.

Methods to assess pharmacokinetic and pharmacodynamic properties of an agent are well known in the art. As noted above, pig skin is frequently used as a model for human skin, both in toxicity/irritation assays, but also in assaying uptake and delivery of agents into skin layers and cells. Topical formulations of imiquimod, the effector molecule, and imiquimod SDC-TRAP molecules are assayed for uptake, transport through the skin, and persistence in the skin using routine methods.

Having identified a imiquimod SDC-TRAP molecule with the desired activity, cytotoxicity, pharmacokinetic properties, and improved tissue delivery, the SDC-TRAPs are tested for their efficacy in an appropriate animal model of skin cancer. Animal models of skin cancer are well known in the art. For example, xenograph tumor models using squamous cell carcinoma, basal cell carcinoma, or melanoma cell lines are used with subcutaneously implanted tumors. Topical formulations of imiquimod, the effector molecule, and imiquimod SDC-TRAP molecules are applied. The activity of the conjugate is compared to the activity of each imiquimod and the effector molecule alone. Imiquimod SDC-TRAP molecules having one or more improved properties as compared to either of the parent molecules are further characterized in other animal systems and humans.

The SDC-TRAPs are found to have one or more improved properties in the treatment of humans including, but not limited to, decreased toxicity, improved dosing schedule, or alternate route of administration.

Example 17—Determining the Permeability of SDC-TRAP Molecules

In order to test the ability SDC-TRAP molecules of the invention to enter cells, an artificial membrane permeability assay ("PAMPA") can be used. PAMPAs are useful tool for predicting in vivo drug permeability for drugs that enter cells by passive transport mechanisms. LC/MS is used in conjunction with PAMPA assays to determine the ability of the SDC-TRAP molecules of the invention to permeate cells.

Pre-coated PAMPA plates are warmed to room temperature for at least 30 minutes prior to adding assay components.

Stock solutions are prepared with the SDC-TRAP molecules to be tested. In order to make a working solution, either 50 μL of 100 μM Stock in DMSO+950 μL of PBS or 50 μL of 200 μM stock is added to 96 deep well plate, resulting in a 5 μM final concentration or a 10 μM final concentration, respectively. 300 μL of the working solution containing each compound to be tested is added to the appropriate well of a donor PAMPA plate. 200 μL of PBS is added into the corresponding wells of an acceptor PAMPA plates.

The acceptor plate is lowered onto the donor plate and allowed to incubate for five hours. After five hours, a 50 μL aliquot is removed from each well of each plate and added into a new 96 deep-well plate.

100 μL of methanol containing an internal standard is added to each aliquot and analyzed by LC/MS.

In order to calculate the permeability for each SDC-TRAP molecule and the control molecules, the following formula was used:

Permeability (in unit of cm/s):

$$P_e = \frac{-\ln[1 - C_A(t)/C_{equilibrium}]}{A * (1/V_D + 1/V_A) * t}$$

$$C_{equilibrium} = \frac{C_D(t) * V_D + C_A(t) * V_A}{V_D + V_A}$$

Mass Retention:

$$R = \frac{1 - [C_D(t) * V_D + C_A(t) * V_A]}{C_0 * V_D}$$

$C_0$ = initial compound concentration in donor well (mM)

$C_D(t)$ = compound concentration in donor well at time $t$. (mM)

$C_A(t)$ = compound concentration in acceptor well at time $t$. (mM)

$V_D$ = donor well volume = 0.3 mL $V_A$ = acceptor well volume = 0.2 mL $A$ = filter area = 0.3 cm$^2$ $t$ = incubation time = 18000 s (5 h)

Example 18—Pharmacodynamics of SDC-TRAP in Xenograft Tumors

SDC-TRAPs can be identified for potent and durable antitumor activity in particular tumor types suggesting that the drug is slowly cleaved over its residence time in the tumor to provide long term activity. To determine whether these effects are through the binding moiety, e.g., an HSP90 binding moiety that results in Hsp90 inhibition, effector agent activity, i.e., anticancer activity, e.g., kinase inhibitor activity, or both, the stability of Hsp90 client proteins as well as the phosphorylation of the kinase substrate as a readout for effector molecule activity. Readouts can be assessed in various tissues as well as tumor tissue to determine changes in tissue distribution and clearance as well as activity (e.g., to understand mechanism of reduced toxicity due to better tumor targeting).

Kinetics of Hsp90 inhibition and kinase activity inhibition are assayed at time points relative to the known metabolism of the component agents of the SDC-TRAP. Selection of time points and concentrations of the various agents is well within the ability of those of skill in the art. The analysis demonstrates the relative activity of each of the components of the SDC-TRAP and changes in kinetics and/or tissue distribution as a result of the conjugate formation.

All publications, patent applications, patents, and other documents cited herein are incorporated by reference in their entirety. In case of conflict, the present specification, including definitions, will control.

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

We claim:

1. A binding moiety-drug conjugate (SDC-TRAP) comprising a binding moiety and an effector moiety, wherein the effector moiety is a proteasome inhibitor selected from the group consisting of bortezomib, ixazomib, and delanzomib, or fragment thereof, the binding moiety binds to HSP90, and the binding moiety and the effector moiety are covalently attached.

2. The SDC-TRAP of claim 1, wherein the binding moiety is an Hsp90 ligand or a prodrug thereof.

3. The SDC-TRAP of claim 2, wherein the Hsp90 ligand is an Hsp90 inhibitor.

4. The SDC-TRAP of claim 3, wherein the Hsp90 inhibitor is selected from the group consisting of ganetespib, geldanamycins, macbecins, tripterins, tanespimycins, and radicicols.

5. The SDC-TRAP of claim 2, wherein the molecular weight of the SDC-TRAP is less than about 1600 Daltons, less than about 1200 Daltons, less than about 800 Daltons, less than about 600 Daltons or less than about 200 Daltons.

6. The SDC-TRAP of claim 1, wherein the binding moiety and the effector moiety are covalently attached by a linker.

7. The SDC-TRAP of claim 6, wherein the linker comprises a cleavable linker.

8. The SDC-TRAP of claim 1, wherein the SDC-TRAP is able to enter a cell by passive diffusion.

9. The SDC-TRAP of claim 1, wherein the SDC-TRAP is able to enter a cell by active transport.

10. A binding moiety-drug conjugate (SDC-TRAP) or its pharmaceutically acceptable salt, wherein the SDC-TRAP is selected from the group consisting of SDC-TRAP-0236, SDC-TRAP-0237, SDC-TRAP-0238, SDC-TRAP-0239, SDC-TRAP-0240, SDC-TRAP-0241, SDC-TRAP-0242, SDC-TRAP-0243, SDC-TRAP-0244, SDC-TRAP-0245, SDC-TRAP-0246, SDC-TRAP-0247, SDC-TRAP-0248, SDC-TRAP-0249, SDC-TRAP-0250, SDC-TRAP-0251, and SDC-TRAP-0252.

11. A pharmaceutical composition comprising a therapeutically effective amount of at least one SDC-TRAP of claim 1, and at least one pharmaceutical excipient.

12. A pharmaceutical composition comprising a therapeutically effective amount of at least one SDC-TRAP of claim 10, and at least one pharmaceutical excipient.

* * * * *